(12) United States Patent
Fortson et al.

(10) Patent No.: US 9,370,353 B2
(45) Date of Patent: Jun. 21, 2016

(54) SUTURING DEVICES AND METHODS

(71) Applicant: Abbott Cardiovascular Systems, Inc., Santa Clara, CA (US)

(72) Inventors: Aaron M. Fortson, Fremont, CA (US); Wouter E. Roorda, Palo Alto, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 350 days.

(21) Appl. No.: 13/791,858

(22) Filed: Mar. 8, 2013

(65) Prior Publication Data

US 2013/0190781 A1     Jul. 25, 2013

Related U.S. Application Data

(63) Continuation-in-part of application No. 12/873,728, filed on Sep. 1, 2010, now Pat. No. 8,663,252.

(51) Int. Cl.
*A61B 17/00*     (2006.01)
*A61B 17/04*     (2006.01)

(52) U.S. Cl.
CPC ......... *A61B 17/0469* (2013.01); *A61B 17/0057* (2013.01); *A61B 2017/00663* (2013.01); *A61B 2017/0472* (2013.01); *A61B 2017/0474* (2013.01)

(58) Field of Classification Search
CPC ........... A61B 17/0469; A61B 17/0482; A61B 2017/00663; A61B 2017/047; A61B 2017/0488; A61B 17/0057; A61B 2017/0472; A61B 2017/0474
See application file for complete search history.

(56) References Cited

U.S. PATENT DOCUMENTS

| 312,408 | A | 2/1885 | Wackerhagen |
| 597,165 | A | 1/1898 | Hall |
| 659,422 | A | 10/1900 | Shidler |
| 989,231 | A | 4/1911 | Davis |
| 1,574,362 | A | 9/1922 | Callahan |
| 1,625,602 | A | 4/1927 | Gould et al. |
| 1,940,351 | A | 3/1933 | Howard |
| 2,012,776 | A | 8/1935 | Roeder |
| 2,131,321 | A | 10/1937 | Hart |

(Continued)

FOREIGN PATENT DOCUMENTS

| DE | 912619 | 5/1954 |
| DE | 4210724 | 7/1993 |

(Continued)

OTHER PUBLICATIONS

U.S. Appl. No. 13/485,388, May 21, 2015, Office Action.

(Continued)

*Primary Examiner* — Katherine M Shi
*Assistant Examiner* — Michael Mendoza
(74) *Attorney, Agent, or Firm* — Workman Nydegger; Randy Shen

(57) ABSTRACT

A surgical device for suturing body lumen is described, as well as methods for suturing tissue employing the surgical device. The device can include a body having a shaft and a foot for insertion into an opening in a body lumen. The device can include tissue ports between configured to receive tissue surrounding the opening in the body lumen. The foot can include a suture secured to needle capture devices. The device can include needles that can be advanced through tissue and into the needle capture devices. The needle capture devices can then be withdrawn, thereby harvesting the suture, which can then be used to close the opening in the body lumen.

18 Claims, 43 Drawing Sheets

(56) References Cited

U.S. PATENT DOCUMENTS

| | | |
|---|---|---|
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,580,566 A | 4/1986 | Hsu |
| 4,586,614 A | 5/1986 | Ger |
| 4,587,969 A | 5/1986 | Gillis |
| 4,596,559 A | 6/1986 | Fleischhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Ovil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yo on |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bognato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |

(56) References Cited

U.S. PATENT DOCUMENTS

| | | |
|---|---|---|
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Delia Badia et al. |
| 5,397,326 A | 3/1995 | Mangum |
| 5,403,329 A | 4/1995 | Hinchcliffe |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A | 5/1995 | Jackson et al. |
| 5,417,699 A | 5/1995 | Klein et al. |
| 5,419,765 A | 5/1995 | Weldon et al. |
| 5,425,705 A | 6/1995 | Evard et al. |
| 5,425,737 A | 6/1995 | Burbank et al. |
| 5,425,740 A | 6/1995 | Hutchinson, Jr. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Hartnett |
| 5,531,700 A | 7/1996 | Moore et al. |
| 5,536,273 A | 7/1996 | Lehrer |
| 5,540,701 A | 7/1996 | Sharkey et al. |
| 5,540,703 A | 7/1996 | Barker, Jr. et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | DeLange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,649,959 A | 7/1997 | Hannam et al. |
| 5,662,664 A | 9/1997 | Gordon et al. |
| 5,669,917 A | 9/1997 | Sauer et al. |
| 5,676,689 A | 10/1997 | Kensey et al. |
| 5,700,273 A | 12/1997 | Buelna et al. |
| 5,707,379 A | 1/1998 | Fleenor et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |
| 5,728,114 A | 3/1998 | Evans et al. |
| 5,728,133 A | 3/1998 | Kontos |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,766,183 A | 6/1998 | Sauer |
| 5,766,186 A | 6/1998 | Faraz et al. |
| 5,766,217 A | 6/1998 | Christy |
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,810,884 A | 9/1998 | Kim |
| 5,814,069 A | 9/1998 | Schulze et al. |

(56) References Cited

U.S. PATENT DOCUMENTS

| | | | |
|---|---|---|---|
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,871,490 A | 2/1999 | Schulze et al. |
| 5,871,502 A | 2/1999 | Suryadevara |
| 5,873,876 A | 2/1999 | Christy |
| 5,876,411 A | 3/1999 | Kontos |
| 5,895,404 A | 4/1999 | Ruiz |
| 5,897,487 A | 4/1999 | Ouchi |
| 5,897,564 A | 4/1999 | Schulze et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,906,631 A | 5/1999 | Imran |
| 5,919,207 A | 7/1999 | Taheri |
| 5,921,994 A | 7/1999 | Andreas et al. |
| 5,928,266 A | 7/1999 | Kontos |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A | 10/1999 | Greenstein |
| 5,964,782 A | 10/1999 | Lafontaine et al. |
| 5,972,030 A | 10/1999 | Garrison et al. |
| 5,976,161 A | 11/1999 | Kirsch et al. |
| 5,980,539 A | 11/1999 | Kontos |
| 5,997,555 A | 12/1999 | Kontos |
| 6,001,109 A | 12/1999 | Kontos |
| 6,022,372 A | 2/2000 | Kontos |
| 6,024,747 A | 2/2000 | Kontos |
| 6,036,699 A | 3/2000 | Andreas et al. |
| 6,042,601 A | 3/2000 | Smith |
| 6,048,351 A | 4/2000 | Gordon et al. |
| 6,048,354 A | 4/2000 | Lawrence |
| 6,048,357 A | 4/2000 | Kontos |
| 6,068,603 A | 5/2000 | Suzuki |
| 6,077,276 A | 6/2000 | Kontos |
| 6,077,279 A | 6/2000 | Kontos |
| 6,117,144 A | 9/2000 | Nobles et al. |
| 6,117,145 A | 9/2000 | Wood et al. |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A | 10/2000 | Modesitt et al. |
| 6,139,556 A | 10/2000 | Kontos |
| 6,152,936 A | 11/2000 | Christy et al. |
| 6,165,183 A | 12/2000 | Kuehn et al. |
| 6,165,204 A | 12/2000 | Levinson et al. |
| 6,190,396 B1 | 2/2001 | Whitin et al. |
| 6,197,042 B1 | 3/2001 | Ginn et al. |
| 6,206,893 B1 | 3/2001 | Klein et al. |
| 6,206,895 B1 | 3/2001 | Levinson |
| 6,245,079 B1 | 6/2001 | Nobles et al. |
| 6,248,124 B1 | 6/2001 | Pedros et al. |
| 6,296,657 B1 | 10/2001 | Brucker |
| 6,302,870 B1 | 10/2001 | Jacobsen et al. |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,395,015 B1 | 5/2002 | Borst et al. |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |
| 6,451,031 B1 | 9/2002 | Kontos |
| 6,511,489 B2 | 1/2003 | Field et al. |
| 6,517,553 B2 | 2/2003 | Klein et al. |
| 6,533,812 B2 | 3/2003 | Swanson et al. |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carley et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,695,867 B2 | 2/2004 | Ginn et al. |
| 6,716,228 B2 | 4/2004 | Tal |
| 6,743,195 B2 | 6/2004 | Zucker |
| 6,743,259 B2 | 6/2004 | Ginn |
| 6,749,621 B2 | 6/2004 | Pantages et al. |
| 6,749,622 B2 | 6/2004 | McGuckin, Jr. et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 | 6/2005 | Nobles et al. |
| 6,939,357 B2 | 9/2005 | Navarro et al. |
| 6,964,668 B2 | 11/2005 | Modesitt et al. |
| 6,969,371 B2 | 11/2005 | Palasis et al. |
| 6,969,397 B2 | 11/2005 | Ginn |
| 7,001,400 B1 | 2/2006 | Modesitt et al. |
| 7,029,480 B2 | 4/2006 | Klein et al. |
| 7,029,481 B1 | 4/2006 | Burdulis, Jr. et al. |
| 7,048,747 B2 | 5/2006 | Arcia et al. |
| 7,063,710 B2 | 6/2006 | Takamoto et al. |
| 7,083,635 B2 | 8/2006 | Ginn |
| 7,108,710 B2 | 9/2006 | Anderson |
| 7,112,225 B2 | 9/2006 | Ginn |
| 7,131,980 B1 | 11/2006 | Field et al. |
| 7,160,309 B2 | 1/2007 | Voss |
| 7,179,266 B2 | 2/2007 | Kontos |
| 7,229,458 B2 | 6/2007 | Boecker et al. |
| 7,235,087 B2 | 6/2007 | Modesitt et al. |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,442,198 B2 | 10/2008 | Gellman et al. |
| 7,445,626 B2 | 11/2008 | Songer et al. |
| 7,449,024 B2 | 11/2008 | Stafford |
| 7,462,188 B2 | 12/2008 | McIntosh |
| 7,753,923 B2 | 7/2010 | St. Goar et al. |
| 7,837,696 B2 | 11/2010 | Modesitt et al. |
| 7,842,047 B2 | 11/2010 | Modesitt et al. |
| 7,842,048 B2 | 11/2010 | Ma |
| 7,842,049 B2 | 11/2010 | Voss |
| 7,846,170 B2 | 12/2010 | Modesitt et al. |
| 7,850,701 B2 | 12/2010 | Modesitt |
| 7,883,517 B2 | 2/2011 | Pantages et al. |
| 8,038,688 B2 | 10/2011 | Modesitt et al. |
| 8,048,092 B2 | 11/2011 | Modesitt et al. |
| 8,057,491 B2 | 11/2011 | Modesitt et al. |
| 8,083,754 B2 | 12/2011 | Pantages et al. |
| 8,137,364 B2 | 3/2012 | Zung et al. |
| 8,172,860 B2 | 5/2012 | Zung et al. |
| 8,202,281 B2 | 6/2012 | Voss |
| 8,211,122 B2 | 7/2012 | McIntosh |
| 8,252,008 B2 | 8/2012 | Ma |
| 8,257,368 B2 | 9/2012 | McIntosh |
| 8,267,947 B2 | 9/2012 | Pantages et al. |
| 8,313,498 B2 | 11/2012 | Pantages et al. |

(56) References Cited

U.S. PATENT DOCUMENTS

| | | |
|---|---|---|
| 8,323,298 B2 | 12/2012 | Modesitt et al. |
| 8,361,088 B2 | 1/2013 | McIntosh |
| 2001/0046518 A1 | 11/2001 | Sawhney |
| 2002/0045908 A1 | 4/2002 | Nobles et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0177876 A1 | 11/2002 | Roby et al. |
| 2003/0093093 A1 | 5/2003 | Modesitt et al. |
| 2003/0171764 A1 | 9/2003 | Debbas |
| 2003/0195529 A1 | 10/2003 | Takamoto et al. |
| 2004/0009205 A1 | 1/2004 | Sawhney |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0069397 A1 | 3/2006 | Nobles et al. |
| 2006/0100664 A1 | 5/2006 | Pai et al. |
| 2006/0167477 A1 | 7/2006 | Arcia et al. |
| 2006/0173469 A1 | 8/2006 | Klein |
| 2006/0253037 A1 | 11/2006 | Ginn et al. |
| 2006/0253072 A1 | 11/2006 | Pai et al. |
| 2007/0005079 A1 | 1/2007 | Zarbatany et al. |
| 2007/0032801 A1 | 2/2007 | Pantages et al. |
| 2007/0060950 A1 | 3/2007 | Khosravi et al. |
| 2007/0123817 A1 | 5/2007 | Khosravi et al. |
| 2007/0282354 A1 | 12/2007 | McIntosh |
| 2008/0009794 A1 | 1/2008 | Bagaoisan et al. |
| 2008/0065151 A1 | 3/2008 | Ginn |
| 2008/0065152 A1 | 3/2008 | Carley |
| 2008/0287967 A1 | 11/2008 | Andreas et al. |
| 2008/0319458 A1 | 12/2008 | Reynolds |
| 2009/0036906 A1 | 2/2009 | Stafford |
| 2009/0088779 A1 | 4/2009 | Zung et al. |
| 2011/0071567 A1 | 3/2011 | Modesitt et al. |
| 2011/0077670 A1 | 3/2011 | Modesitt et al. |
| 2011/0288563 A1 | 11/2011 | Gianotti et al. |
| 2012/0016383 A1 | 1/2012 | Sauer et al. |
| 2012/0053600 A1 | 3/2012 | Fortson |
| 2012/0150201 A1 | 6/2012 | Pantages et al. |
| 2012/0283749 A1 | 11/2012 | Sauer |
| 2012/0289903 A1 | 11/2012 | Voss |
| 2012/0316579 A1 | 12/2012 | Ma |
| 2013/0006277 A1 | 1/2013 | Stafford |
| 2013/0012962 A1 | 1/2013 | Stone |
| 2013/0066340 A1 | 3/2013 | Pantages et al. |
| 2013/0325058 A1 | 12/2013 | Roorda et al. |
| 2014/0180312 A1 | 6/2014 | Zung et al. |
| 2014/0222032 A1 | 8/2014 | Stafford |
| 2015/0025551 A1 | 1/2015 | Fortson et al. |

FOREIGN PATENT DOCUMENTS

| | | |
|---|---|---|
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |

(56) References Cited

FOREIGN PATENT DOCUMENTS

| WO | WO 2006/118877 | 11/2006 |
|----|----------------|---------|
| WO | WO 2007/019016 | 2/2007  |
| WO | WO 2007/081836 | 7/2007  |

OTHER PUBLICATIONS

U.S. Appl. No. 13/752,095, Jun. 12, 2015, Notice of Allowance.
U.S. Appl. No. 14/094,352, Jul. 8, 2015, Office Action.
U.S. Appl. No. 11/960,593, Jul. 1, 2013, Notice of Allowance.
U.S. Appl. No. 13/443,659, filed Apr. 10, 2012, Fortson et al.
U.S. Appl. No. 13/445,053, filed Apr. 24, 2012, Fortson et al.
U.S. Appl. No. 13/752,095, filed Jan. 28, 2013, McIntosh.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt, et al.
US 5,820,544, 6/1974, Semm (withdrawn).
Cardiac Catheterization and Angiography, 3rd Ed., Lea & Febiger, Philadelphia, pp. 1-49, 52-247. 1986.
Cardio-Thoracic Systems Prospectus dated Mar. 20, 1996. pp. 1-4, 25-40.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintechnik GmbH, Product Brochure entitled "REMA," Apr. 2001, 7 pages.
Serruys, PW et al., A Comparision of Balloon-Expandable-Stent Implantation With Balloon Angioplasty in Patients With Coronary Artery Disease, New England Journal of Medicine, 331:489-495, 1994.
Taber's Cyclopedic Medical Dictionary, 18th Ed., p. 747, Feb. 1997.
U.S. Appl. No. 07/989,611, May 12, 1993 Office Action.
U.S. Appl. No. 07/989,611, Aug. 1, 1994, Office Action.
U.S. Appl. No. 07/989,611, Nov. 3, 1994, Notice of Allowance.
U.S. Appl. No. 08/148,809, Sep. 16, 1994, Office Action.
U.S. Appl. No. 08/148,809, May 30, 1995, Office Action.
U.S. Appl. No. 08/148,809, Dec. 15, 1995, Notice of Allowance.
U.S. Appl. No. 08/252,124, Jun. 5, 1995, Office Action.
U.S. Appl. No. 08/252,124, Jan. 5, 1996, Office Action.
U.S. Appl. No. 08/252,124, May 22, 1996, Notice of Allowance.
U.S. Appl. No. 08/259,410, Feb. 2, 1995, Office Action.
U.S. Appl. No. 08/259,410, Jun. 1, 1995, Office Action.
U.S. Appl. No. 08/259,410, Feb. 6, 1998, Notice of Allowance.
U.S. Appl. No. 08/638,076, Jan. 21, 1997, Office Action.
U.S. Appl. No. 08/638,076, Oct. 17, 1997, Notice of Allowance.
U.S. Appl. No. 08/824,031, Mar. 16, 1998, Office Action.
U.S. Appl. No. 08/824,031, Sep. 14, 1998, Office Action.
U.S. Appl. No. 08/824,031, Apr. 13, 1999, Office Action.
U.S. Appl. No. 08/824,031, Jul. 15, 1999, Notice of Allowance.
U.S. Appl. No. 08/883,246, Jul. 23, 1998, Office Action.
U.S. Appl. No. 08/883,246, Apr. 12, 1999, Office Action.
U.S. Appl. No. 08/883,246, Oct. 13, 1999, Office Action.
U.S. Appl. No. 08/883,246, Oct. 23, 2000, Office Action.
U.S. Appl. No. 08/883,246, Jul. 11, 2001, Office Action.
U.S. Appl. No. 08/883,246, Sep. 11, 2001, Notice of Allowance.
U.S. Appl. No. 09/057,108, Jul. 10, 2000, Office Action.
U.S. Appl. No. 09/057,108, Oct. 25, 2000, Notice of Allowance.
U.S. Appl. No. 09/262,402, Mar. 29, 2000, Office Action.
U.S. Appl. No. 09/262,402, May 30, 2000, Notice of Allowance.
U.S. Appl. No. 09/395,901, Jun. 27, 2000, Office Action.
U.S. Appl. No. 09/395,901, Nov. 6, 2000, Office Action.
U.S. Appl. No. 09/395,901, Apr. 20, 2001, Notice of Allowance.
U.S. Appl. No. 09/395,901, Sep. 10, 2001, Notice of Allowance.
U.S. Appl. No. 09/610,099, Jul. 11, 2002, Office Action.
U.S. Appl. No. 09/610,099, Dec. 24, 2002, Notice of Allowance.
U.S. Appl. No. 09/651,344, Feb. 28, 2003, Office Action.
U.S. Appl. No. 09/651,344, Nov. 7, 2003, Office Action.
U.S. Appl. No. 09/651,344, Apr. 20, 2004, Notice of Allowance.
U.S. Appl. No. 09/707,746, Feb. 16, 2005, Office Action.
U.S. Appl. No. 09/707,746, Jul. 7, 2005, Office Action.
U.S. Appl. No. 09/707,746, Nov. 15, 2005, Notice of Allowance.
U.S. Appl. No. 09/769,109, Oct. 23, 2001, Office Action.
U.S. Appl. No. 09/769,109, Jun. 17, 2002, Office Action.
U.S. Appl. No. 09/769,109, Sep. 9, 2002, Notice of Allowance.
U.S. Appl. No. 09/988,541, Mar. 17, 2004, Office Action.
U.S. Appl. No. 09/988,541, Feb. 28, 2005, Office Action.
U.S. Appl. No. 09/988,541, May 25, 2005, Office Action.
U.S. Appl. No. 09/988,541, Aug. 24, 2005, Office Action.
U.S. Appl. No. 09/988,541, Nov. 8, 2005, Office Action.
U.S. Appl. No. 09/988,541, Dec. 13, 2005, Notice of Allowance.
U.S. Appl. No. 10/033,689, Sep. 30, 2003, Office Action.
U.S. Appl. No. 10/152,272, Jan. 24, 2005, Office Action.
U.S. Appl. No. 10/152,272, May 13, 2005, Notice of Allowance.
U.S. Appl. No. 10/335,065, Mar. 17, 2005, Office Action.
U.S. Appl. No. 10/335,065, Jun. 10, 2005, Office Action.
U.S. Appl. No. 10/335,065, Nov. 17, 2005, Notice of Allowance.
U.S. Appl. No. 10/335,147, Dec. 13, 2005, Office Action.
U.S. Appl. No. 10/335,147, Apr. 17, 2006, Office Action.
U.S. Appl. No. 10/335,147, Oct. 4, 2006, Notice of Allowance.
U.S. Appl. No. 10/357,984, Jan. 9, 2006, Office Action.
U.S. Appl. No. 10/357,984, Mar. 16, 2006, Office Action.
U.S. Appl. No. 10/357,984, Sep. 28, 2006, Office Action.
U.S. Appl. No. 10/357,984, Mar. 23, 2007, Office Action.
U.S. Appl. No. 10/357,984, Nov. 14, 2007, Office Action.
U.S. Appl. No. 10/652,182, Aug. 9, 2006, Office Action.
U.S. Appl. No. 10/652,182, Feb. 22, 2007, Notice of Allowance.
U.S. Appl. No. 10/660,288, Nov. 15, 2005, Office Action.
U.S. Appl. No. 10/660,288, Mar. 9, 2006, Office Action.
U.S. Appl. No. 10/660,288, Aug. 24, 2006, Office Action.
U.S. Appl. No. 10/660,288, Feb. 1, 2007, Office Action.
U.S. Appl. No. 10/660,288, Jun. 28, 2007, Office Action.
U.S. Appl. No. 10/660,288, Apr. 29, 2009, Office Action.
U.S. Appl. No. 10/660,288, Aug. 3, 2009, Office Action.
U.S. Appl. No. 10/660,288, Mar. 30, 2010, Office Action.
U.S. Appl. No. 10/660,288, Mar. 29, 2011, Office Action.
U.S. Appl. No. 10/660,288, Sep. 30, 2011, Notice of Allowance.
U.S. Appl. No. 10/729,541, Dec. 12, 2006, Office Action.
U.S. Appl. No. 10/729,541, Jun. 18, 2007, Office Action.
U.S. Appl. No. 10/729,541, Jan. 8, 2008, Office Action.
U.S. Appl. No. 10/729,541, Sep. 23, 2008, Office Action.
U.S. Appl. No. 10/729,541, May 1, 2009, Office Action.
U.S. Appl. No. 10/729,541, Nov. 16, 2009, Notice of Allowance.
U.S. Appl. No. 10/729,541, Mar. 25, 2010, Notice of Allowance.
U.S. Appl. No. 10/729,541, Jul. 12, 2010, Notice of Allowance.
U.S. Appl. No. 10/737,668, Nov. 2, 2005, Office Action.
U.S. Appl. No. 10/737,668, Feb. 16, 2006, Office Action.
U.S. Appl. No. 10/737,668, Oct. 19, 2006, Office Action.
U.S. Appl. No. 10/737,668, Jun. 7, 2007, Office Action.
U.S. Appl. No. 10/737,668, Nov. 28, 2007, Office Action.
U.S. Appl. No. 10/737,668, Jun. 26, 2008, Notice of Allowance.
U.S. Appl. No. 10/742,406, Mar. 23, 2007, Office Action.
U.S. Appl. No. 10/742,406, Sep. 10, 2007, Notice of Allowance.
U.S. Appl. No. 10/742,406, Jan. 11, 2008, Notice of Allowance.
U.S. Appl. No. 10/746,210, Apr. 5, 2007, Office Action.
U.S. Appl. No. 10/746,210, Aug. 21, 2007, Office Action.
U.S. Appl. No. 10/746,210, Jul. 9, 2008, Notice of Allowance.
U.S. Appl. No. 10/813,449, Sep. 5, 2006, Office Action.
U.S. Appl. No. 10/813,449, Jul. 16, 2007, Office Action.

(56) References Cited

OTHER PUBLICATIONS

U.S. Appl. No. 10/813,449, Jan. 25, 2008, Office Action.
U.S. Appl. No. 10/813,449, Aug. 14, 2008, Office Action.
U.S. Appl. No. 10/813,449, Sep. 15, 2008, Office Action.
U.S. Appl. No. 10/813,449, Feb. 3, 2009, Office Action.
U.S. Appl. No. 10/813,449, Aug. 28, 2009, Office Action.
U.S. Appl. No. 10/813,449, May 27, 2010, Office Action.
U.S. Appl. No. 10/909,531, Apr. 4, 2007, Office Action.
U.S. Appl. No. 10/909,531, Dec. 26, 2007, Office Action.
U.S. Appl. No. 10/909,531, Jun. 13, 2008, Office Action.
U.S. Appl. No. 10/909,53,1 Feb. 9, 2009, Office Action.
U.S. Appl. No. 10/909,531, Sep. 16, 2009, Office Action.
U.S. Appl. No. 10/909,531, Apr. 29, 2010, Notice of Allowance.
U.S. Appl. No. 10/909,531, Aug. 20, 2010, Notice of Allowance.
U.S. Appl. No. 10/948,445, Jul. 11, 2007, Office Action.
U.S. Appl. No. 11/199,338, Jan. 25, 2007, Office Action.
U.S. Appl. No. 11/199,338, Oct. 5, 2007, Office Action.
U.S. Appl. No. 11/199,338, Dec. 28, 2007, Office Action.
U.S. Appl. No. 11/199,338, Apr. 23, 2008, Office Action.
U.S. Appl. No. 11/199,338, Jan. 6, 2009, Office Action.
U.S. Appl. No. 11/199,496, Apr. 1, 2009, Office Action.
U.S. Appl. No. 11/199,496, Aug. 21, 2009, Office Action.
U.S. Appl. No. 11/199,496, Apr. 23, 2010, Office Action.
U.S. Appl. No. 11/199,496, Apr. 28, 2011, Office Action.
U.S. Appl. No. 11/199,496, Aug. 18, 2011, Notice of Allowance.
U.S. Appl. No. 11/199,515, Aug. 20, 2008, Office Action.
U.S. Appl. No. 11/199,515, Nov. 13, 2008, Office Action.
U.S. Appl. No. 11/199,515, Jun. 10, 2009, Office Action.
U.S. Appl. No. 11/199,515, Dec. 24, 2009, Notice of Allowance.
U.S. Appl. No. 11/199,515, Apr. 2, 2007, Notice of Allowance.
U.S. Appl. No. 11/199,515, Aug. 2, 2010, Notice of Allowance.
U.S. Appl. No. 11/273,107, Jun. 14, 2007, Office Action.
U.S. Appl. No. 11/273,107, Jan. 18, 2008, Office Action.
U.S. Appl. No. 11/273,107, Sep. 5, 2008, Office Action.
U.S. Appl. No. 11/273,107, Apr. 9, 2009, Office Action.
U.S. Appl. No. 11/273.107, Oct. 28, 2009, Office Action.
U.S. Appl. No. 11/273,107, Jun. 2, 2010, Office Action.
U.S. Appl. No. 11/273,107, Oct. 27, 2010, Office Action.
U.S. Appl. No. 11/273,107, Jun. 2, 2011, Notice of Allowance.
U.S. Appl. No. 11/363,005, Jun. 22, 2007, Office Action.
U.S. Appl. No. 11/363,005, Dec. 14, 2007, Office Action.
U.S. Appl. No. 11/363,005, Apr. 17, 2008, Office Action.
U.S. Appl. No. 11/363,005, Dec. 23, 2008, Office Action.
U.S. Appl. No. 11/363,005, Jul. 10, 2009, Notice of Allowance.
U.S. Appl. No. 11/363,005, Jan. 14, 2010, Notice of Allowance.
U.S. Appl. No. 11/363,005, Jul. 23, 2010, Notice of Allowance.
U.S. Appl. No. 11/389,762, Sep. 20, 2007, Notice of Allowance.
U.S. Appl. No. 11/389,762, Nov. 23, 2007, Notice of Allowance.
U.S. Appl. No. 11/390,937, Sep. 7, 2007, Office Action.
U.S. Appl. No. 11/391,951, Oct. 28, 2008, Office Action.
U.S. Appl. No. 11/391,951, Jan. 30, 2009, Office Action.
U.S. Appl. No. 11/391,951, Aug. 26, 2009, Office Action.
U.S. Appl. No. 11/391,951, Jun. 23, 2010, Office Action.
U.S. Appl. No. 11/465,527, Feb. 3, 2010, Office Action.
U.S. Appl. No. 11/465,527, Jul. 23, 2010, Notice of Allowance.
U.S. Appl. No. 11/552,593, Aug. 21, 2008, Office Action.
U.S. Appl. No. 11/552,593, Feb. 5, 2009, Office Action.
U.S. Appl. No. 11/552,593, Oct. 13, 2009, Notice of Allowance.
U.S. Appl. No. 11/552,593, Mar. 22, 2010, Notice of Allowance.
U.S. Appl. No. 11/552,593, Jul. 22, 2010, Notice of Allowance.
U.S. Appl. No. 11/688,722, Mar. 10, 2010, Office Action.
U.S. Appl. No. 11/688,722, Jul. 29, 2010, Notice of Allowance.
U.S. Appl. No. 11/891,358, Apr. 26, 2010, Office Action.
U.S. Appl. No. 11/891,358, Oct. 19, 2010, Office Action.
U.S. Appl. No. 11/891,358, Aug. 31, 2011, Office Action.
U.S. Appl. No. 11/891,358, Nov. 18, 2011, Notice of Allowance.
U.S. Appl. No. 11/891,358, Apr. 10, 2012, Notice of Allowance.
U.S. Appl. No. 11/891,513, Apr. 9, 2010, Office Action.
U.S. Appl. No. 11/891,513, Sep. 28, 2010, Office Action.
U.S. Appl. No. 11/891,513, Aug. 31, 2011, Office Action.
U.S. Appl. No. 11/891,513, Nov. 1, 2011, Notice of Allowance.
U.S. Appl. No. 11/891,513, May 8, 2012, Notice of Allowance.
U.S. Appl. No. 11/960,593, Sep. 14, 2010, Office Action.
U.S. Appl. No. 11/960,593, Nov. 3, 2010, Office Action.
U.S. Appl. No. 11/960,593, Apr. 28, 2011, Office Action.
U.S. Appl. No. 11/997,379, Jul. 13, 2011, Office Action.
U.S. Appl. No. 11/997,379, Feb. 28, 2012, Office Action.
U.S. Appl. No. 11/997,379, May 11, 2012, Notice of Allowance.
U.S. Appl. No. 12/182,836, Oct. 5, 2010, Office Action.
U.S. Appl. No. 12/182,836, Jun. 23, 2011, Office Action.
U.S. Appl. No. 12/247,012, Oct. 13, 2011, Office Action.
U.S. Appl. No. 12/247,012, Mar. 16, 2012, Office Action.
U.S. Appl. No. 12/247,012, Aug. 13, 2012, Notice of Allowance.
U.S. Appl. No. 12/247,012, Mar. 27, 2013, Issue Notification.
U.S. Appl. No. 12/257,127, Aug. 30, 2010, Office Action.
U.S. Appl. No. 12/257,127, Dec. 22, 2010, Office Action.
U.S. Appl. No. 12/257,127, Jul. 6, 2011, Office Action.
U.S. Appl. No. 12/257,127, Jan. 12, 2012, Office Action.
U.S. Appl. No. 12/257,127, Sep. 20, 2012, Notice of Allowance.
U.S. Appl. No. 12/334,077, Oct. 27, 2010, Office Action.
U.S. Appl. No. 12/334,077, Jul. 21, 2011, Office Action.
U.S. Appl. No. 12/334,077, Jan. 16, 2013, Office Action.
U.S. Appl. No. 12/334,085, Dec. 23, 2010, Office Action.
U.S. Appl. No. 12/334,085, Aug. 4, 2011, Office Action.
U.S. Appl. No. 12/334,085, Jan. 9, 2012, Notice of Allowance.
U.S. Appl. No. 12/873,728, Sep. 11, 2012, Office Action.
U.S. Appl. No. 12/950,338, Jun. 15, 2011, Office Action.
U.S. Appl. No. 12/950,338, Nov. 1, 2011, Notice of Allowance.
U.S. Appl. No. 12/950,338, Aug. 8, 2012, Notice of Allowance.
U.S. Appl. No. 12/955,848, Jun. 30, 2011, Office Action.
U.S. Appl. No. 12/955,848, Nov. 15, 2011, Office Action.
U.S. Appl. No. 12/955,863, Jan. 6, 2012, Office Action.
U.S. Appl. No. 12/955,863, May 15, 2012, Notice of Allowance.
U.S. Appl. No. 12/955,869, Oct. 18, 2011, Office Action.
U.S. Appl. No. 12/955,869, Mar. 22, 2012, Notice of Allowance.
U.S. Appl. No. 12/961,239, Jul. 26, 2011, Notice of Allowance.
U.S. Appl. No. 12/966,961, Aug. 18, 2011, Notice of Allowance.
U.S. Appl. No. 13/022,050, Jul. 11, 2011, Office Action.
U.S. Appl. No. 13/022,050, Apr. 26, 2012, Office Action.
U.S. Appl. No. 13/022,050, Jul. 6, 2012, Notice of Allowance.
U.S. Appl. No. 13/593,154, Jan. 8, 2013, Notice of Allowance.
U.S. Appl. No. 13/615,530, Jan. 17, 2013, Office Action.
U.S. Appl. No. 90/006,469, Nov. 29, 2002, Request for Re-Examination.
U.S. Appl. No. 90/006,469, Sep. 10, 2004, Office Action.
U.S. Appl. No. 90/006,469, Sep. 27, 2005, Notice of Re-Issue.
U.S. Appl. No. 90/006,469, Jun. 27, 2006, Re-Examination Certification.
U.S. Appl. No. 13/870,628, filed Apr. 25, 2013, Ma.
U.S. Appl. No. 12/873,728, May 3, 2013, Office Action.
U.S. Appl. No. 14/674,756, filed Apr. 2, 2015, Voss.
Definition of "pair", Dictionary.com, accessed on May 5, 2014.
U.S. Appl. No. 12/334,077, Oct. 11, 2013, Notice of Allowance.
U.S. Appl. No. 12/873,728, Aug. 23, 2013, Office Action.
U.S. Appl. No. 12/873,728, Nov. 4, 2013, Notice of Allowance.
U.S. Appl. No. 13/333,411, Dec. 18, 2014, Office Action.
U.S. Appl. No. 13/333,411, Apr. 1, 2015, Office Action.
U.S. Appl. No. 13/443,659, Nov. 13, 2013, Office Action.
U.S. Appl. No. 13/443,659, Jun. 11, 2014, Notice of Allowance.
U.S. Appl. No. 13/455,053, Nov. 27, 2013, Office Action.
U.S. Appl. No. 13/455,053, Jun. 9, 2014, Notice of Allowance.
U.S. Appl. No. 13/525,875, May 28, 2014, Office Action.
U.S. Appl. No. 13/525,875, Sep. 30, 2014, Office Action.
U.S. Appl. No. 13/525,875, Dec. 10, 2014, Notice of Allowance.
U.S. Appl. No. 13/525,875, Mar. 18, 2015, Issue Notification.
U.S. Appl. No. 13/752,095, Oct. 17, 2014, Office Action.
U.S. Appl. No. 13/752,095, Feb. 20, 2015, Office Action.
U.S. Appl. No. 14/094,352, Dec. 15, 2014, Office Action.
U.S. Appl. No. 14/195,308, Dec. 18, 2014, Office Action.
U.S. Appl. No. 13/593,154, Apr. 10, 2013, Issue Notification.
U.S. Appl. No. 13/485,388, Oct. 7, 2015, Notice of Allowance.
U.S. Appl. No. 13/870,628, Jul. 13, 2015, Office Action.

(56) References Cited

OTHER PUBLICATIONS

U.S. Appl. No. 14/195,308, Aug. 11, 2015, Office Action.
U.S. Appl. No. 14/880,894, filed Oct. 12, 2015, McIntosh.
U.S. Appl. No. 13/870,628, Nov. 12, 2015, Notice of Allowance.
U.S. Appl. No. 14/195,308, Dec. 4, 2015, Notice of Allowance.
U.S. Appl. No. 13/615,523, Feb. 26, 2016, Office Action.
U.S. Appl. No. 14/094,352, Mar. 22, 2016, Notice of Allowance.
U.S. Appl. No. 14/195,308, Mar. 16, 2016, Issue Notification.

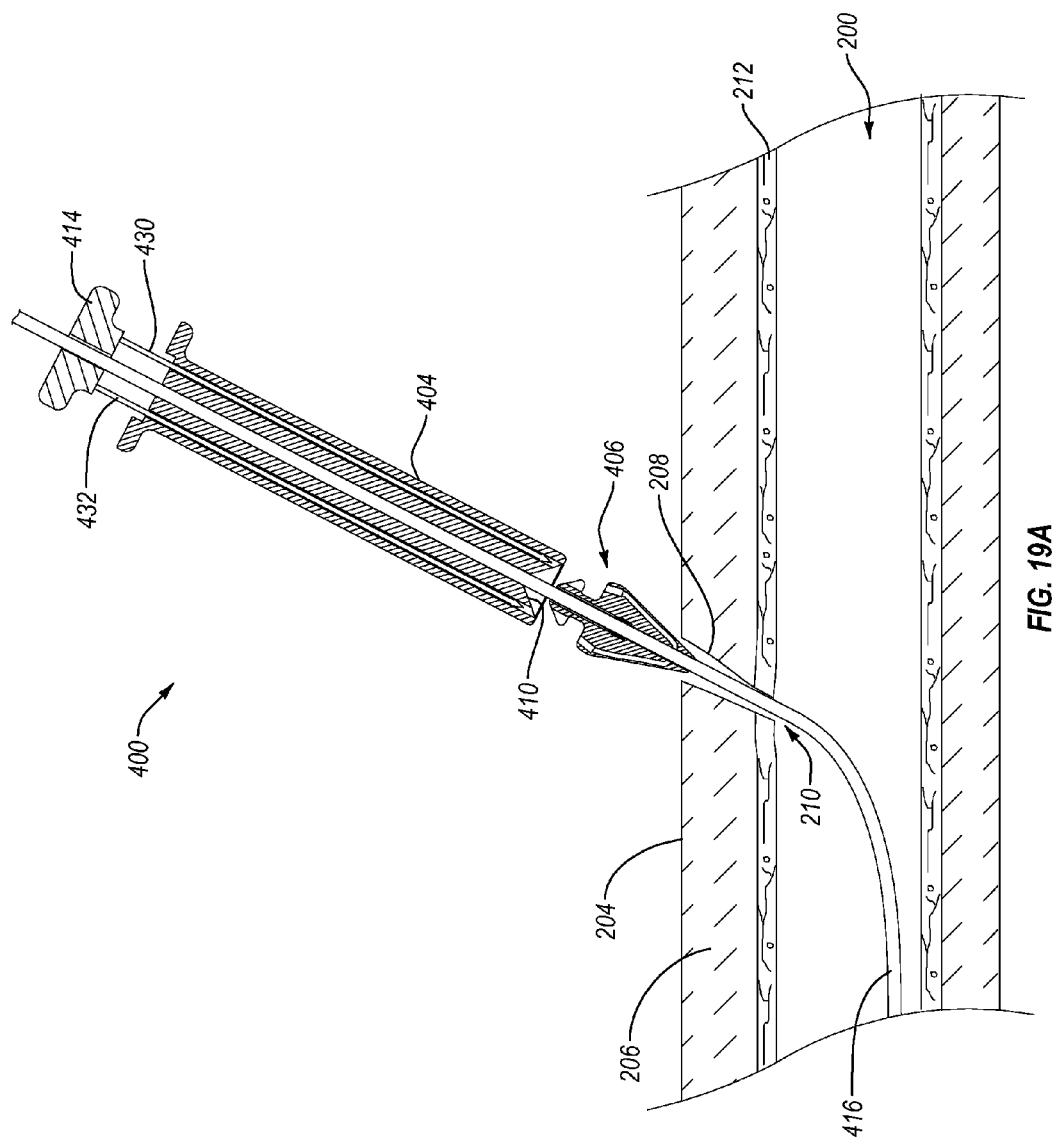

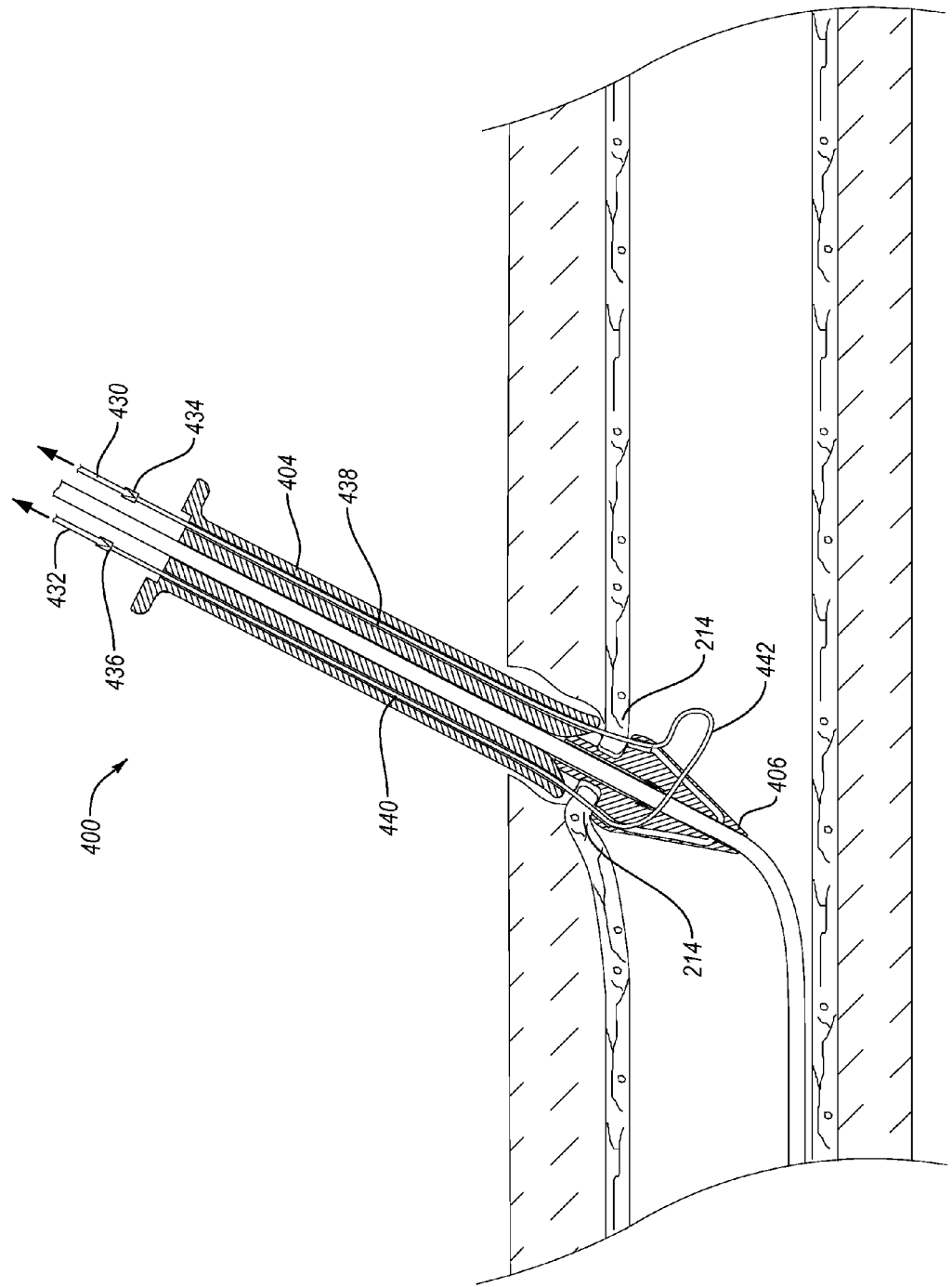

SUTURING DEVICES AND METHODS

CROSS-REFERENCE TO RELATED APPLICATIONS

This application is a continuation-in-part of an earlier filed U.S. patent application Ser. No. 12/873,728, filed Sep. 1, 2010, now U.S. Pat. No. 8,663,252, entitled "Suturing Devices And Methods," the entire content of which is incorporated by reference herein.

FIELD OF THE INVENTION

The present invention relates generally to medical devices, systems, and methods. In particular, the present disclosure relates to devices and methods for suturing of openings in body lumens. More specifically, the present invention relates to devices and methods for closing arterial and venous puncture sites.

BACKGROUND OF THE INVENTION

Catheterization and interventional procedures, such as, for example, angioplasty, catheterization, and the placement of stents, are commonly performed by inserting a hollow needle through the skin and tissue of a patient into the patient's vascular system. A guide wire is then often advanced through the needle and into the patient's blood vessel. The needle is then removed, enabling an introducer sheath to be advanced over the guidewire into the vessel, e.g., in conjunction with, or subsequent to, a dilator. A catheter or other device may then be advanced through a lumen of the introducer sheath and over the guidewire into a position for performing a medical procedure. Thus, the introducer sheath may facilitate introducing various devices into the vessel, while minimizing trauma to the vessel wall and/or minimizing blood loss during a procedure.

In practice, the introducer sheath is often inserted into the patient's vasculature using the modified Seldinger technique. In the Seldinger technique, a needle is first inserted into the vessel and a guide wire then follows through the needle. Next, the needle is removed and a sheath/dilator combination is advanced over the guide wire. The dilator expands the puncture in the vessel to a size suitable to receive the distal end of an introducer sheath. After the distal end of the sheath is disposed within the vessel, the dilator and guide wire are removed, thereby allowing access to the vessel lumen or other body lumen via the inserted introducer sheath.

Upon completing the diagnostic and/or treatment procedure, the devices and introducer sheath are removed, leaving a puncture site in the vessel wall. One will appreciate that it is desirable to close the puncture site in vessel wall. Closing the wound can be difficult due to substantial bleeding that can occur through an open wound in a blood vessel. One method of closing the puncture site includes applying external pressure to the puncture site until clotting and wound sealing occur; however, the patient must remain bedridden for a substantial period after clotting to ensure closure of the wound. This procedure can be time consuming and expensive, requiring as much as an hour of a physician's or nurse's time. It also can be uncomfortable for the patient and may require that the patient remain immobilized in the operating room, catheter lab, or holding area. In addition, a risk of hematoma exists from bleeding before hemostasis occurs.

Another method of puncture site closure is the use of bioabsorbable fasteners or sealing plugs. Bioabsorbable fasteners or sealing plugs can overcome many of the disadvantages associated with manual compression. Typically, these approaches rely on the placement of a thrombogenic and bioabsorbable material, such as collagen, at the superficial arterial wall over the puncture site. While potentially effective, this approach can suffer from a number of disadvantages. For example, it can be difficult to properly locate the interface of the overlying tissue and the adventitial surface of the blood vessel. Placing the plug too far from that interface can result in failure to provide hemostasis, and subsequent hematoma and/or pseudo-aneurysm formation. Conversely, if the plug intrudes into the artificial lumen, intravascular clots and/or collagen pieces with thrombus attached can form and embolize downstream, causing vascular occlusion. Also, thrombus formation on the surface of a plug protruding into the lumen can cause a stenosis, which can obstruct normal blood flow. Other possible complications include infection, as well as adverse reaction to the collagen or other implant.

Yet another approach for vascular closure includes the use of suture-applying devices. Conventional suture-applying devices are introduced through the tissue tract and advanced until a distal end of the device extends through the puncture site. One or more needles in the device are then deployed and used to draw suture through the blood vessel wall. Next, the suture is secured to provide closure of the puncture site. While suture-applying devices can overcome many of the difficulties associated with other puncture site closure devices and methods, locating the tissue surrounding a puncture site can be difficult using some suture-applying devices and methods. Some complications that may arise by misplaced or insufficiently anchored sutures include oozing, excessive bleeding, and potential knot loosening.

BRIEF SUMMARY

Briefly summarized, implementations of the present invention provide devices and methods for closing openings in a body lumen efficiently and quickly. For example, one or more implementations of the present invention provide suturing devices with tissue ports configured to allow for location of body lumen wall tissue surrounding a puncture site with increased accuracy and ease. This method can provide for suture deployment over the guide wire permitting rapid re-access to the vessel by the clinician. Furthermore, one or more implementations of the present invention can reduce miss-deployment of needles, and can allow for closure of larger body lumen openings.

For example, in one implementation, a suturing device configured to close an opening in a body lumen can include a shaft having a distal end and a proximal end. The distal end of the shaft can be defined by the distal most surface of the shaft. The shaft can include a first needle exit opening extending through the distal end thereof. The shaft can further include a second needle exit opening extending through the distal end thereof. The suturing device can further include a foot member secured to the distal end of the shaft. Additionally, the suturing device can include first and second needle capture devices removably secured to the foot member. The suturing device can also include at least one length of suture removably secured to the foot member. The at least one length of suture can have a first end secured to the first needle capture device and a second end secured to the second needle capture device.

In another implementation, a suturing device configured to close an opening in a body lumen can include a shaft having a distal end and a proximal end. The suturing device can also include a foot having a proximal tissue location surface and a distal tip. Additionally, the suturing device can include a spinal member connecting the foot member to the shaft. Also, the suturing device can include an actuator configured to move the foot from a first configuration, in which the tissue location surface is adjacent the distal end of the shaft, to a deployed configuration, in which the tissue location surface is distally separated from the distal end of the shaft by a length of the spinal member.

In yet another implementation, a suturing device configured to close an opening in a body lumen can include an elongate member including a proximal portion and a distal portion. The suturing device can also include first and second needle lumens extending through the proximal portion of the elongate member to first and second needle exit openings. Furthermore, the suturing device can include first and second needle capture devices secured to the distal portion of the elongate member. The first and second needle capture devices can be aligned with the first and second needle exit openings. Additionally, the first and second needle capture devices can be separated from the first and second needle exit openings by one or more tissue ports extending into the elongate member between the proximal portion and the distal portion. The suturing device can also include at least one length of suture within the distal portion of the shaft. The at least one length of suture can have a first end secured to the first needle capture device and a second end secured to the second needle capture device.

In addition to the foregoing, an implementation of a method of closing an opening in a body lumen wall can involve advancing a suturing device over a guidewire into the body lumen. The suturing device can include a shaft, a foot secured to a distal end of the shaft, and at least one tissue port located between the distal end of the shaft and the foot. The method can also involve advancing a pair of needles simultaneously through the shaft, out of needle exit openings in the distal end of the shaft, through wall tissue of the body lumen located in at least one tissue port, and into a pair of needle capture devices secured to the foot. Additionally, the method can involve withdrawing the pair of needles and the pair of needle capture devices from the suturing device, thereby at least partially withdrawing a suture connected to the pair of needle capture devices from the foot. Further, the method can involve employing the suture to close the opening in the body lumen wall.

Another implementation of a method of closing an opening in a body lumen wall can involve advancing a suturing device into the opening of the body lumen wall. The suturing device can include a shaft and a foot secured to a distal end of the shaft. The method can further involve articulating the foot from a first configuration in which the foot is adjacent a distal end of the shaft to a deployed configuration in which the foot is distally separated from the distal end of the shaft. The method can also involve advancing one or more needles through the shaft, through wall tissue of the body lumen located in between the shaft and the foot, and into one or more needle capture devices secured to the foot. The method can additionally involve employing the suture to close the opening in the body lumen wall.

One implementation includes a suturing device configured to close an opening in a body lumen. The suturing device may have a shaft having a distal end and a proximal end. Additionally, the suturing device can include a first needle lumen disposed within the shaft, the first needle lumen terminating at a first needle exit opening at the distal end of the shaft and a second needle lumen disposed within the shaft, the second needle lumen terminating at a second needle exit opening at the distal end of the shaft. The suturing device also can include a guide member slidably located within the shaft and extending past the distal end of the shaft and a foot member coupled to the guide member, a proximal end of the foot member being positioned proximally to the distal end of the shaft. Furthermore, the suturing device can include a first needle capture device removably secured to the foot member and a second needle capture device removably secured to the foot member. The suturing device also can incorporate at least one length of suture removably secured to the foot member, the at least one length of suture having a first end secured to the first needle capture device and a second end secured to the second needle capture device.

One or more other implementations include a suturing device configured to close an opening in a body lumen. The suturing device can have a shaft having a distal end and a proximal end, a first needle lumen disposed within the shaft, the first needle lumen terminating at a first needle entrance opening at the distal end of the shaft, and a second needle lumen disposed within the shaft, the second needle lumen terminating at a second needle entrance opening at the distal end of the shaft. The suturing device also can include a guide member slidably positioned within the shaft and extending past the distal end of the shaft, the guide member having a first needle and a second needle, the first and second needles having piercing ends oriented in a proximal direction. Moreover, the suturing device can include a cable connected to the first and second needles, the cable being configured to move the needles in the proximal direction and a length of suture having a first and second ends thereof secured to the first and second needles. Additionally or alternatively, the suturing device can include a foot coupled to the guide member, the foot having a first needle connector lumen and a second needle connector lumen, the first and second needle connector lumens being configured to guide the first and second needles out of the guide member and into the first and second entrance openings in the shaft.

Implementations of the present invention also include a method of closing an opening in a body lumen. The method can have various acts, which can include but are not limited to inserting a guide member of a suturing device through the opening and into the body lumen and inserting a foot of the suturing device into the opening and capturing tissue surrounding the opening in one or more tissue ports of the foot. Additionally, the method can include an act of adjusting a shaft of the suturing device in a manner that needle exit openings located in the shaft correspond with needle capture devices located in the foot. Furthermore, the method can include an act of passing a plurality of needles through the shaft, out of the needle exit openings, through the tissue surrounding the opening, and into corresponding needle capture devices. The method also can include an act of retrieving the plurality of needles together with the corresponding needle capture devices, thereby passing a length of suture attached to the needle capture devices through the tissue surrounding the opening.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. Understanding that these drawings depict only typical embodiments of the invention and are not therefore to be considered to be limiting of its scope, the invention will be described and explained with additional specificity and detail through the use of the accompanying drawings in which:

FIGS. 19A-19F illustrate cross-sectional views of a body lumen, showing a method for closing an opening in the wall of the body lumen using the suturing device of FIG. 14.

DETAILED DESCRIPTION

Figure 1:
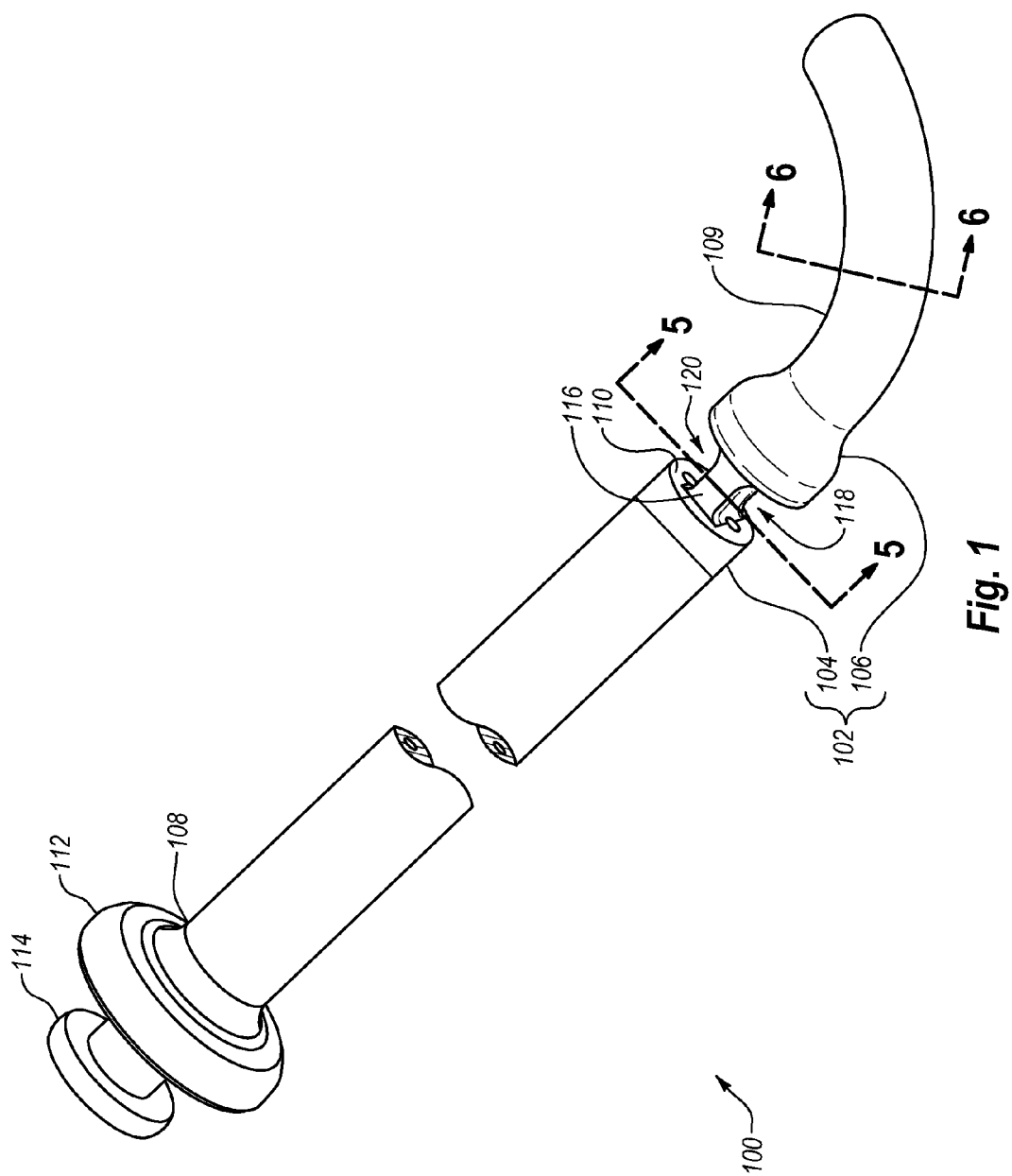
FIG. 1 illustrates a perspective view of a suturing device with a passive foot in accordance with an implementation of the present invention.

As previously mentioned, implementations of the present invention include devices and methods for closing openings in a body lumen efficiently and quickly. For example, one or more implementations of the present invention provide suturing devices with tissue ports configured to allow for location of body lumen wall tissue surrounding a puncture site with increased accuracy and ease. This method can provide for suture deployment over the guide wire permitting rapid re-access to the vessel by the clinician. Furthermore, one or more implementations of the present invention can reduce miss-deployment of needles, and can allow for closure of larger body lumen openings.

In particular, one implementation of the present invention can include a suturing device having a body including a shaft and a foot for insertion into an opening in a body lumen. The body can include tissue ports between the shaft and the foot configured to receive tissue of the body lumen surrounding the opening. The foot can include a suture secured to needle capture devices. Needles can be advanced within the shaft, through tissue within the tissue ports, and into the needle capture devices. The needle capture devices can then be withdrawn, thereby harvesting the suture, which can then be used to close the opening in the body lumen.

In some implementations of the present invention, the tissue ports in the body of the suturing device can be passive. In other words, the tissue ports can be formed between the shaft and the foot and remain open at all times. In alternative implementations, the tissue ports can be non-passive. In such implementations, the foot can articulate between a pre-deployed configuration and deployed configuration. In the pre-deployed configuration the tissue ports can be at least partially closed. For example, in one implementation the foot can abut against the shaft when in the pre-deployed configuration. In the deployed configuration the tissue ports can be open. For example, in one implementation the foot can be distally displaced from the foot when in the deployed configuration, thereby opening tissue ports between the foot and the shaft. In implementations including an articulating foot, the foot can be used to draw or push tissue surrounding an opening in a body lumen into the tissue ports.

Additionally, one or more implementations of the present invention include devices and procedures that allow a medical practitioner to insert a first suturing device over a guidewire into a tissue opening, deploy at least one suture, and remove the suturing device from the tissue opening before removing the guidewire. One will appreciate that this can allow the medical practitioner to run an additional suturing device over the same guidewire if the medical practitioner is not able to close the tissue opening using the first suturing device. For example, if needles used to harvest the suture of the first suturing device miss-deploy or otherwise fail to harvest the suture, the medical practitioner can remove the first suturing device and deploy another without having to place a second guidewire.

As an initial matter, as used herein, the term "proximal" refers to a direction toward a user (i.e., a medical practitioner or surgeon) of a suturing device and away from the patient, or a location closer to the user of the suturing device. As used herein, the term "distal" refers to a direction towards the patient and away from the user of the suturing device, or a location closer to the patient.

Turning now to the Figures, FIG. 1 shows an implementation of a suturing device 100 for closing an incision, a puncture, a passage, or opening through tissue or a body lumen. In particular, the implementation shown by Figure in is a suturing device 100 that includes passive tissue ports. In some examples, the suturing device 100 can close communication with a blood vessel or other body lumen. As shown in FIG. 1, the suturing device 100 can include a body or elongate member 102. The body 102 can have an annular configuration positioned about a central axis. For example, the body 102 illustrated in FIG. 1 includes a circular cross-section. In additional implementations, the body 102 may include other non-circular shapes as well, such as elliptical or other symmetrical or non-symmetrical shapes.

In any event, the body 102 can include a proximal portion or shaft 104 and a distal portion or foot 106. FIG. 1 further illustrates that the suturing device 100 can include a flexible, guidebody 109 extending distally from the distal end of the foot 106. As explained in greater detail below, the guidebody 109 can be advanced along a guidewire into a body lumen. Thus, at least the distal portion of the guidebody 109 can be formed from a flexible or elastomeric material that is biocompatible, particularly with blood. For example, in some implementations the guidebody 109 can be composed of a biocompatible polymeric material, such as, for example, silicone rubber, polyolefin, polyurethane, polytetrafluoroethylene, nylon, pebax, KYNAR, or similar materials. In additional implementations, the guidebody can be coated or impregnated with a lubricant, bioactive agent, such as an anticoagulant material, Polyvinylpyrrolidone (PVP), or the like. For example, the bioactive agent may have any therapeutic effect. Examples of additional suitable therapeutic properties may include anti-proliferative, anti-inflammatory, antiplatelet, anti-fibrin, antithrombotic, antimitotic, antibiotic, antiallergic, antioxidant properties, and/or other therapeutic properties.

For example, a bioactive agent may be used to reduce scar tissue response when after the guidebody is withdrawn from the tissue of a body lumen. Reducing scar tissue response, structural tissue response, restenosis, and/or thrombosis may facilitate access to the tissue after the opening has been sutured. For example, if a device did not use a beneficial agent to reduce scar tissue response, structural tissue response, restenosis, and/or thrombosis after deployment, these and/or other tissue responses may hinder future access to the tissue.

The foot 106 can include a flared portion that extends radially outward of the guidebody 109 and/or shaft 104. The foot 106 may be machined or cast from a composite material, such as, for example, carbon fiber. In some implementations, the foot 106 can be molded as two separate halves which can be subsequently affixed together. In yet further implementations, the foot 106 may comprise a biocompatible material, such as, for example, stainless steel, nylon, or similar materials.

The shaft 104 can include a proximal end 108 and a distal end 110 (i.e., the terminal end or surface of the shaft 104). The shaft 104 can comprise a biocompatible material, such as stainless steel, carbon fiber, nylon, another suitable polymer, or similar materials. Furthermore, in some implementations the shaft 104 may be flexible to accommodate insertion into a body lumen. In alternative implementations, the shaft 104 may comprise a rigid construction so as to avoid substantial deflection during use.

A handle 112 can be secured to the proximal end 108 of the shaft 104. The handle 112 can be of sufficient dimensions to allow a medical practitioner to grasp the handle 112 and use it to manipulate the suturing device 100 during use. Furthermore, the handle 112 can support a needle actuation handle 114. The proportions of the needle actuation handle 114 and needles 122/124 may be change with respect to each other to improve needle stroke and column strength. The handle 112 and the needle actuation handle 114 may include a bioabsorbable metal, alloy, polymer, plastic, composite, other materials, or combinations thereof.

The handle 112 can have any number of suitable configurations. In some embodiments, the handle 112 can have a syringe grip configuration. For instance, the handle 112 can include opposing loops, which can accommodate user's fingers therein. Alternatively or additionally, the handle 112 can incorporate locations for user's fingers (e.g., the handle 112 can extend outward and bend away from the user). As such, the user can have a secure grip of the handle 112 as well as of the shaft 104.

The foot 106 can be secured to the distal end 110 of the shaft 104 by a spinal member 116. The spinal member 116 can separate the distal end 110 of the shaft 104 from the foot 106, and thus, define one or more tissue ports 118, 120. In some embodiments, the spinal member 116 comprises stainless steel, nitinol, or a similar material. The spinal member 116 can be composed of a biocompatible material that is substantially resistant to deformation, and therefore, can maintain alignment between the needle lumens 126, 128 and the needle capture devices 136, 138. It should be appreciated that the needle lumens 126, 128 can have any number of suitable configurations. For instance, the needle lumens 126, 168 can be substantially straight or linear. Alternatively, the needle lumens 126, 128 can be bent, angles, or may have any number of non-linear configurations. In any event, however, the needle lumens 126, 128 can be shaped, positioned, and oriented in a manner that allows the needles 122, 124 align with the needle capture devices 136, 138. One will appreciate that the spinal member's resistance to deformation can help ensure that needles 122, 124 are not miss-deployed. Furthermore, the spinal member can serve to maintain structural integrity between the shaft 104 and foot 106. Examples of suitable materials include stainless steel, polytetrafluoroethylene, nylon, polyamids, and similar materials.

Figure 5:
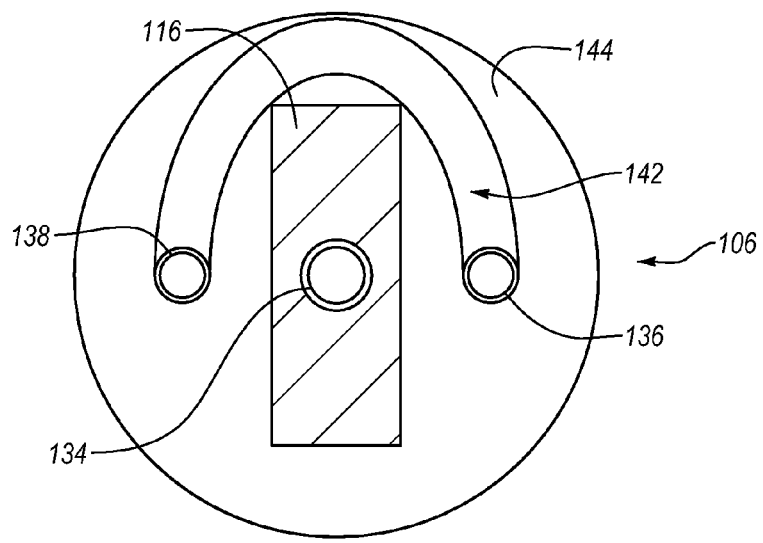
FIG. 5 illustrates a partial, cross-sectional view of the suturing device of FIG. 1 taken along the line 5-5 of FIG. 1.

Furthermore, FIG. 5 illustrates that the spinal member 116 can have a width equal to approximately the diameter of the foot 106. Thus, referring again to FIG. 1, the spinal member 116 can define two tissue ports 118, 120 separating the distal end 110 of the shaft 104 from the foot 106. In alternative implementations, the spinal member 116 can have a width smaller than the diameter of the shaft 104, and thus, define a single circumferential tissue port. Alternatively, the suturing device 100 can include three or more tissue ports.

In any event, the body 102 can include one or more tissue ports 118, 120 separating the distal end 110 of the shaft 104 from the foot 106. As explained in greater detail below, the tissue ports 118, 120 can be configured to receive tissue surrounding an opening, such as a puncture wound, in a body lumen wall. The tissue ports 118, 120 can thus help locate the tissue surrounding an opening, and allow for the suturing of the tissue to close the opening.

Figure 2:
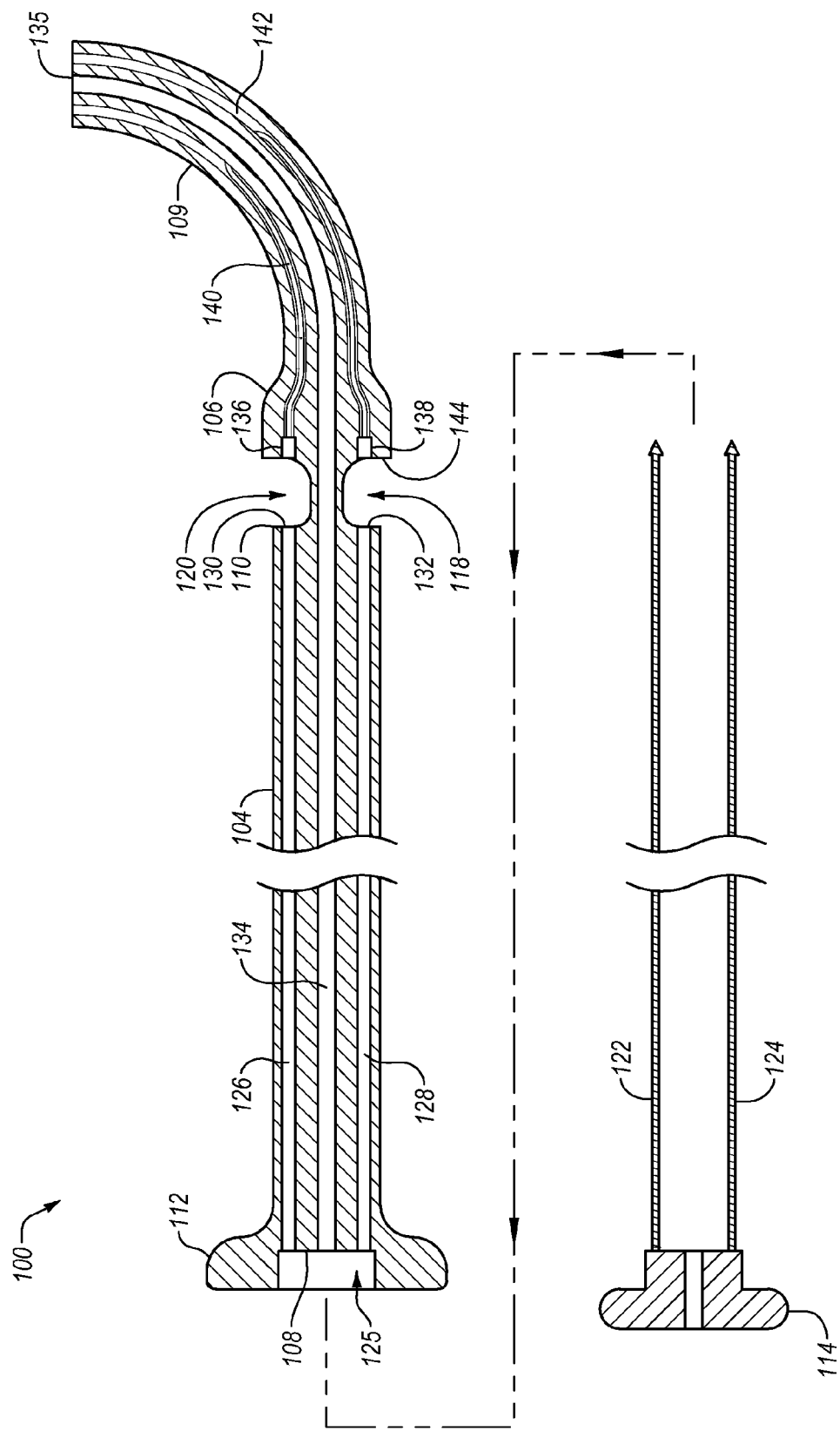
FIG. 2 illustrates an exploded, cross-sectional view of the suturing device of FIG. 1.
Figure 3:
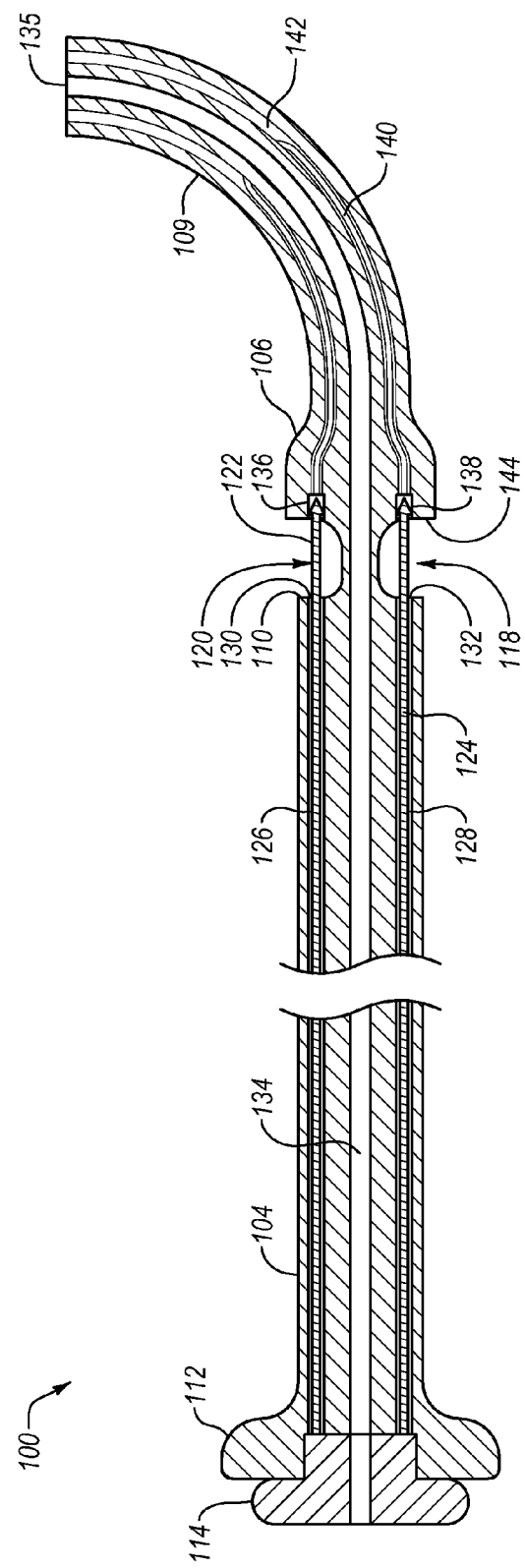
FIG. 3 illustrates a cross-sectional view of the suturing device of FIG. 1 with the needles thereof deployed.

Referring now to FIGS. 2 and 3, an exploded cross-sectional view and an assembled cross-sectional view, respectively, of the suturing device 100 are illustrated. As shown, the needle actuation handle 114 can include one or more needles secured thereto. In particular, the implementation shown in FIGS. 2 and 3 includes a first needle 122 and a second needle 124. In additional implementations, the suturing device 100 can include a single needle or three or more needles.

One or more of the needles for use with the suturing devices of the present invention can be provided as substantially described in U.S. Pat. No. 6,136,010 issued to Modesitt et al. and/or U.S. Pat. No. 5,792,152 issued to Klein et al., which are incorporated herein by reference in their entirety. As such in some implementations, the needles for use with the present invention can be flexible. Alternatively, needles for use with the present invention can be rigid. In particular, the needles can include sufficient column strength so as to avoid any meaningful deflection as they are advanced through tissue. By having a rigid construction, the needles can pass from the shaft 104, through tissue within the tissue ports 118, 120, and into the foot 106 without deflection. One will appreciate that this can help decrease or eliminate miss-deployment of needles sometimes associated with flexible needles. For example, a rigid construction can help ensure that the needles 122, 124 pass into the foot, instead of deflecting and missing the foot 106, or more specifically engagement features within the foot 106.

In any event, the needle actuation handle 114 can be engageable with or be secured to one or more needles. For example, FIG. 2 illustrates that the needle actuation handle 114 can be secured to the first needle 122 and the second needle 124. The needle actuation handle 114 can be sized to be positioned within a receptacle 125 extending into the proximal end 108 of the handle 112 and/or shaft 104. The needle actuation handle 114 can allow a medical practitioner to advance the needles 122, 124 into the shaft 104 and then the foot 106. Specifically, the needle actuation handle 114 can be configured such that a medical practitioner can advance the needles 122, 124 in a proximal direction toward the patient, and then subsequently in a distal direction away from the patient. In alternative implementations, the suturing device 100 may not include a needle actuation handle 114. In such implementations, the proximal ends of the needles 122, 124 can be configured to held and manipulated by the medical practitioner to advance and retract the needles 122, 124.

In some embodiments, the suturing device 100 can incorporate a spring, which can resist and/or prevent unintentional movement of the needle actuation handle 114. In other words, the spring may have to be compressed to advance the needle actuation handle 114. Accordingly, the spring may prevent unintentional engagement of the needles 122, 124 with the needle capture devices 136, 138.

FIGS. 2 and 3 illustrate that the shaft 104 of the body 102 can include a plurality of axial lumens therein. For example, FIGS. 2 and 3 illustrate that the shaft 104 can include a pair of needle lumens 126, 128. The needle lumens 126, 128 can extend from the proximal end 108 to the distal end 110 of the shaft 104. In particular, the distal end 110 end of the shaft 104 can include a first needle exit opening 130 and a second needle exit opening 132, at the respective ends of the needle lumens 126, 128. The needle lumen 126, 128 can guide the needles 122, 124 from the proximal end 108 of the shaft 104, through the shaft 104, and out of the needle exit openings 130, 132.

In addition to the needle lumens 122, 124, the shaft 104 can include additional lumens. For example, the shaft 104 can include a foot position verification lumen, such as that described herein below in reference to the suturing device 300 shown in FIGS. 10A-13I. Additionally, as shown in FIGS. 2 and 3, the shaft 104 can include a guidewire lumen 134. The guidewire lumen 134 can extend along the length of the shaft 104, through the foot 106, and through the guidebody 109. The guidewire lumen 134 can extend substantially along the central axis of the suturing device 100 as shown in FIGS. 2 and 3, or alternatively be offset from the central axis of the suturing device 100. Furthermore, in some implementations, the guidewire lumen 134 can serve as the spinal member 116.

The guidewire lumen 134 can receive or follow a guidewire left in place after a diagnostic or medical procedure. In particular, as explained in greater detail below, a medical practitioner can insert the suturing device 100 into a body lumen or other site to be repaired by sliding the guidewire lumen 134 over the pre-placed guidewire. For example, a medical practitioner can place an opening 135 in the distal end of the guidebody 109 over a guidewire (not shown). The guidewire can then extend through the guidewire lumen 134 and out of the needle actuation handle 114. Thus, the guidewire can extend out of the proximal end of the suturing device 100 without interfering with the needles 122, 124, needle lumens 126, 128, or suture. The guidewire can be removed after placement of the suturing device 100 in a body lumen, after deployment of the needles 126, 128, or after removal of the suturing device 100 from the patient, as considered prudent by the medical practitioner.

In addition to the guidewire lumen 134, the foot 106 can include one or more needle capture devices. For example, FIGS. 2 and 3 illustrate that the foot 106 can include a first needle capture device 136 and a second needle capture device 138. In alternative implementations, the foot 106 can include one needle capture device or three or more needle capture devices. One will appreciate that the number of needle capture devices in the foot 106 can correspond to the number of needles 122, 124 and needle lumens 126, 128 in the shaft 104. Each needle capture device 136, 138 can correspond to and be aligned with a needle lumen 126, 128, and a needle exit opening 130, 132. One will appreciate that by being aligned, the needles 122, 124 can pass out of the needle exit openings 130, 132, through the tissue ports 118, 120 and into the needle capture devices 136, 138.

Figure 6:
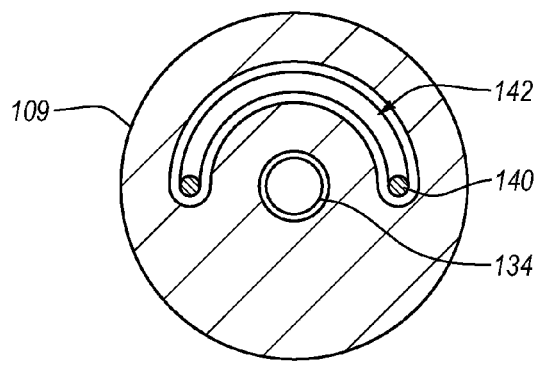
FIG. 6 illustrates a cross-sectional view of the suturing device of FIG. 1 taken along the line 6-6 of FIG. 1.

The needle capture devices 136, 138 can be secured to a suture 140 removably stored within a suture lumen 142 within the foot 106 and/or guidebody 109. For example, FIGS. 2 and 3 illustrates that the suturing device 100 includes a length of suture 140 having its respective ends secured to the first and second needle capture devices 136, 138. In particular, as illustrated by FIG. 6, the suture lumen 142 can extend at least partially around the guidewire lumen 134 and allow the suture 140 to wrap from the first needle capture device 136 to the section needle capture device 138. In alternative implementations, each needle capture device 136, 138 can have two or more sutures, ends or otherwise, secured thereto. As explained in greater detail below, multiple sutures may be desirable when closing larger openings or punctures within a body lumen.

The various implementations of the present invention may include any of a variety of suture types, such as, for example, monofilament or braided sutures. The sutures may be absorbable or non-absorbable, and may be made of polyester, polypropylene, polyglycolic acid, nylon, silk, or any of a variety of different materials.

Referring again to FIGS. 2 and 3, the suture 140 and the suture lumen 142 can extend from the foot 106 into the guidebody 109. In alternative implementations, the entire suture, or a substantially portion thereof, may be housed within the foot 106. For example, in some implementations, the suture 140 can be coiled and stored within the flared portion of the foot 106. In yet further implementations, the suture 140 can be stored or attached to the outer surfaces of the foot 106 or guidebody 109.

As shown by FIGS. 2 and 3, the needle capture devices 136, 138 can be configured to receive and secure the needles 122, 124 to the suture 140. In particular, once the needles 122, 124 are advanced into the needle capture devices 136, 138, the needle capture devices 136, 138 can lock the needles 122, 124 therein. Thereafter, when the needles 122, 124 are retracted from the foot 106 and the shaft 104, the needles 122, 124 can pull the suture 140 at least partially from the foot 106, through the needle lumens 126, 128, and out of the proximal end 108 of the shaft 104 or suturing device 100. In particular, by retracting the needles 122, 124, the suture 140 can be removed from the foot 106. Specifically, the suture 140 can pass out of the opening of the suture lumen 142 in the tissue location surface 144 (FIG. 5). Once the suture 140 has been harvested from the suturing device 100, the medical practitioner can remove the suturing device 100, retrieve the suture 140, and use it to close or otherwise seal an opening in a body lumen.

The needle capture devices 136, 138 can be substantially flush with a tissue location surface 144 (i.e., the surface of the foot opposite the distal end 110 of the shaft 104) as shown in FIGS. 2 and 3. Alternatively, the needle capture devices 136, 138 can reside further within the foot 106, as explained in greater detail below with reference to FIG. 9C. In such implementations, the foot 106 can include needle receiving lumens or funnels that extend from the tissue location surface 144 to the needle capture devices 136, 138, and that can guide the needles 122, 124 into the needle capture devices 136, 138.

As shown by FIGS. 2 and 3, the needles 122, 124 can be advanced in a distal direction from the proximal end 108 of the shaft 104 within the needle lumens 126, 128 by pressing the needle actuation handle 114 into the receptacle 125 of the handle 112 and/or shaft 104. The needles 122, 124 can advance out of the needle exit openings 130, 132, through tissue located within the tissue ports 118, 120, and into the needle capture devices 136, 138 within the foot 106. By being inserted into the needle capture devices 136, 138, the needle needles 122, 124 can be locked or secured to the suture 140. The needles 122, 124 and suture 140 can then be withdrawn proximately through the needle tracts formed in the tissue within the tissue ports 118, 120, and proximally out of the shaft 104 through the needle lumens 126, 128. In particular, by retracting the needles 122, 124, the suture 140 can be removed from the foot 106. Specifically, the suture 140 can pass out of the opening of the suture lumen 142 in the tissue location surface 144 (FIG. 5). Once the needles 122, 124 and suture 140 have been withdrawn from the foot 106, the suturing device 100 can be withdrawn from the patient. The suture 140 can then be drawn tight, closing the opening in the body lumen. A surgical knot or other suture securing device (e.g., a cleat) can complete the closure of the opening in the body lumen.

As previously mentioned, the needles 122, 124 can be configured to engage the needle capture devices 136, 138. One will appreciate that the needles 122, 124 and the needle capture devices 136, 138 can include various configurations so long as the needle capture devices 136, 138 can secure the needles 122, 124 to the suture 140, and allow the suture 140 to be harvested. For example, the needle capture devices 136, 138 of the present invention can include a net or other structure configured to receive and lock a needle to the suture 140.

Figure 4:
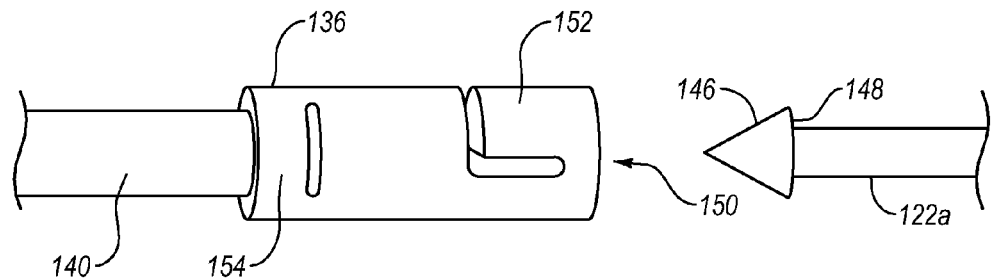
FIG. 4 illustrates a perspective view of a needle capture device and associated needle for use in the suturing device of FIG. 1.

In some implementations, as illustrated by FIG. 4, a needle 122a can include a barbed end 146 defining a recessed engagement surface 148. The needle capture device can comprise a needle attachment fitting or cuff 136. Specifically, the needle attachment cuff 136 can have a roughly cylindrical shape and include an axial channel 150 configured to receive the barbed end 146 of needle 122a therein. In additional implementations, the needle attachment cuff 136 can include shapes other than cylindrical ones, such as, for example, conical. The needle attachment cuff 136 can include one or more features configured to lock the barbed end 146 of the needle 122a therein. For instance, as shown in FIG. 4, the needle attachment cuff 136 can include at least one tab 152. The tab 152 may be mechanically formed to be smaller than the diameter of surface 148. The tab 152 can be resiliently biased into channel 150. As the needle 122a advances into the needle attachment cuff 136, the barbed end 146 can displace the tab 152 clear of the channel 150 so as to allow the barbed end 146 of the needle 122a to pass axially into the channel 105 of the needle attachment cuff 136. Once the barbed end 146 is disposed axially beyond the tab 152, the tab 152 tab can flex back into the channel 150 over the recessed surface 148, thereby locking the needle 122a to the needle attachment cuff 136. One will appreciate that each needle attachment cuff can include more than one tab 152, which can increase the reliability of the attachment between the needle 122a and the needle attachment cuff 136.

Additionally, FIG. 4 illustrates that the needle attachment cuff 136 can include a collar 154 to facilitate attachment of the needle attachment cuff 136 to suture 140. For instance, the collar 154 can be crimped about the suture 140 to mechanically affix the suture 140 to the needle attachment cuff 136. In addition and/or instead of mechanical crimping, the suture 140 may be bonded to the needle attachment cuff 136 using an adhesive, heat, fasteners, knots, or the like. As shown by FIG. 5, the foot 106 can house the needle attachment cuff 136. Or in other words, the needle attachment cuff 136 can extend distally into the tissue location surface 144 of the foot 106. In particular, in one implementation, the foot 106 can house a pair of needle attachment cuffs 136 on opposing sides of the spinal member 116 and/or guidewire lumen 134 (i.e., within the tissue ports 118, 120). FIG. 6A illustrates a cross-sectional view of the flexible guidebody 109. As shown by FIG. 6A, and as previously mentioned, the guidewire lumen 134 and suture lumen 142 can extend into the flexible guidebody 109 in one or more implementations.

As mentioned previously, the needle capture devices 136, 138 can be removably secured to the foot 106 so they can be withdrawn proximally into the shaft 104 as the needles 122, 124 are withdrawn. Additionally, one will appreciate that the outer body of the needle capture devices 136, 138 can be configured with a taper or other feature to help allow the needle capture devices 136, 138 to be readily pulled through paths formed by the needles 122, 124 in tissue located within the tissue ports 118, 120 when the practitioner retracts the needles 122, 124 and the needle capture devices 136, 138 from the patient.

Reference is now made to FIGS. 7A-7G, which illustrate one implementation of a method of using the suturing device 100 to close an opening 210 in a body lumen 200. Specifically, the suturing device 100 can be inserted in a distal direction into the body lumen 200. This can be accomplished with or without the use of a guidewire. FIGS. 7A-7G illustrate an example in which a guidewire 202 is used.

Figure 7A:
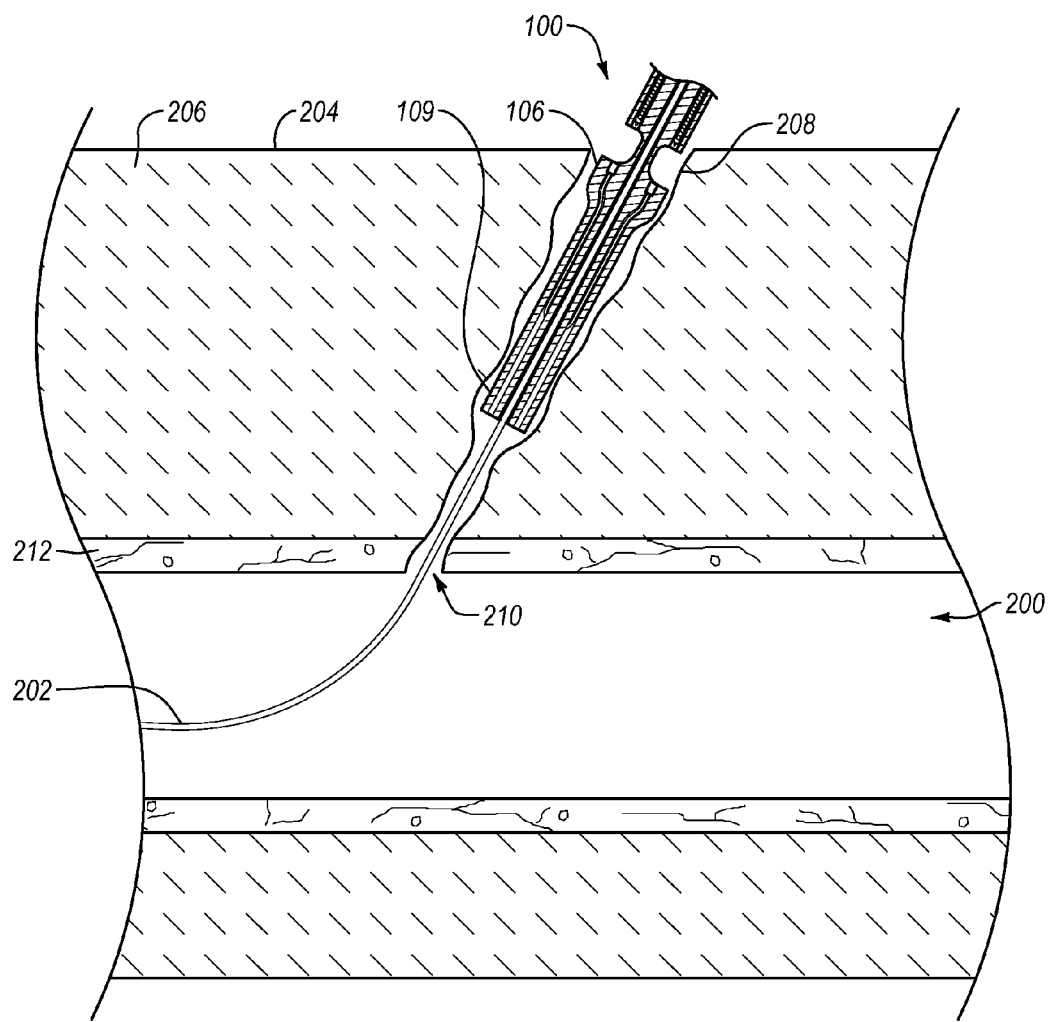
FIGS. 7A-7G illustrate cross-sectional views of a body lumen, showing a method for closing an opening in the wall of the body lumen using the suturing device of FIG. 1.
Figure 7B:
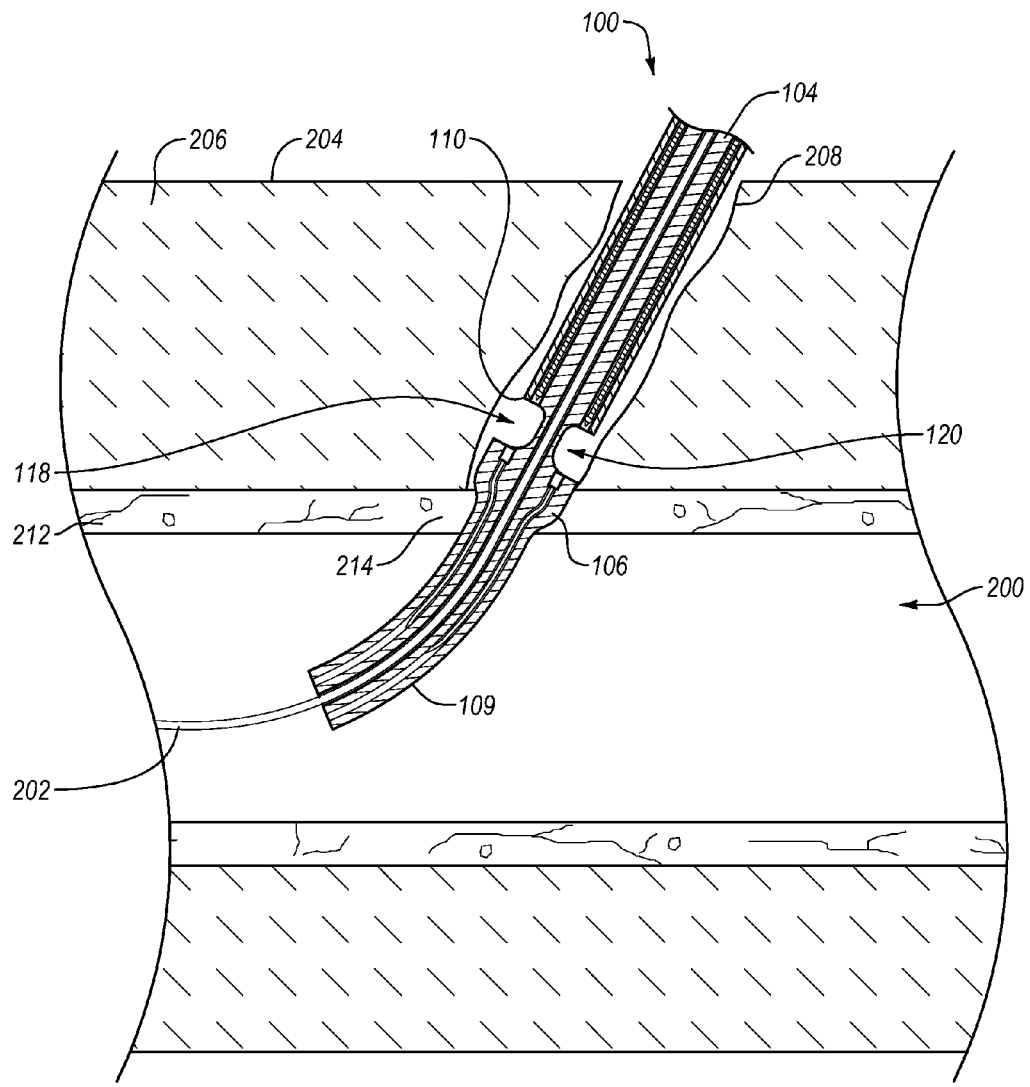

In particular, FIG. 7A illustrates that after accessing a body lumen, in this case a blood vessel 200, (using the Seldinger or a Modified Seldinger technique, for example), a guidewire 202 may be left extending into skin 204 and down through tissue 206 along a tissue tract 208, which may have been formed by an introducer sheath previously placed in connection with a intravascular medical or diagnostic procedure. As shown by FIG. 7A, the guidewire 202 may enter the body lumen 200 through an opening or puncture site 210 formed in the body lumen wall 212. The guidewire 202 may extend along the body lumen 200. As illustrated by FIGS. 7A-7B, the flexible guidebody 109 can be advanced over the guidewire 202 in a monorail fashion, so that the guidewire 202 helps direct the suturing device 100 along the tissue tract 208 into the body lumen 200 through the opening 210.

Figure 7C:
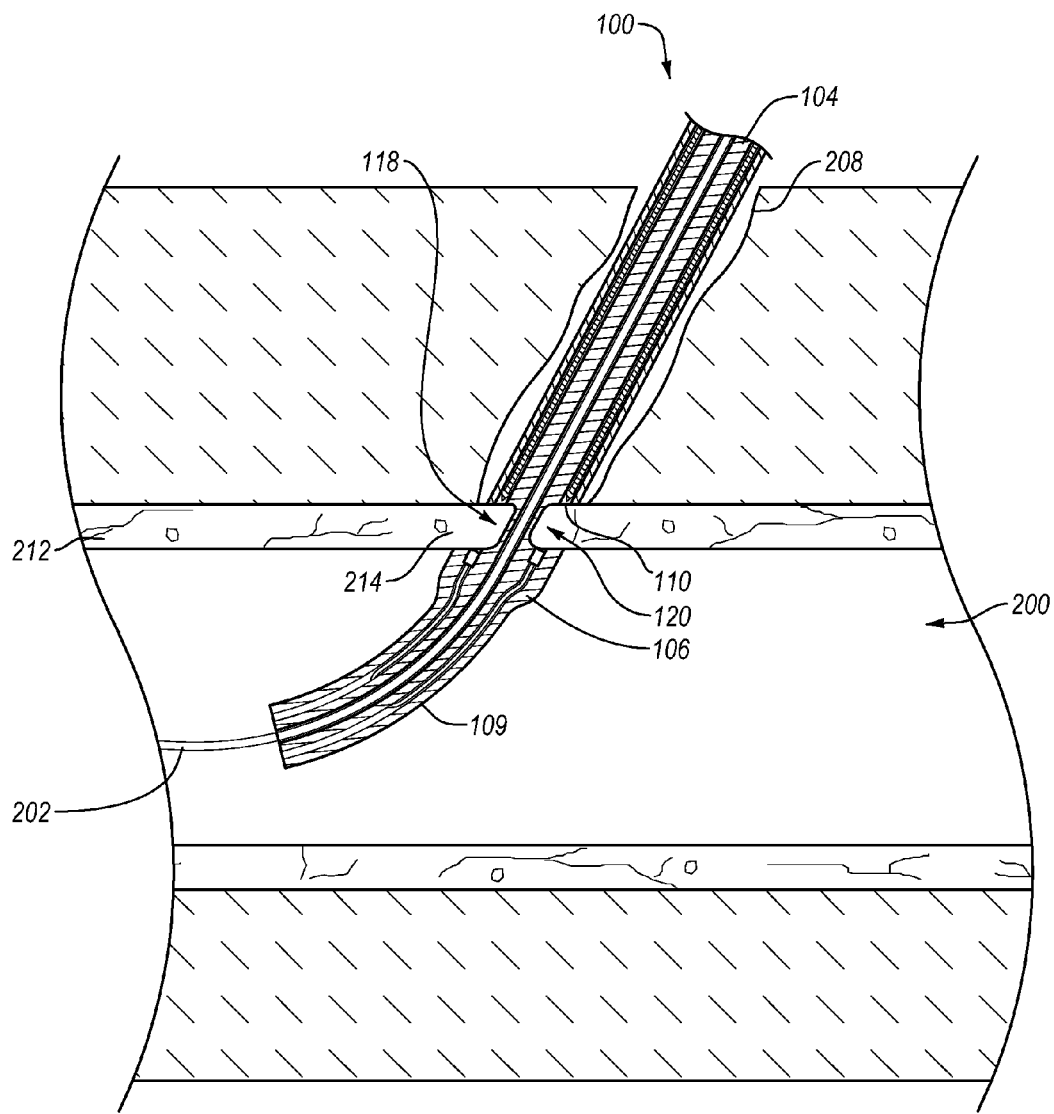

As shown by FIGS. 7B-7C, the suturing device 100 can be slowly advanced until resistance is encountered as the tissue ports 118, 120 cross the lumen wall 212 into the body lumen 200. The resistance can be provided by the radial flare of the foot 106 and/or by the distal end of the shaft 104. Alternatively, or additionally, the suturing device 100 can be advanced until blood is observed in a position indicator, such as that described below in relation to suturing device 300. In any event, once properly positioned, the suturing device 100 can be stabilized permitting the tissue 214 surrounding the opening 210 to rebound into the tissue ports 118, 120, as depicted in FIG. 7C.

Figure 7D:
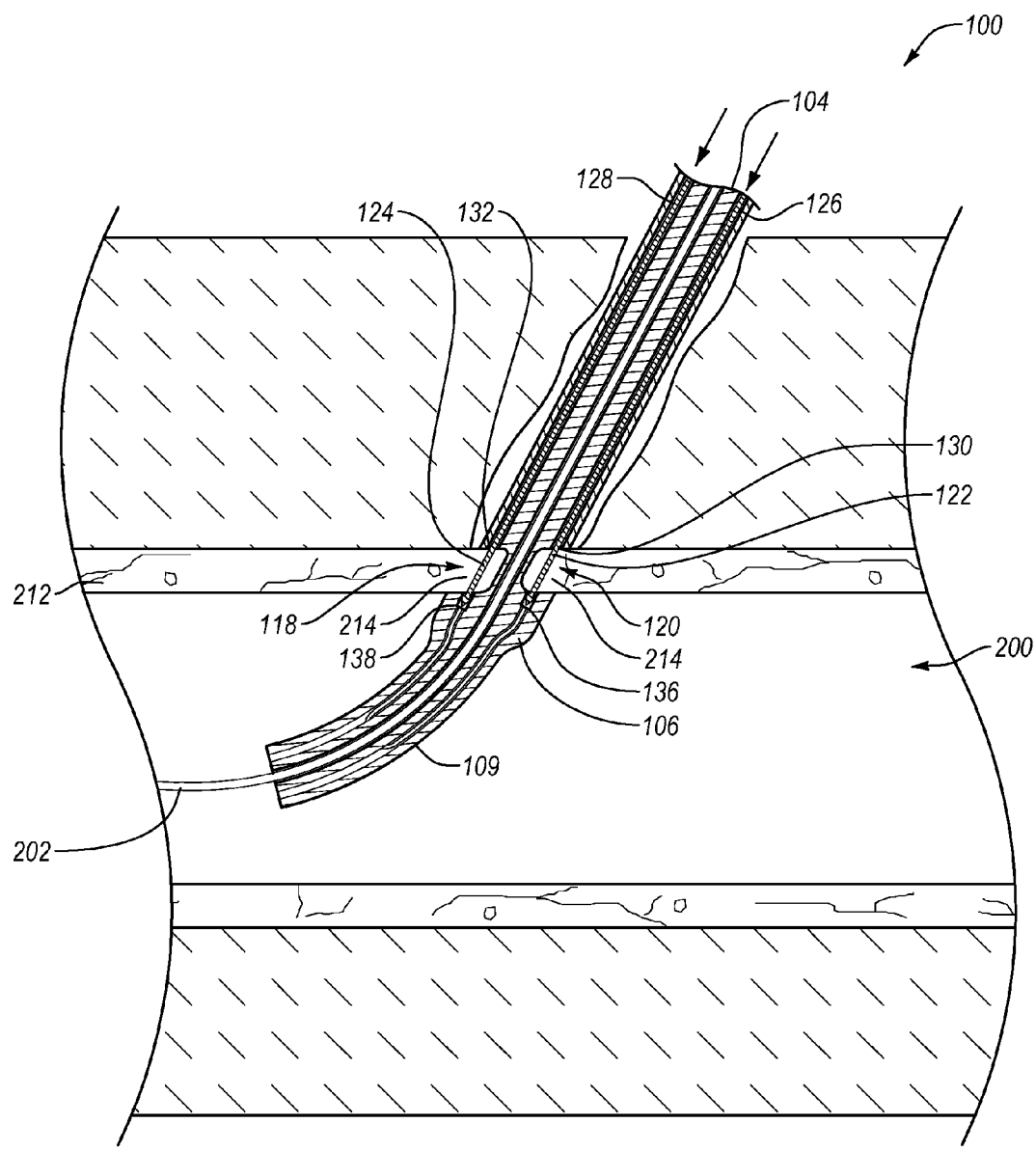
Figure 7E:
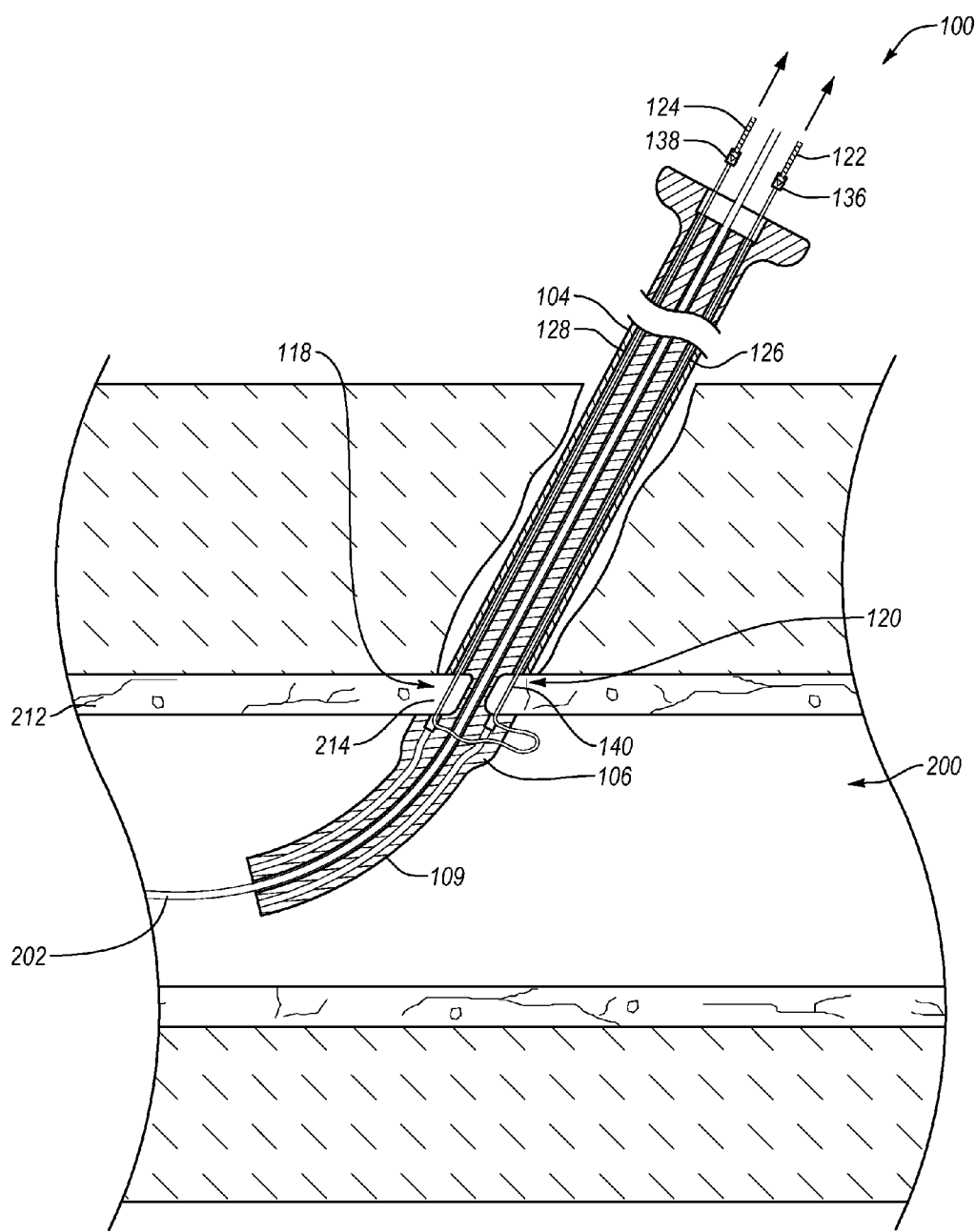

As shown in FIG. 7D, once the tissue 214 has entered into the tissue ports 118, 120, the needles 122, 124 can be advanced in a distal direction within the needle lumens 126, 128, out of the needle exit openings 130, 132, distally across the tissue ports 118, 120 through the tissue 214, and into the needle capture devices 136, 138. The needles 122, 124 and needle capture devices 136, 138 can then be withdrawn out of the foot 106, proximally across the tissue ports 118, 120 through the tissue 214, and out of the proximal end of the suturing device 100, as depicted by the arrow in FIG. 7E. FIG. 7E further shows that by withdrawing the needles 122, 124 and needle capture devices 136, 138, the distal end of the suture 140 can be withdrawn proximally out of the opening of the suture lumen 142 in the tissue location surface 144 and out of the foot 106.

Figure 7F:
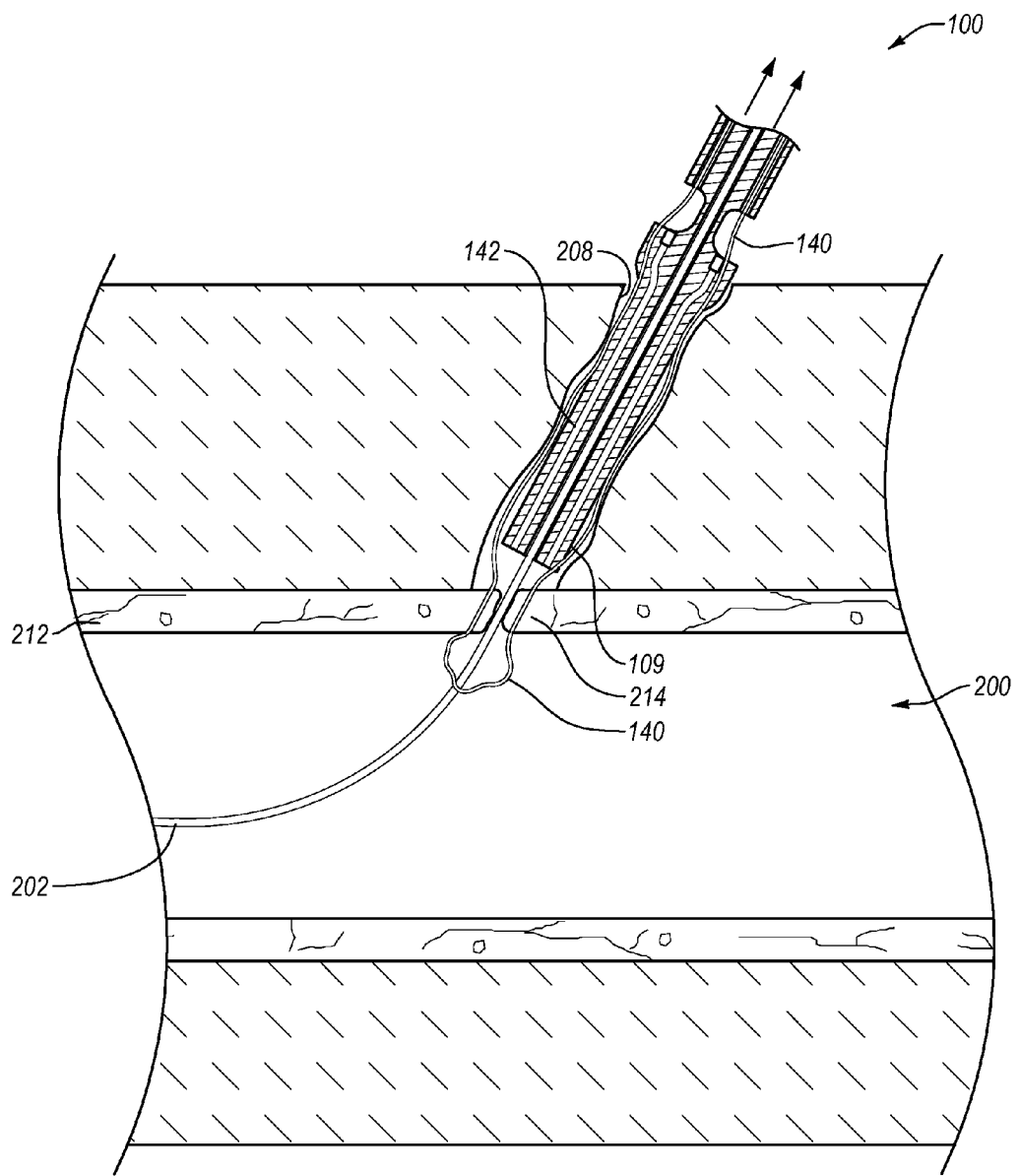

As indicated by the arrow of FIG. 7F, the suturing device 100 can next be withdrawn from the body lumen 200 and out of the tissue tract 208. The suture can then be severed, leaving sufficient length for the user to grasp the suture (by hand or with a tool) as well as to closure the opening 210, as further described below. As shown by FIG. 7F, the guidewire 202 can remain in place during the entire sequence to this point if desired. Thus, if the suture 140 fails to capture the tissue 214, or otherwise allow for the suture 140 to close the opening 210, another suturing device 100 can be inserted along the guidewire 202, and the above procedure repeated. One will appreciate that the ability to reuse the guidewire 202 if a problem is encountered can reduce the time, effort, and cost associated with resolving the problem and obtaining a dry closure of the body lumen 200.

Figure 7G:
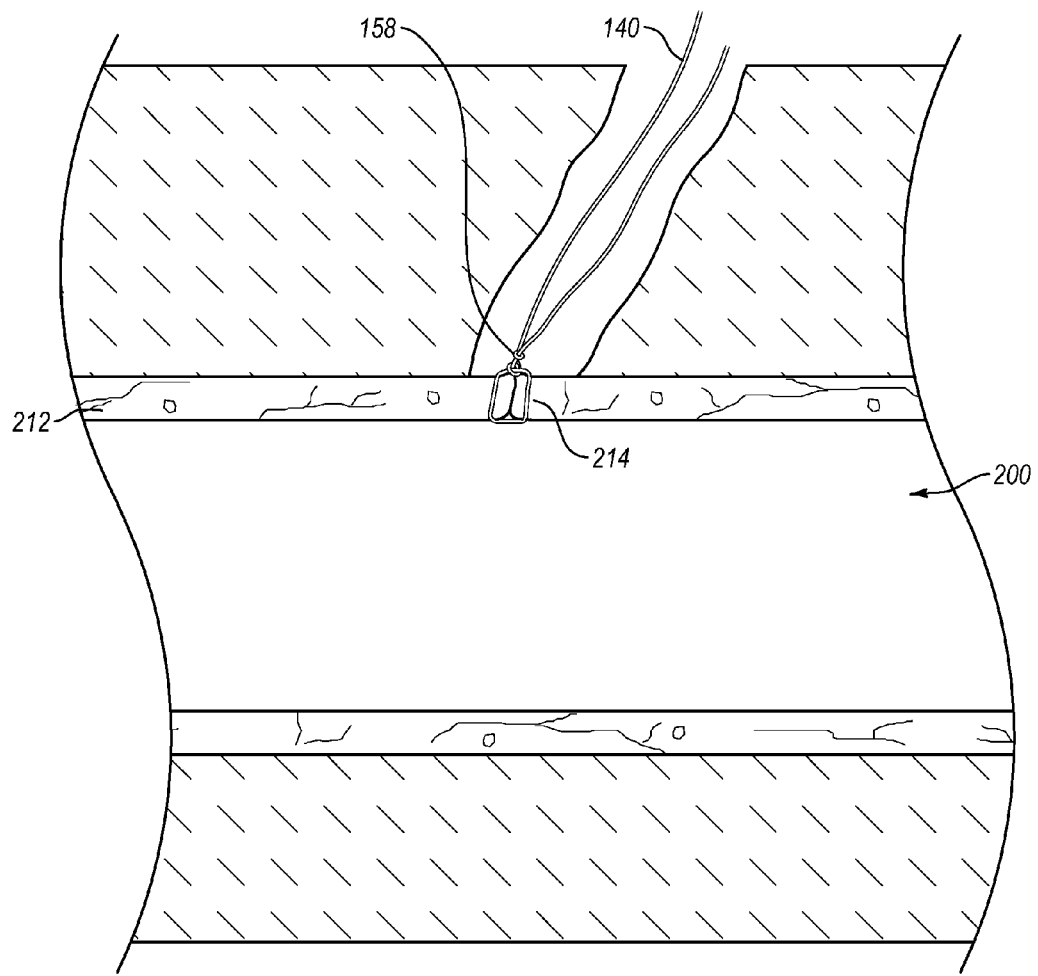

Finally, FIG. 7G illustrates that the guidewire 202 can be pulled from the patient. At this point, or prior thereto, the suture 140 can be employed to close the opening 210 in the body lumen 200. In particular, a surgical knot 158 can be tied securing the wound closure. A knot pusher, for example, the knot pushers described in U.S. Pat. No. 5,304,184 issued to) Hathaway et al., U.S. Pat. No. 5,746,755 issued to Wood et al., and U.S. Pat. No. 6,132,439 issued to Kontos, can be used to advance the loosely tied knot to the exterior surface of the vascular vessel. In some implementations, the medical practitioner can then tie a suitable surgical knot 158 using the respective lengths of suture 140 to close the opening 210 (FIG. 7A). In other embodiments, the suture 140 can be secured using a variety of knot replacement technologies such as those disclosed in U.S. Pat. No. 7,108,710 issued to Anderson. Each of the above-identified patents are incorporated herein by reference in their entirety.

In some cases, particularly for closure of large openings or punctures, it may be advantageous to provide multiple sutures 140 across the opening 210, either in parallel, in an "X" pattern, or in another configuration. For example, FIGS. 8 and 9 illustrate various views of a suturing device 100a similar to suturing device 100, except that suturing device 100a includes the use of more than two needles and associated needle lumens, needle capture devices, sutures, and the like. In particular, the suturing device 100a can include four needle lumens 124, 126, 124a, 126a, and four associated needles, four needle capture devices, and two sutures. Additional implementations of the present invention having multiple suture systems may have six, eight, or ten or more needles, or may even have odd numbers of needles and needle capture devices, particularly where one or more needle capture devices have a plurality of suture ends extending there from. This can allow a wide variety of stitching patterns to be provided by such multiple loop implementations.

More particularly, FIG. 8 illustrates that the suturing device 100a can include a shaft 104 and a distal portion or foot 106. FIG. 8 further illustrates that the suturing device 100a can include a flexible, guidebody 109 extending distally from the end of the foot 106. The foot 106 can include a flared portion that extends radially outward of the guidebody 109 and/or shaft 104. The shaft 104 can include a proximal end 108 and a distal end 110. A handle 112 can be secured to the proximal end 108 of the shaft 104. The handle 112 can be of sufficient dimensions to allow a medical practitioner to grasp the handle 112 and use it to manipulate the suturing device 100a during use. Furthermore, the handle 112 can support a needle actuation handle 114.

Figure 8A:
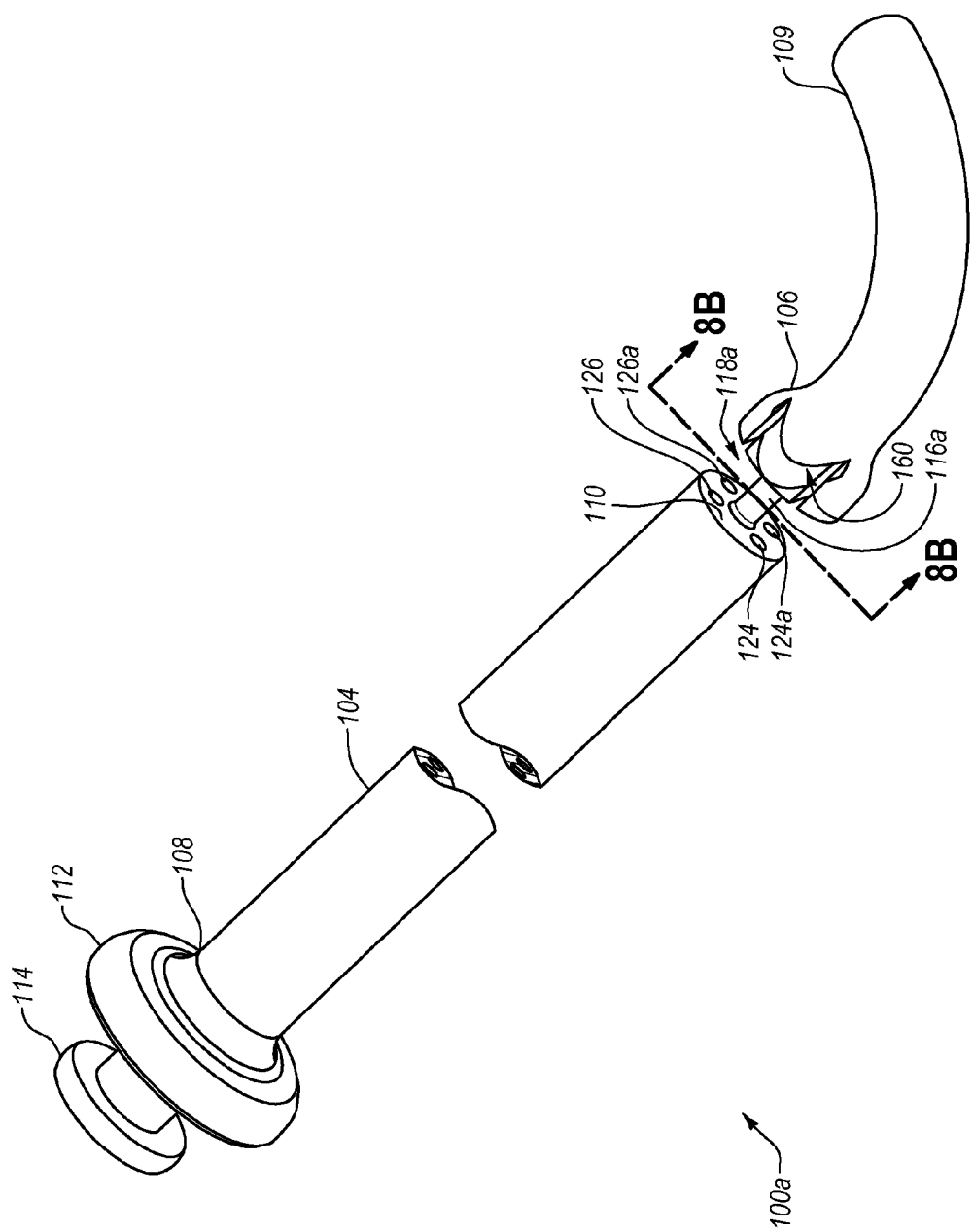
FIG. 8A illustrates a perspective view of another suturing device having a non-articulating foot in accordance with an implementation of the present invention.
Figure 8B:
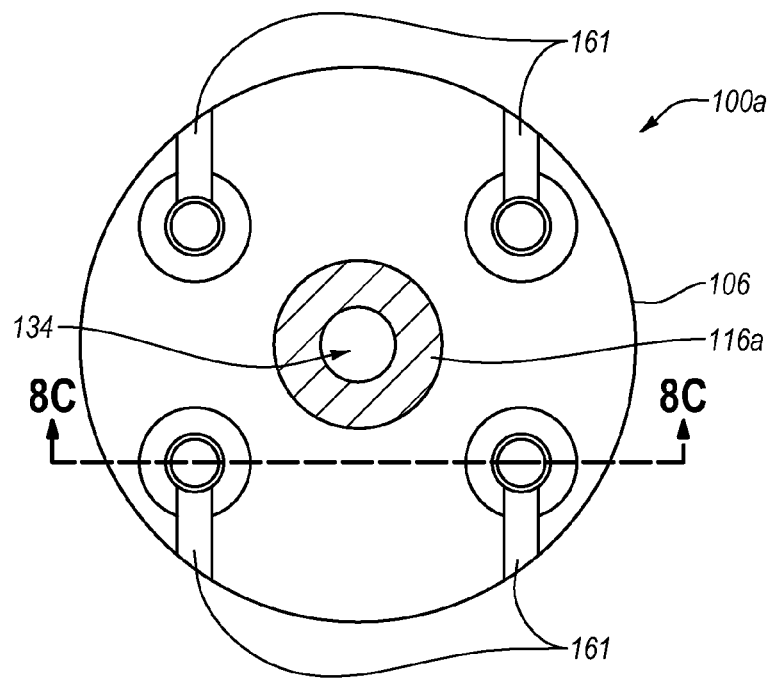
FIG. 8B illustrates a cross-sectional view of the suturing device of FIG. 8A taken along the line 8B-8B of FIG. 8A.
Figure 8C:
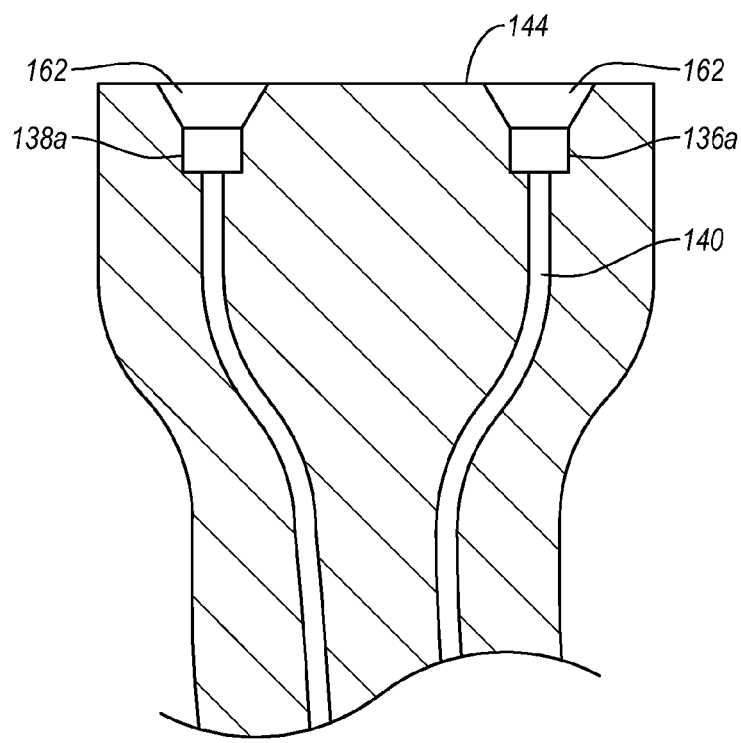
FIG. 8C illustrates a cross-sectional view of the suturing device of FIG. 9A taken along the line 8C-8C of FIG. 8B.
Figure 9A:
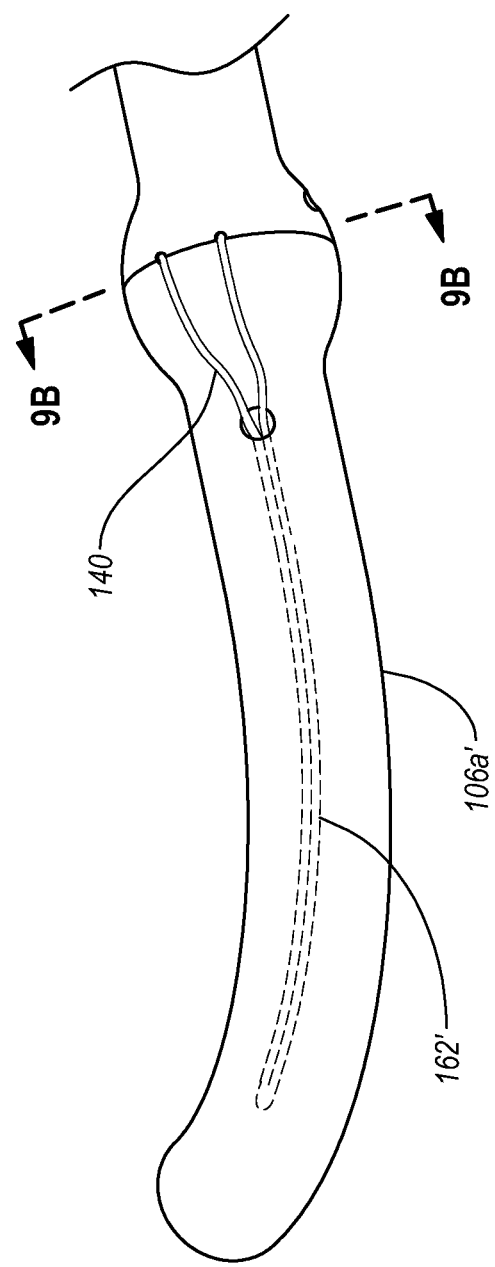
FIG. 9A illustrates a perspective view of a suturing device having a non-articulating foot in accordance with another implementation of the present invention.

Furthermore, as illustrated by FIGS. 8 and 9A, the spinal member 116a can have a circular cross-section and a diameter several times smaller than the diameter of the shaft 104 and/or foot 106. Thus, the suturing device 100a can include a single, circumferential tissue port 118a. In yet further implementations, suturing devices of the present invention can include a single tissue port that extends only partially around the circumference of the shaft 104 and foot 106. In additional implementations, suturing devices of the present invention can include three, four, five, or more tissue ports.

FIGS. 8A and 8B further illustrate that the suturing device 100a can include one or more suture exit slots 160. The suture exit slots 160 can extend from inside the foot 106 and/or guidebody 109 from the sutures 140, radially outward and in a proximal direction. The suture exit slots 160 can replace the opening of the suture lumen 142 in the tissue location surface 144 used in the suturing device 100 and function to allow the sutures 140 to be pulled radially out from the foot 106 and/or guidebody 109 as the needles and needle capture devices are withdrawn proximally from the suturing device 100a. In other words, the sutures 140 can be pulled out of, and separated from foot 106 and/or guidebody 109 as the needles and needle capture devices are distally withdrawn (i.e., before the shaft 104, foot 106, and guidebody the suturing device 100a are withdrawn). One will appreciate that by having the suture exit slots 160, the space needed within the foot 106 and/or guidebody 109 to house the sutures 140 may be reduced.

FIGS. 8B, 8C further illustrate that the suturing device 100a can include retaining slots 161. The retaining slots 161 can be configured to allow the foot 106 to receive and retain therein needle capture devices 136a, 138a. For example, the ports within the foot 106 within which the needle capture devices 136a, 138a can have a diameter smaller than the outer diameter of the needle capture devices 136a, 138a. The retaining slots 161 can allow the ports, which hold the needle capture devices 136a, 138a within the foot 106, to expand to receive the needle capture devices 136a, 138a. Once within the ports of the foot 106, the retaining slots 161 can allow the ports to bias toward and retain the needle capture devices 136a, 138a therein.

As alluded to earlier, the suturing devices of the present invention can include needle receiving lumens or funnels for guiding the needles into the needle capture devices 136a, 138a. For example, FIGS. 9A and 8C illustrate that the needle capture devices 136a, 138a can reside within the foot 106 a distance from the tissue location surface 144. Needle receiving lumens or funnels 162 can extend from the tissue location surface 144 to the needle capture devices 136a, 138a. The funnels 162 can have a diameter at the tissue location surface 144 that is larger than the diameter of the needle capture devices 136a, 138a. The diameter can then taper as the funnels extend toward the needle capture devices 136a, 138a. One will appreciate in light of the disclosure herein that the funnels 162 can thus guide the needles into the needle capture devices 136a, 138a in the event that they are slightly deflected out of alignment when passing through tissue.

Figure 9B:
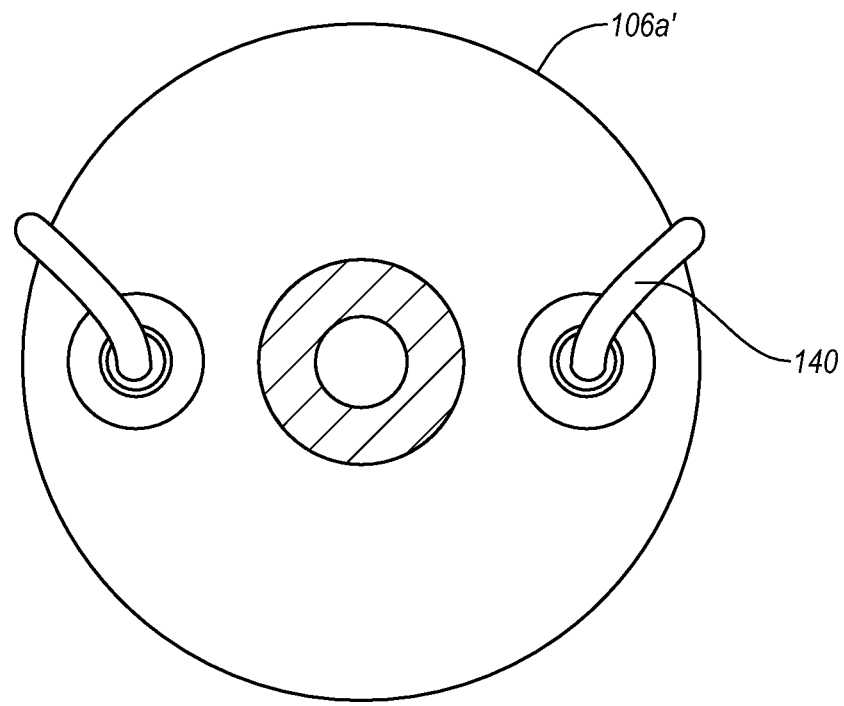
FIG. 9B illustrates a cross-sectional view of the suturing device of FIG. 9A taken along the line 9B-9B of FIG. 9A.

Additional or alternative implementations, as illustrated in FIG. 9A, in lieu of or in addition to the exit slot, a suturing device 100a' can include a foot 106a' that has a retaining channel 162', which house the sutures 140. After engaging the suturing device 100a' with the vessel wall, and connecting the needles with needle capture devices, the sutures 140 can be pulled out of the retaining channel 162'. Furthermore, in at least one implementation, the sutures 140 can be positioned on the outside of the foot 106a' (i.e., the foot may not have any channels or retaining slots therein). In other words, as illustrated in FIG. 9B, the sutures 140 may spill over the side of the foot 106a'.

Figure 9C:
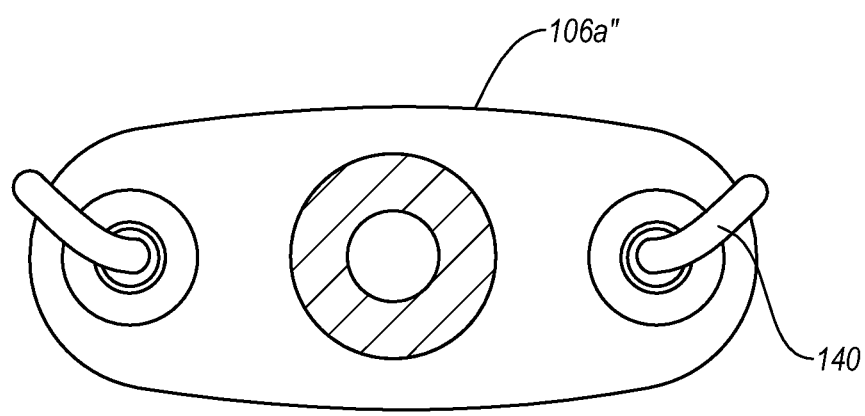
FIG. 9C illustrates a cross-sectional view of another implementation of the suturing device of FIG. 9A.

In addition, although in some implementations the foot 106' may have an approximately circular cross-sectional shape (e.g., the shape at the tissue location surface 144 (FIG. 8C), the shape of the foot may vary from one implementation to another. For instance, as illustrated in FIG. 9C, the suturing device can incorporate a foot 106a" of a suturing device 100a". The foot 106a" may have an oval cross-sectional shape. It should be appreciated, however, that the foot can have any number of suitable shapes.

While the implementations described hereinabove included passive tissue ports or non-articulating foot, the present invention is not so limited. As previously mentioned, implementations of the present invention can also include suturing devices with an articulating foot or non-passive tissue ports. Such implementations can include a foot that articulates between a pre-deployed configuration and deployed configuration. In the pre-deployed configuration the tissue ports can be at least partially closed. In the deployed configuration the tissue ports can be open. For example, in one implementation the foot can be distally displaced from the shaft when in the deployed configuration, thereby opening tissue ports between the foot and the shaft. In implementations including an articulating foot, the foot can be used to draw or push tissue surrounding an opening in a body lumen to be repaired into the tissue ports.

For example, FIGS. 10A-11B illustrate perspective view of a suturing device 300 with an actuating foot 106a in accordance with an implementation of the present invention. The suturing device 300 can include a body 102a comprising a proximal portion or shaft 104a and a distal portion or foot 106a. FIGS. 10A-12B further illustrate that the suturing device 300 can include a flexible, guidebody 109a extending distally from the end of the foot 106a. The foot 106a can include a flared portion that extends radially outward of the guidebody 109a. The shaft 104a can include a proximal end 108 and a distal end 110. A handle 112a can be secured to the proximal end 108 of the shaft 104a. The handle 112a can be of sufficient dimensions to allow a medical practitioner to grasp the handle 112a and use it to manipulate the suturing device 300 during use. Furthermore, the handle 112a can support a needle actuation handle 114a.

Similar to the suturing device 100, the suturing device 300 can include one or more needles 122, 124 secured to the needle actuation handle 114a. The needle actuation handle 114a can be sized to be positioned within a receptacle extending into the proximal end of the handle 112a. The needle actuation handle 114a can allow a medical practitioner to advance the needles 122, 124 into the shaft 104a and foot 106a. In particular, the shaft 104a can include one or more needle lumens 126, 128 extending from the proximal end 108 to the distal end 110 of the shaft 104a. The needle lumen 126, 128 can guide the needles 122, 124 from the proximal end 108 of the shaft 104a, through the shaft 104a, and into the foot 106a.

Additionally, the foot 106a can include one or more needle capture devices. For example, FIGS. 10B and 11B illustrates that the foot 106a can include a first needle capture device 136 and a second needle capture device 138, each removably secured within a tissue location surface 144 of the foot 106a. Each needle capture device 136, 138 can correspond to and be aligned with a needle lumen 126, 128. Referring now to FIG. 11C, the suturing device 100a can include retaining slots 161a configured to allow the foot 106a to receive and retain therein needle capture devices 136, 138.

The needle capture devices 136, 138 can be secured to a suture 140 removably stored within the foot 106a and/or guidebody 109a. For example, a length of suture 140 can have its ends secured to the first and second needle capture devices 136, 138. As previously mentioned, the needle capture devices 136, 138 can be configured to receive and secure the needles 122, 124 to the suture 140. In particular, once the needles 122, 124 are advanced into the needle capture devices 136, 138, the needle capture devices 136, 138 can lock the needles 122, 124 therein. Thereafter, when the needles 122, 124 are retracted from the foot 106a and the shaft 104a, the needles 122, 124 can pull the proximal ends of the suture 140 from the foot 106a, through the needle lumens 126, 128 and out of the proximal end 108 of the shaft 104a.

As shown by FIG. 11C, the suture 140 can extend from the needle capture devices 136, 138, out of retaining slots 161a, along the outer wall of the foot 106a, and into the guidebody 109a via suture exit slot 160a. As the needles 122, 124 are retracted from the foot 106a and the shaft 104a, the distal portion or loop of the suture 140 can be pulled from the guidebody 109a and foot 106a. In particular, as the suture 140 is pulled proximately, the suture 140 can exit the guidebody 109a and foot 106a via the suture exit slot 160a and retaining slots 161a. Once the suture 140 has been pulled from the guidebody 109a and foot 106a, the suturing device 300 can be proximately withdrawn from the patient. As shown in FIG. 11C, the suture exit slot 160a can extend generally radially outward from the center of the guidebody 109a. The radial configuration can help ensure that the suture exit slot 160a does not catch or pull on tissue as the suturing device 300 is withdrawn.

The suturing device 300 can further include a foot actuator mechanism 302. As shown in FIGS. 10A-11B, a medical practitioner can slide the foot actuator mechanism 302 distally toward the foot 106a, thereby causing the foot 106a to be distally displaced from a first configuration (FIGS. 10A-10B) in which the foot 106a abuts against the distal end 110 of the shaft 104a and a deployed configuration (FIGS. 11A-11B) in which the foot 106a is distally separated from the distal end 110 of the shaft 104a.

Figure 11A:
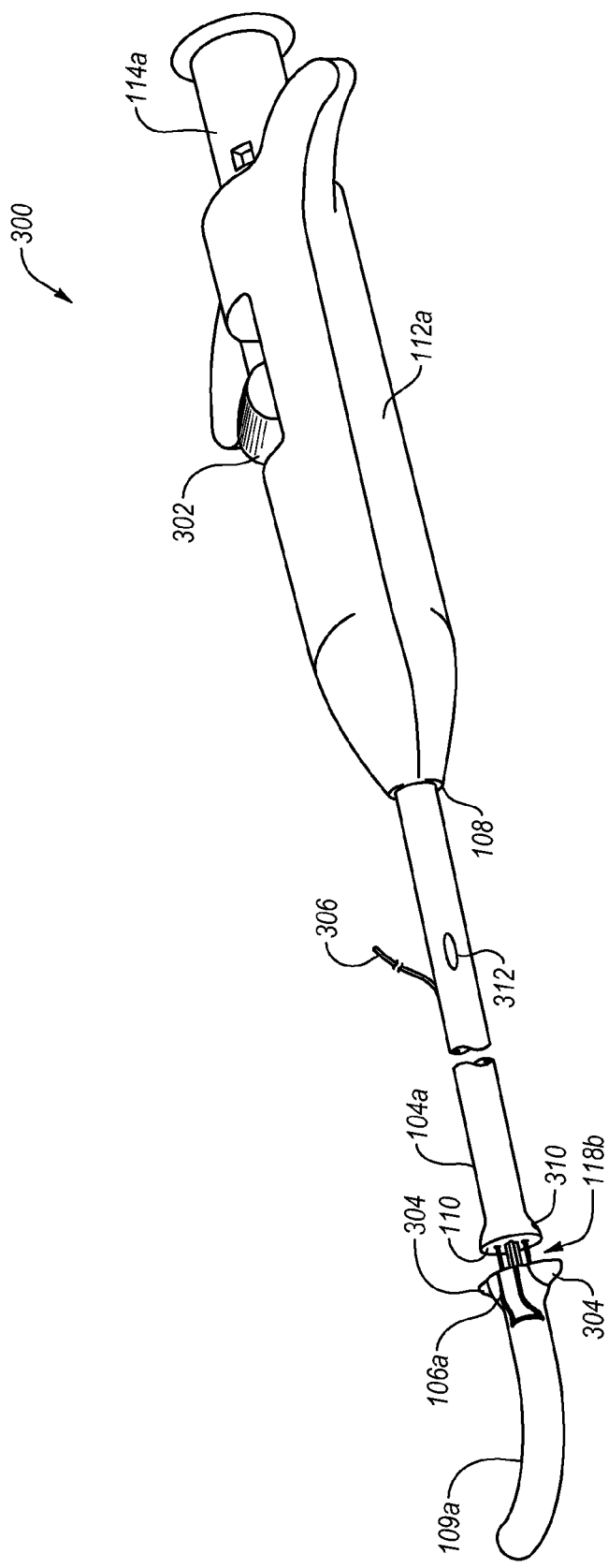
FIG. 11A illustrates a perspective view of the suturing device of FIG. 10A with the articulating foot in a deployed configuration.
Figure 11B:
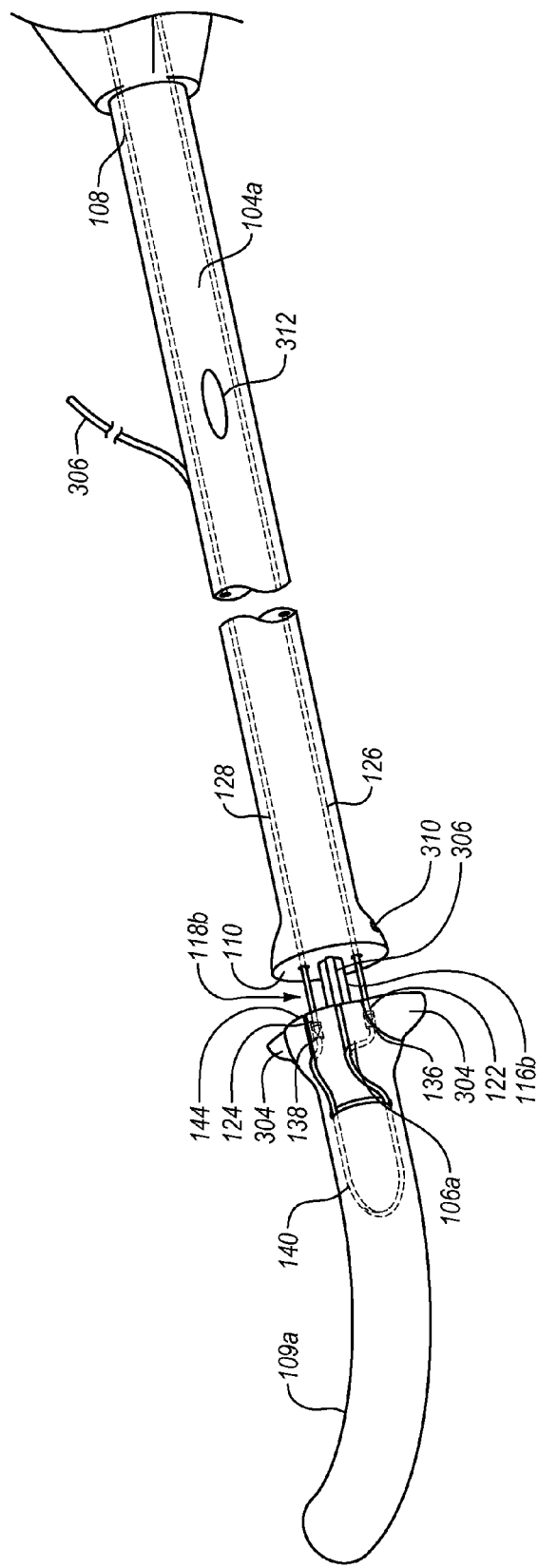
FIG. 11B illustrates an enlarged view of the shaft and articulating foot of the suturing device of FIG. 11A.
Figure 11C:
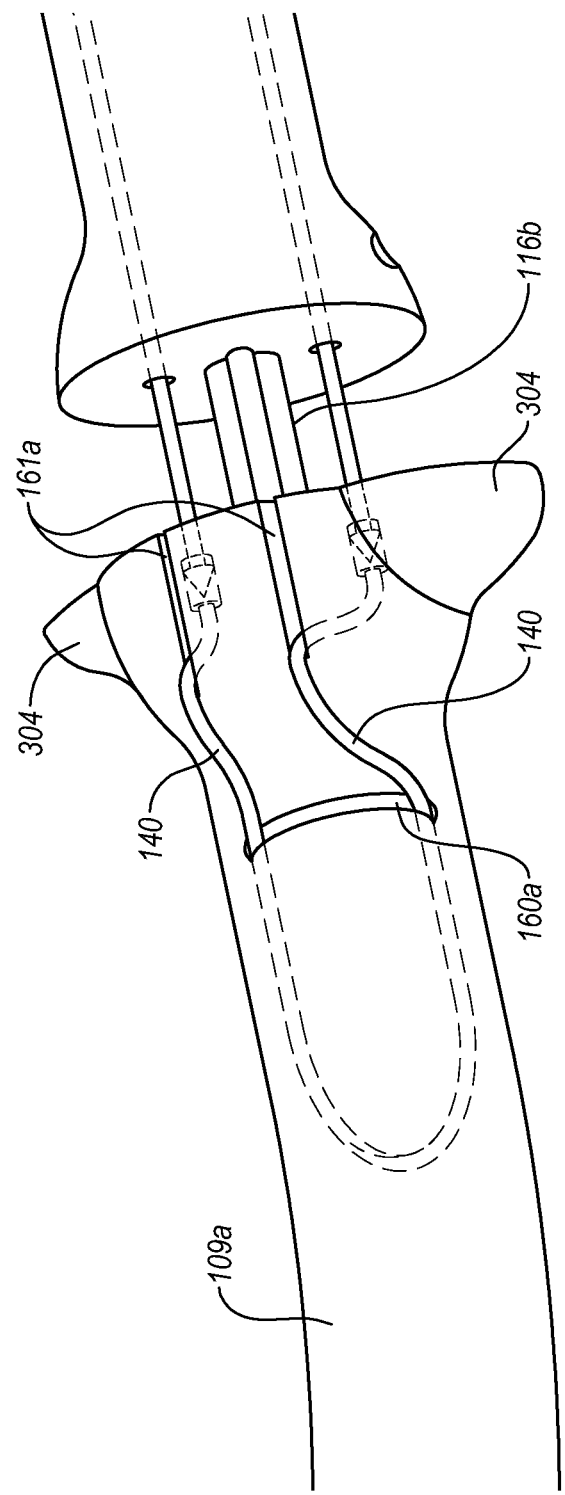
FIG. 11C illustrates a further enlarged view of the articulating foot of the suturing device of FIG. 11A.

As shown by FIGS. 11A-11B, by actuating the foot 106a into the deployed configuration, a tissue port 118b can be opened up between the foot 106a and the shaft 104a. As discussed previously, the tissue port 118b can receive tissue surrounding body lumen opening to be closed using the suturing device 300. As shown in FIGS. 11A-11B, when in the deployed configuration the foot actuator mechanism 302 can distally displace a spinal member 116b within the shaft 104a, thereby distally displacing the foot 106a secured, which may be secured to the spinal member 116b. Thus, the spinal member 116b can help define the tissue port 118b.

Figure 10A:
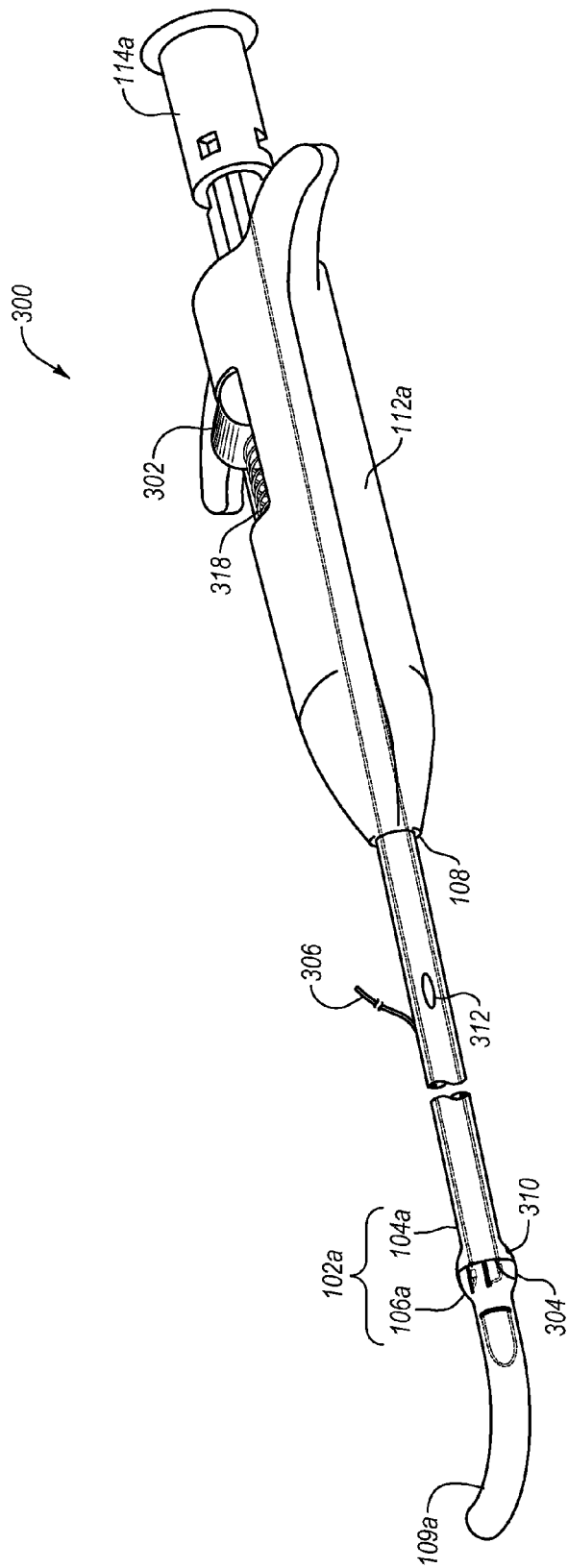
FIG. 10A illustrates a perspective view of a suturing device with an articulating foot in parked configuration in accordance with an implementation of the present invention.
Figure 10B:
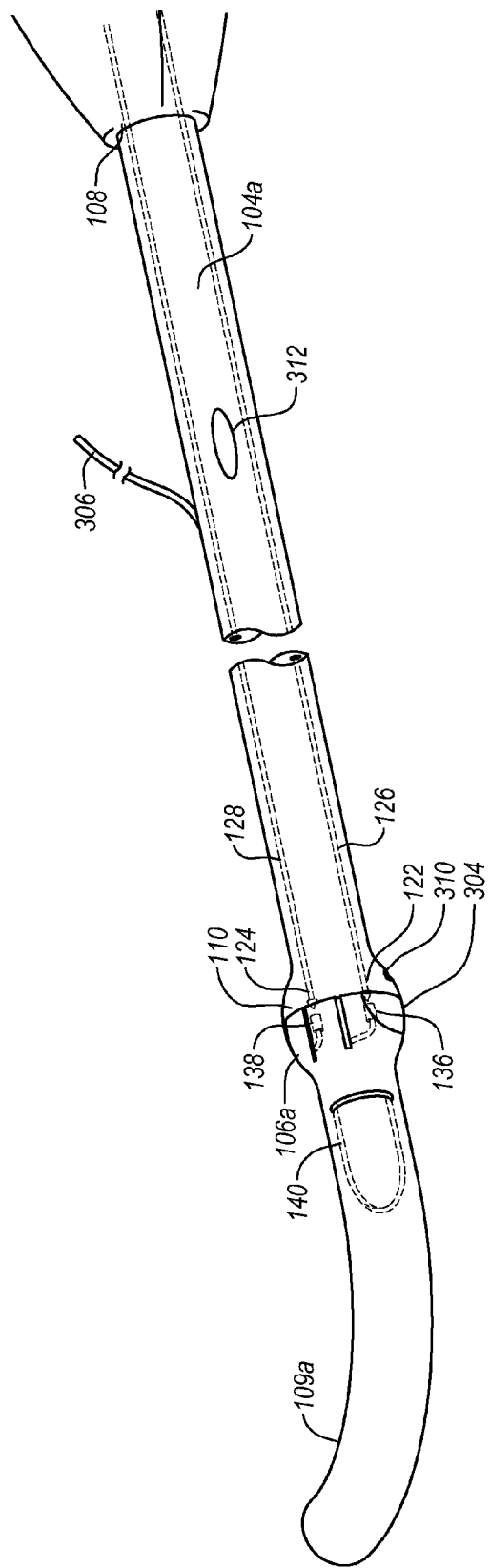
FIG. 10B illustrates an enlarged view of the shaft and articulating foot of the suturing device of FIG. 10A.

The foot actuator mechanism shown in FIGS. 10A and 11A comprises a tab 302 directly secured to the spinal member 116b. In such implementations, the foot actuator mechanism 302 can the medical practitioner with tactile feedback on how far the foot 106a has been deployed. In particular, in some implementations the distance the foot actuator mechanism 302 slides distally within the handle 112a can have a 1:1 ratio with respect to the distance the foot 106a separates from the distal end 110 of the shaft 104a. In alternative implementations, the distance the foot actuator mechanism 302 slides distally within the handle 112a can have a 2:1 ratio, a 3:1, a 4:1 ratio, or a greater ratio with the distance the foot 106a separates from the distal end 110 of the shaft 104a. In yet further implementations, the distance the foot actuator mechanism 302 slides distally within the handle 112a can have a 1:2 ratio, a 1:4 ratio, or a smaller ratio with respect to the distance the foot 106a separates from the distal end 110 of the shaft 104a.

A wide variety of foot actuation mechanisms can be employed to move the foot 106a between the first configuration (FIGS. 10A-10B) and the deployed configuration (FIGS. 11A-11B). The tab 302 illustrated in FIGS. 10A and 11A is only one example of such a mechanism. In additional implementations, the foot actuation mechanism can include a handle that pivots from a position generally perpendicular to the central axis of the handle 112a to a position generally parallel to the central axis of the handle 112a. In yet further implementations, the foot actuation mechanism can include a handle secured to the spinal member 116b that is positioned between the handle 112a and the needle actuation handle 114a. In such implementations, the medical practitioner can depress the foot actuation mechanism handle at least partially within the handle 112a to deploy the foot 106a. The medical practitioner can then depress the needle actuation handle 114a at least partially within the foot actuation mechanism handle to deploy the needles 122, 124.

In any event, once the foot 106a is deployed (FIGS. 11A-11B) the medical practitioner can proximally withdraw the foot 106a until it abuts against the inner wall of a body lumen to be closed. After which, the medical practitioner can compress the foot 106a and the shaft 104a together thereby urging or pushing tissue into the tissue port 118b. Thus, the articulating foot 106a can function to help ensure that tissue surrounding an opening to be closed is properly positioned within the tissue port 118b prior to deployment of the needles 122, 124.

In some implementations, the foot actuation mechanism 302 can be biased toward the first configuration (FIGS. 10A-10B). For example, FIG. 10A illustrates that the suturing device 300 can include a biasing member 318 configured to bias the foot actuation mechanism 318 toward the proximal end of the handle 112a. FIG. 10A illustrates that the biasing member 318 can comprise a leaf string. In alternative implementations, the biasing member 118 can include an elastomeric projection, or other structure that provides biasing characteristics similar to a spring, including, for example, a torsion spring, or a twin spring. One will appreciate in light of the disclosure herein that the biasing member 318 can cause the foot 106a to automatically move from the deployed configuration (FIGS. 10A-10B) toward the first configuration (FIGS. 11A-11B) upon release of the foot actuation mechanism 302. Thus, the biasing member 318 can cause the foot 106a to automatically capture tissue and urge the tissue into the tissue port 118b once the tissue location surface 144 is abutted against the inner wall of the body lumen, and the foot actuation mechanism 302 is released. In alternative implementations, the foot actuation mechanism 302 may not include a biasing member, and the actuation of the foot 106a can be a manual procedure performed by the medical practitioner.

In some implementations of the present invention, the suturing device 300 can include a locking mechanism configured to releasably lock the foot 106a in one or more configurations, such as, for example, the first or pre-deployed configuration, the deployed configuration, or a position between the first and deployed configurations. For instance, the locking mechanism can lock the foot 106a, and the foot actuation mechanism 302, in the deployed configuration (FIGS. 10A-10B) to ensure that the foot 106a is not compressed toward the shaft 104a, or vice versa, until the foot location surface 144 is positioned against the inner wall of a body lumen to be repaired. Alternatively or additionally, the locking mechanism can releasably lock the foot 106a in place relative to the shaft 104a once tissue has been captured in the tissue port 118b. This can help ensure that the foot 106a and the shaft 104a pinch or otherwise hold the tissue surrounding an opening to be repaired until the medical practitioner can deploy the needles 122, 124.

Figure 12A:
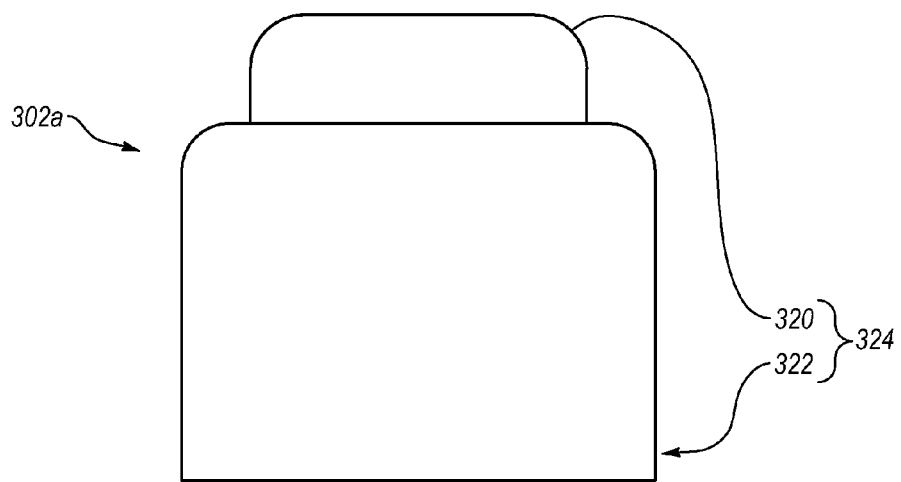
FIG. 12A illustrates an end view of a foot actuator mechanism with a locking mechanism for use in the suturing device of FIG. 10A in accordance with an implementation of the present invention.
Figure 12B:
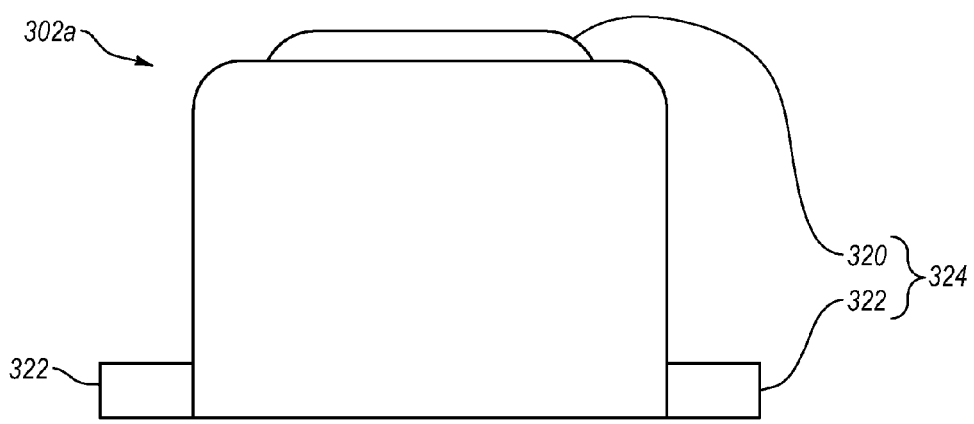
FIG. 12B illustrates the foot actuator mechanism and locking mechanism of FIG. 12A with the locking mechanism engaged.

For example, FIGS. 12A and 12B illustrate one implementation of a foot actuation mechanism that includes a locking mechanism 324. Specifically, FIGS. 12A and 12B illustrate that the locking mechanism 324 can include a button 320 and one or more protrusions 322. Specifically, in the illustrated implementation, the foot actuation mechanism 302a includes a button 320. When the button 320 is in the decompressed position shown in FIG. 12A, the foot actuation mechanism 302a, and the foot 116a, can freely move relative to the handle 112a and/or shaft 104a. Alternatively, when the button 320 is in the compressed position shown in FIG. 12B, one or more protrusions 322 may extend out from the foot actuation mechanism 302a. When extended, the one or more protrusions 322 may engage corresponding grooves (not shown) located within the handle 112a, thereby locking the foot actuation mechanism 302a and the foot 106a relative to the handle 112a and/or shaft 104a. Thus, the locking mechanism 324 can allow a medical practitioner to lock the foot 106a in one or more positions relative to the shaft 104a.

In order to release the locking mechanism 324, the medical practitioner can decompress the button 320, thereby withdrawing the one or more protrusions 322 into the foot actuation mechanism 302a. When in the decompressed position, the foot actuation mechanism 302a, and the foot 116a, can freely move relative to the handle 112a and/or shaft 104a.

In additional implementations, the suturing devices can include locking mechanisms having other configurations. For example, such locking mechanisms can include spring-loaded tabs (not shown) that extend into the housing 112a or shaft 104a from the foot actuation mechanism. Such spring-loaded tabs can prevent actuation of the foot 106a unless deactivated by compressing a button or other release mechanism similar to the button 320.

In some implementations of the present invention, the suturing device 300 can include both a biasing member 318 and a locking mechanism 324. Alternatively, the suturing device 300 can include one of a biasing member 318 and a locking mechanism 324, or neither a biasing member 318 or a locking mechanism 324. One will appreciate that the inclusion of the biasing member 318 and/or locking mechanism 324 can be based on a medical practitioner's preference.

Referring again to FIGS. 10A-11A, the suturing device can include a foot position indicator lumen 308 (FIGS. 13A-13I) that extends distally from a position port 310 to position indicator 312 located on the shaft 104a. When the foot 106a is properly positioned for deployment within a blood vessel or other body lumen (i.e., the tissue location surface 144 is completely within the body lumen), blood pressure can cause blood to flow into the position port 310, proximally through the indicator lumen 308 (FIGS. 13A-13I) to the position indicator 312.

As shown in FIGS. 10A-11B, the position indicator may optionally comprise a window 312 in which blood within the indicator lumen may be visible. In particular, FIGS. 10A-11B illustrate that the shaft 104a (or in alternative implementations the handle 112a) can include a clear window 312. In further implementations, the position indicator can comprise a length of the indicator lumen 308 that extends outside of the shaft 104a or handle 112a through which blood can flow out, indicating to the medical practitioner that the foot 106a is properly positioned. In yet further implementations, the position indicator can include electrical pressure sensors, electrolytic fluid detectors, or the like.

In additional implementations, the foot 106a or the distal portion of the shaft 104a can include a radiopaque material to increase visibility during placement. Optionally, the radiopaque material can be a layer or coating any portion of the foot 106a or shaft 104a. The radiopaque materials can be platinum, tungsten, silver, stainless steel, gold, tantalum, bismuth, barium sulfate, or a similar material.

It is further contemplated that the external surface and/or internal surface of the devices or members (e.g., exterior and luminal surfaces) as well as the entire body can be coated with another material having a composition different from the primary material. The use of a different material to coat the surfaces can be beneficial for imparting additional properties to the device or member, such as providing radiopaque characteristics, drug-reservoirs, and improved biocompatibility.

In one embodiment, at least one biocompatible polymeric layer can be a coating that is applied over the entire suturing device 300, or to select portions. Examples of such biocompatible polymeric materials can include a suitable hydrogel, hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like. Additionally, the coating can include hydrophilic and/or hydrophobic compounds, polypeptides, proteins, amino acids, polyethylene glycols, parylene, heparin, phosphorylcholine, or the like.

The coatings can also be provided on the suturing device 300 or portion thereof to facilitate the loading or delivery of beneficial agents or drugs, such as therapeutic agents, pharmaceuticals and radiation therapies. As such, the material and/or holes can be filled and/or coated with a biodegradable material.

FIGS. 10A-11A further illustrates that the suturing device 300 can include one or more balloons 304 secured to the foot 106a. The balloons 304 can be inflated by sending air or another fluid into a balloon lumen 306 extending from the shaft 104a into the foot 106a (e.g., a connector, such as a luer, can be couple to a proximal end of the balloon lumen 306 to allow connection to a fluid source). Once inflated, the balloons 304 can effectively increase the surface area of the tissue location surface 144 and aid in locating the tissue surrounding an opening in a body lumen to be closed, as explained in greater detail below. One will appreciate that a medical practitioner can inflate the balloons 304 after receiving an indication from the position indicator 312 that the foot 106a is in a position ready for deployment. In particular, the balloons 304 can be inflated prior actuating the foot actuator mechanism 302 to deploy the foot 106a or after deploying the foot 106a.

In any case, the balloons 304 can help ensure that the foot 106a cannot be proximally withdrawn back through the body lumen when the foot 106a and shaft 104a are compressed together to draw tissue into the tissue port 118b. One will appreciate that the balloons 304 can provide the aforementioned functions without dilating or otherwise damaging the opening in the body lumen to be closed. In particular, because the balloons 304 can be deflated prior to passing the foot 106a distally or proximally through the body lumen, the balloons 304 can avoid damaging the tissue surround the opening of a body lumen to be closed.

FIGS. 13A-13I illustrate one implementation of a method of using the suturing device 300 to close an opening 210 in a body lumen 200. The method can include inserting the suturing device 300 in a distal direction into the body lumen 200. This can be accomplished with or without the use of a guidewire. FIGS. 13A-13I illustrate an example in which a guidewire 202 is used. It should be appreciated that, although the tissue tract 208 is illustrated at approximately 90° relative to the body lumen, the tissue tract 208 can be oriented at any number of suitable angles, which can vary from one embodiment to the next. For example, the tissue tract 208 can be oriented at a 45° relative to the body lumen 200.

Figure 13A:
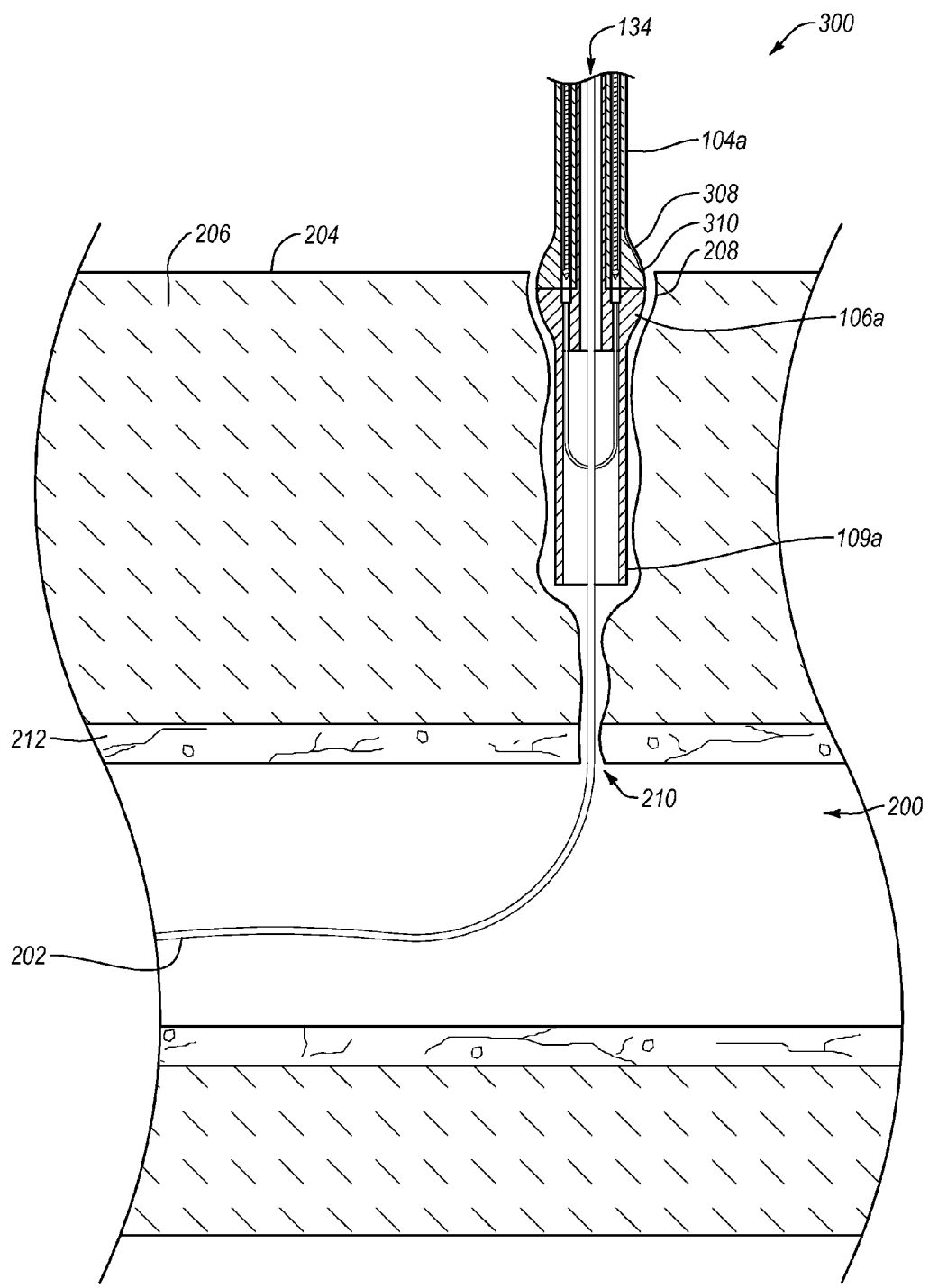
FIGS. 13A-13I illustrate cross-sectional views of a body lumen, showing a method for closing an opening in the wall of the body lumen using the suturing device of FIG. 10A.
Figure 13B:
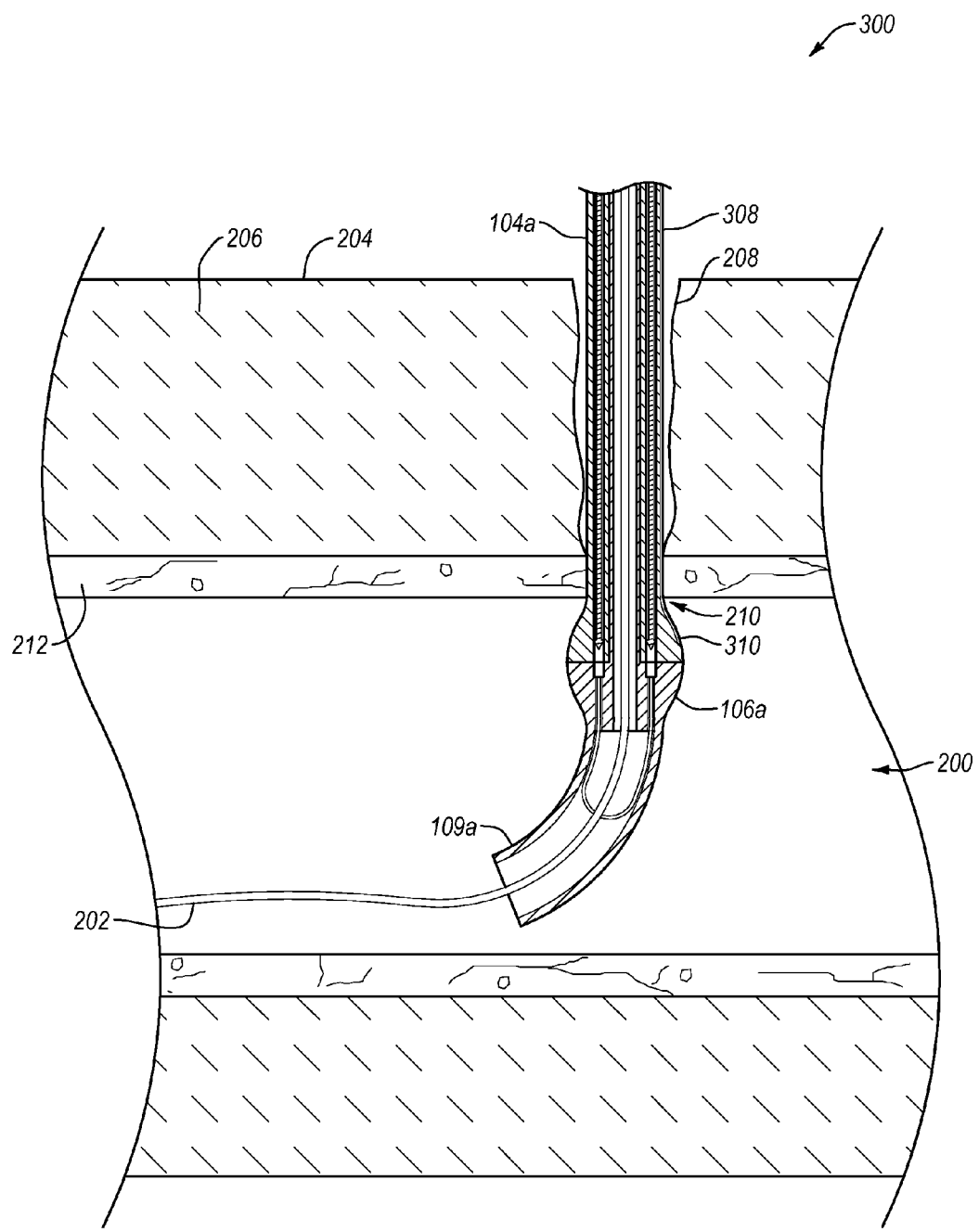

As shown by FIG. 13A, the guidewire 202 may enter the body lumen 200 through an opening or puncture site 210 formed in the body lumen wall 212. The guidewire 202 may extend along the body lumen 200. As illustrated by FIGS. 13A-13B, the flexible guidebody 109a and the guidewire lumen 134 can be advanced over the guidewire 202 in a monorail fashion, so that the guidewire 202 helps direct the suturing device 300 along the tissue tract 208 into the body lumen 200 through the opening 210.

As shown by FIGS. 13A-13B, the suturing device 300 can be slowly advanced until the position port 310 passes by the body lumen wall 212. Once past the body lumen wall 212, blood pressure can cause blood to flow into the position port 310, proximally through the indicator lumen 308 to the position indicator (FIGS. 10A-11B). In alternative implementations, blood can pass out of the end of the indicator lumen 308, notifying the medical practitioner that the foot 106a is in a position within the body lumen 202, and is ready for deployment.

Figure 13C:
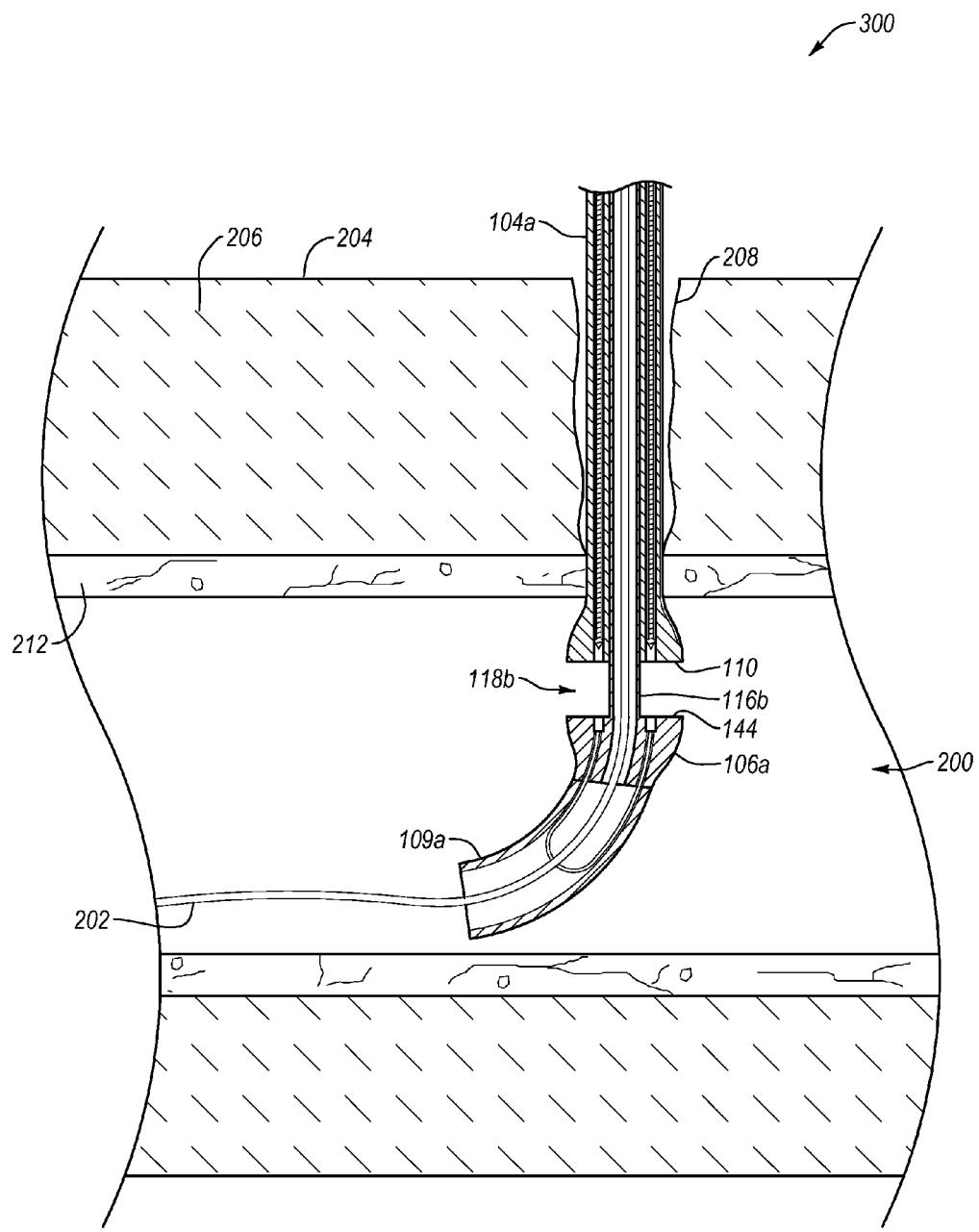

When the foot 106a is positioned within the body lumen 202, the medical practitioner can slide the foot actuation mechanism 302 distally along the handle 112a (FIGS. 10B and 11B), thereby causing the foot 106a to distally separate from the distal end 110 of the shaft 104a, as shown by FIG. 13C. In other words, the foot 106a can be articulated from a first configuration, in which the tissue location surface 144 of the foot 106a is abutted against the distal end 110 of the shaft 104a, to a deployed position, in which the tissue location surface 144 of the foot 106a is distally separated from the distal end 110 of the shaft 104a. As illustrated by FIG. 13C, by deploying the foot 106a, a tissue port 118b can be opened between the foot 106a and the shaft 104a. Once in the deployed position, the medical practitioner can compress a locking mechanism 324 (FIGS. 12A and 12B) to lock the foot 106a relative to the shaft 104a.

Figure 13D:
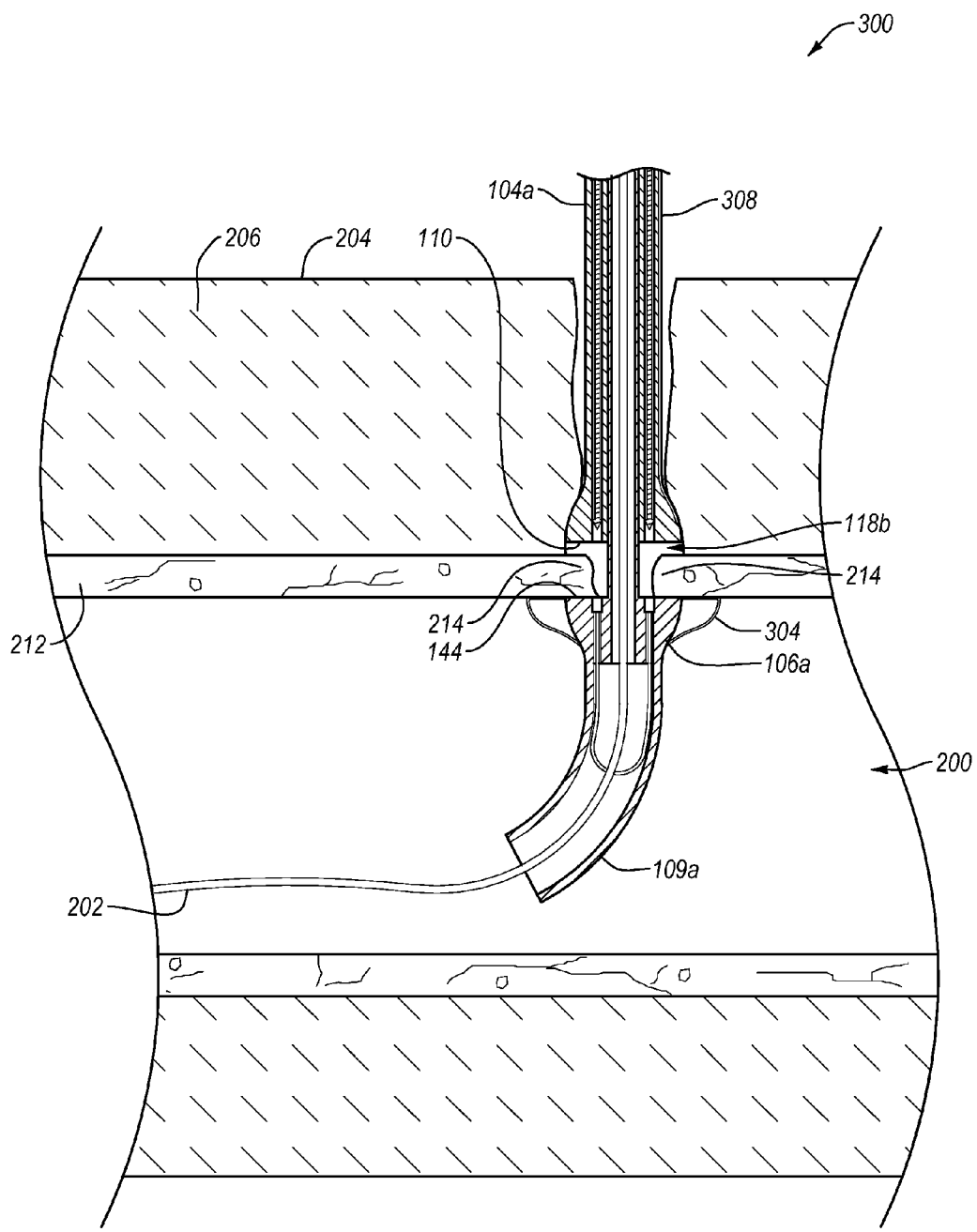

As shown by FIG. 13D, the medical practitioner can optionally inflate the one or more balloons 304. The balloons 304 can effectively increase the surface area of the tissue location surface 144 of the foot 106a. The medical practitioner can then slowly retract the suturing device 300 until resistance is felt when the tissue location surface 144 and/or the balloons 304 abut against the inner surface of the body lumen wall 212. By so doing, the distal end 110 of the shaft 104a can pass back through the opening 210 in the body lumen wall 212.

Figure 13E:
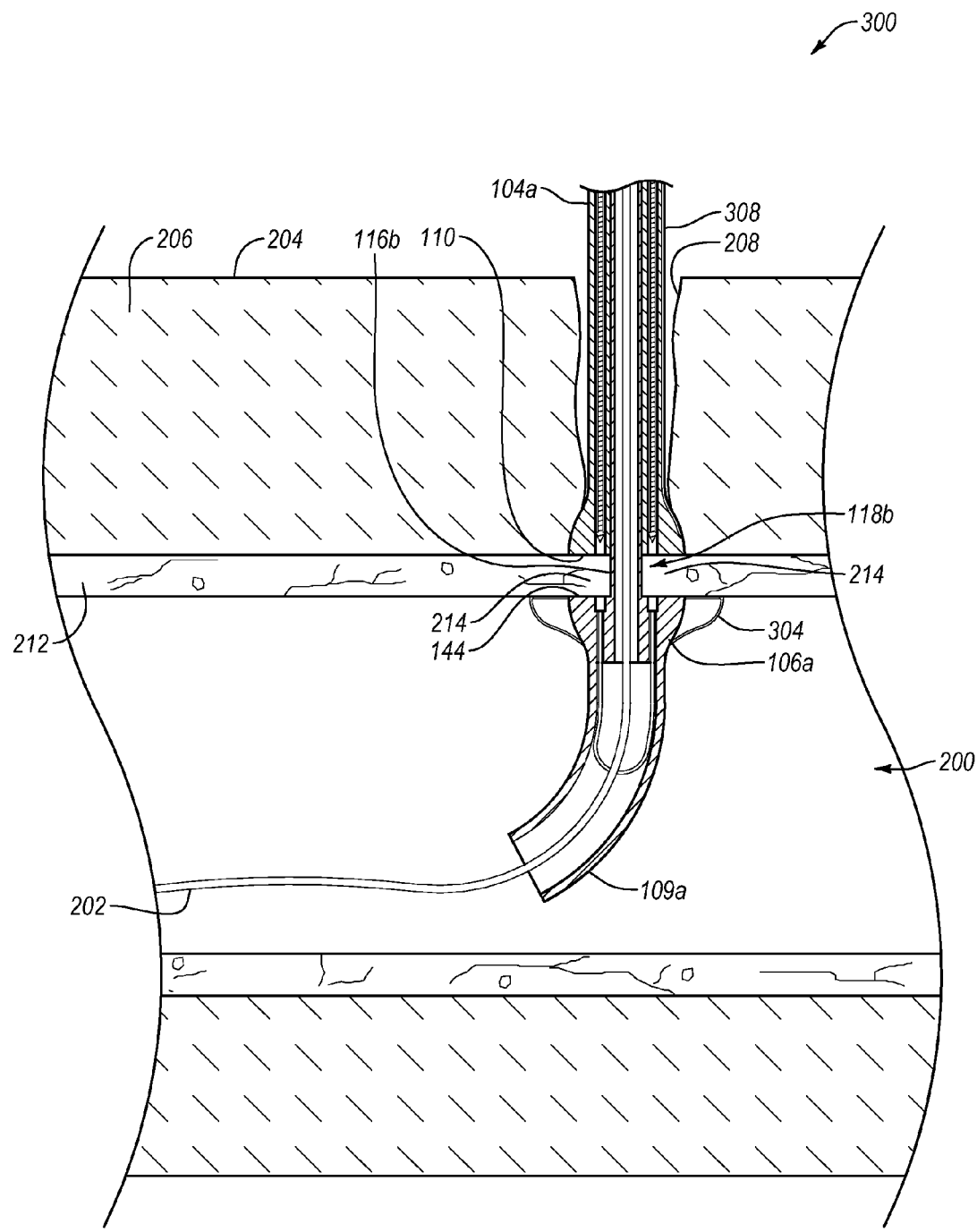

Once the shaft 104a is located on the proximal side of the body lumen wall 212, and the foot 106a is positioned on the distal side of the body lumen wall 212, the tissue 214 of the body lumen wall 212 adjacent the opening 210 can at least partially rebound or otherwise extend into the tissue port 118b, as shown by FIG. 13D. At this point, with the foot 106a locked in place, the medical practitioner can disengage the locking mechanism 324 (FIGS. 12A-12B). After the locking mechanism 324 is disengaged, the biasing member 318 (FIG. 10A), if included, can draw the shaft 104a and the foot 106a together. Otherwise, the medical practitioner can manually draw the shaft 104a and the foot 106a together using the foot actuation mechanism 302. The action of the foot 106a and the shaft 104a compressing toward each other can draw the tissue 214 further into the tissue port 118b, as depicted in FIG. 13E. In other words, the distal surface 110 of the shaft 104a and the tissue location surface 144 of the foot 106a can draw or push the tissue 214 into the tissue port 118b toward the spinal member 116b.

Figure 13F:
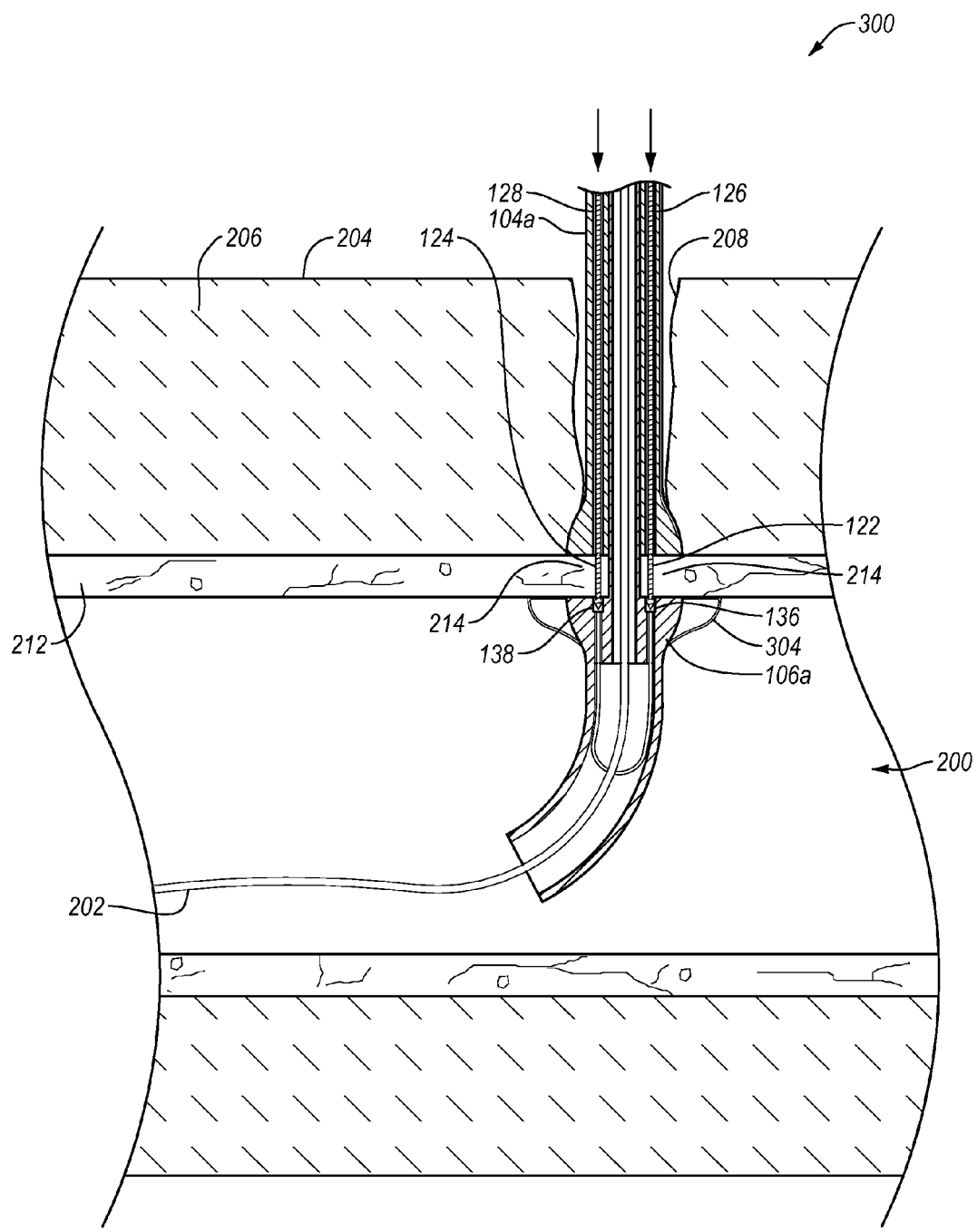

Next the medical practitioner can optionally lock the foot 106a in place relative to the shaft 104a using the locking mechanism 324 (FIGS. 12A and 12B). If the suturing device 300 includes a biasing member 318, the foot 106a may not be locked in place at this point. In any event, once the tissue 214 is positioned within the tissue port 118a, the needles 122, 124 can be deployed as shown in FIG. 13F. In particular, needles 122, 124 can be advanced in a distal direction within the needle lumens 126, 128, out of the needle exit openings 130, 132, distally across the tissue port 118a through the tissue 214, and into the needle capture devices 136, 138, as indicated by the arrows of FIG. 13F. This can be done by pushing the needle actuation handle 114a into the handle 112a (FIGS. 10A and 11A). The needles 122, 124 and needle capture devices 136, 138 can then be withdrawn out of the foot 106a, proximally across the tissue port 118b through the tissue 214, and out of the proximal end suturing device 300, as depicted by the arrows in FIG. 13G. One will appreciate that withdrawing the needles 122, 124 and needle capture devices 136, 138 can at least partially withdraw the proximal ends of the suture 140 from the foot 106a, allowing the ends of the suture 140 to be retrieved by the medical practitioner.

Figure 13G:
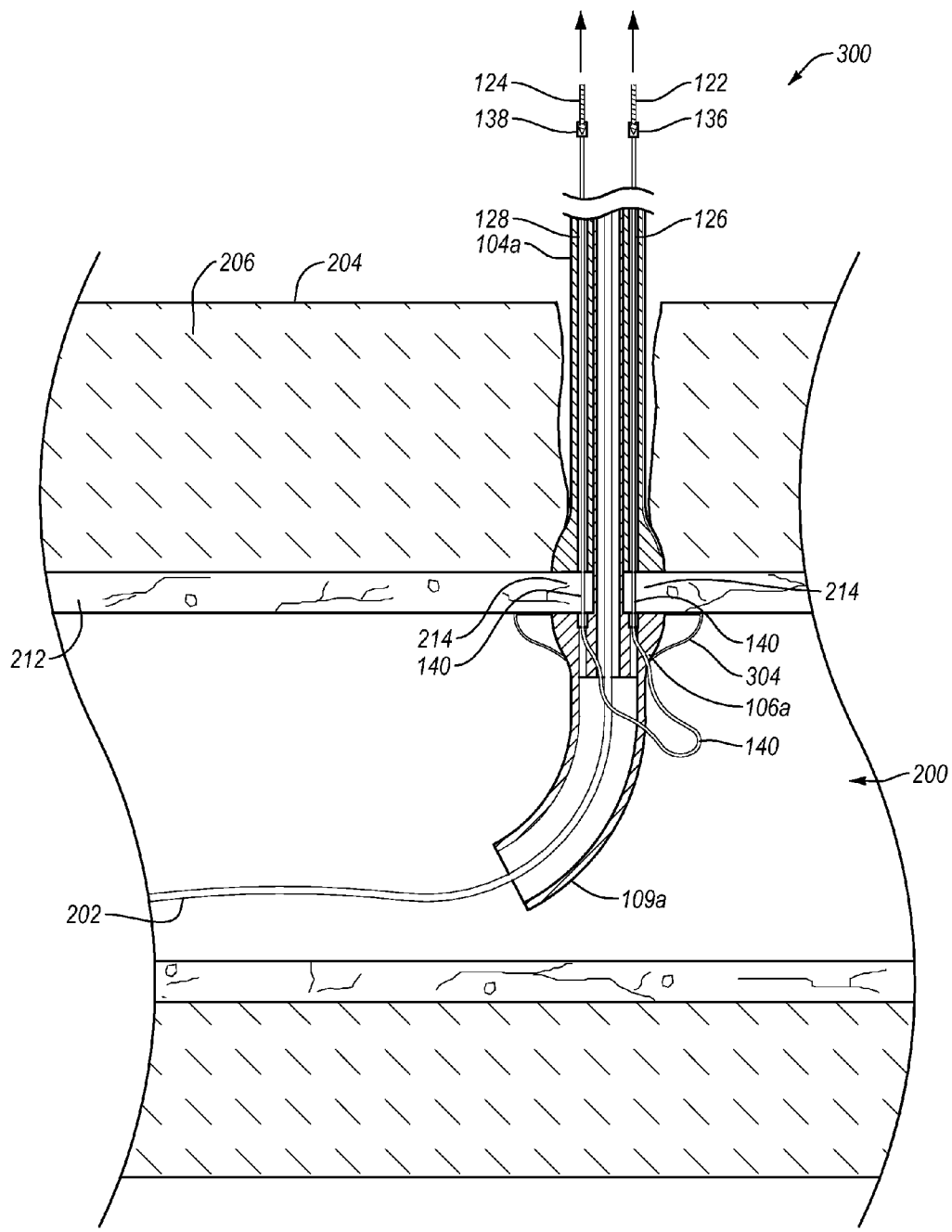

Furthermore, as shown by FIG. 13G, as the needles 122, 124, are withdrawn, the distal end of the suture 140 (i.e., the suture loop) can be pulled from the guidebody 109a and foot 106a via the suture exit slot 160a.

Figure 13H:
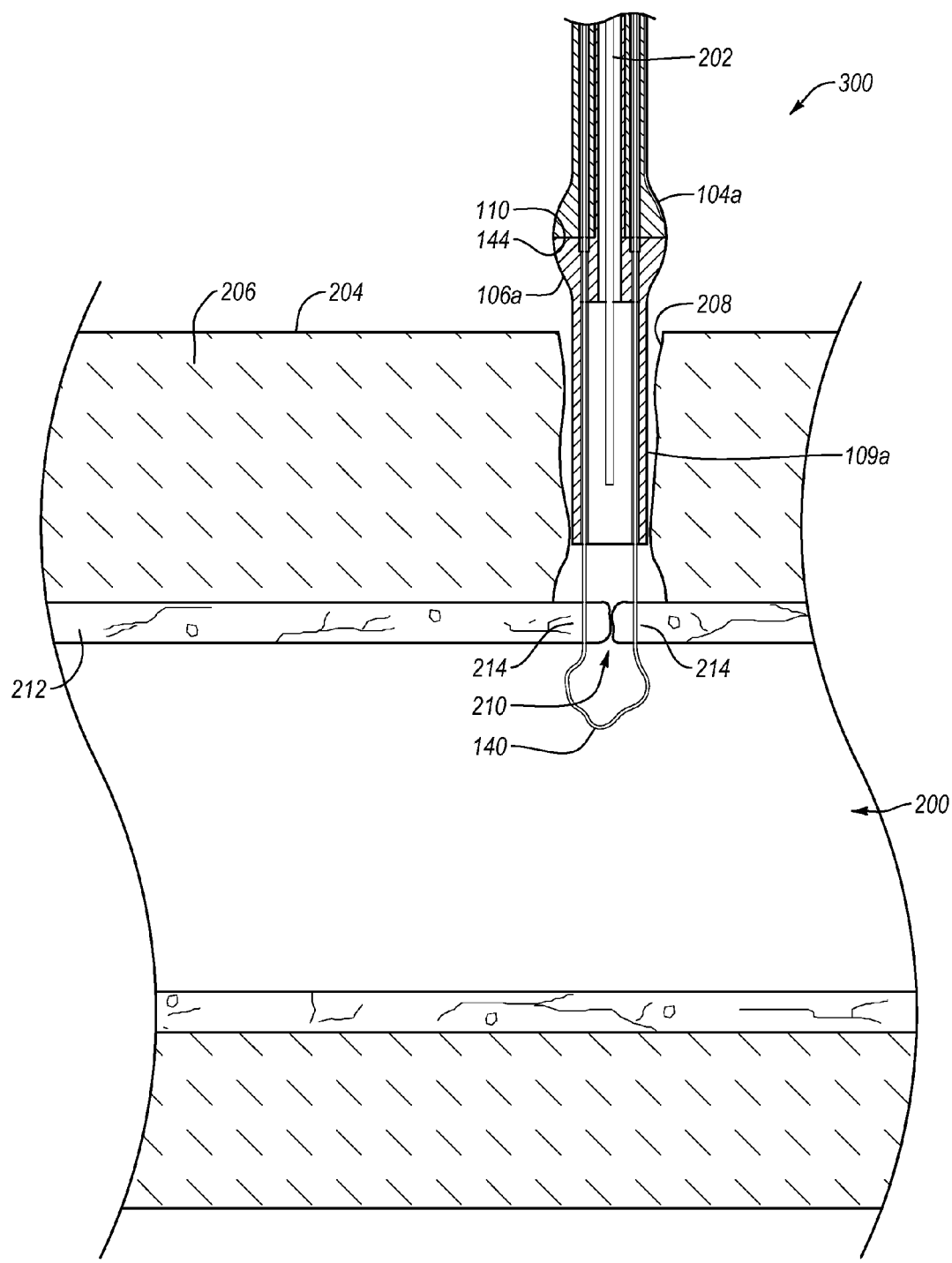
Figure 13I:
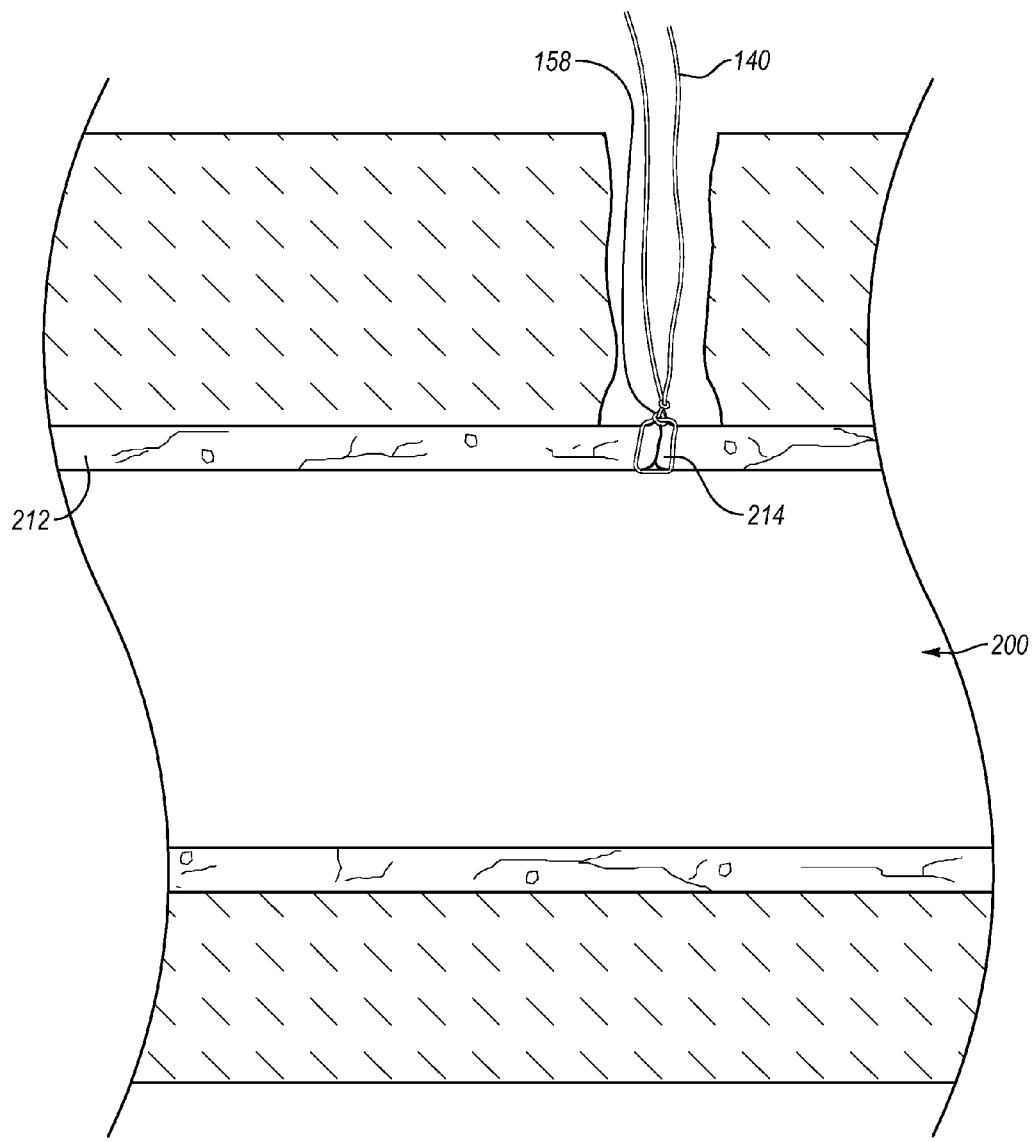

At this point, or before or after, if desired, the medical practitioner can withdraw the guidewire 202 from the body lumen 200 and the suturing device 300, as shown by FIG. 13H. FIG. 13H illustrates that the suturing device 300 can then be withdrawn from the body lumen 200 and out of the tissue tract 208. The medical practitioner can articulate the foot 106a from the deployed position to the first position using the foot actuation mechanism 302 either before or during the withdrawal of the suturing device 300. Once the suturing device 300 has been removed, the suture 140 can be employed to close the opening 210 in the body lumen 200, as shown by FIG. 13I. In particular, a surgical knot 158 can be tied thereby closing the opening in the body lumen 200.

In one or more embodiments, the foot of the suturing device may be interchangeable and may be selected and coupled to a particular shaft based on the size of the opening in the body lumen that is intended to be closed. Thus, the user can select a suitable foot that corresponds with the opening in the body lumen. For example, a larger sized foot may be selected for closing larger openings, and a smaller sized foot can be chosen for closing smaller openings in the body lumen.

The larger sized foot can have tissue ports located or formed thereon such that the tissue surrounding the larger opening may be captured within the tissue ports. For instance, the tissue ports of the larger foot may be located at an appropriate distance from the center axis of the suturing device, such as to correspond with the dimensions of the opening that is intended to be closed by the suturing device. Similarly, the smaller sized foot may have tissue ports that accommodate capturing the tissue surrounding the smaller openings in the body lumen. Additionally, the needle capturing devices, located in the foot of the suturing device, may be positioned at an appropriate distance from the center axis of the suturing device, such that the needle capturing devices are located over the tissue surrounding the opening, and the needles may pass through the tissue and into the needle capturing device.

Moreover, while the foot of the suturing device may be interchangeable to accommodate closure of a particular sized opening in the body lumen, in some embodiments, the shaft of the device may remain unchanged irrespective of the particular foot that is being used. The shaft may be adjusted to correspond with the particular foot being used in the suturing device. More specifically, the needle lumens of the shaft may be adjusted and/or may be moved to a position that would allow the needles to exit the needle lumens and pass through the tissue. Furthermore, after adjusting the shaft, the needles can be aligned with the needle capture devices located in the corresponding foot. For example, adjusting the shaft can include moving the needle exit openings outward, so the needles exit the shaft at locations that allow the needles to couple with the needle capture devices.

In further embodiments, the suturing device may include a guide member that secures the foot. The guide member can be slidably positioned within the shaft. Thus, the foot can move together with the guide member, as the guide member slides or moves relative to the shaft of the suturing device. The user may position the guide member and at least a portion of the foot in the opening of the body lumen, such that the foot and/or the guide member can capture at least a portion of the tissue surrounding the opening.

In some embodiments, the needles can be housed in the shaft, as described above. However, the guide member also may house the needles and at least a portion of the suture. Thus, the needles located in the guide member can be advanced proximally, toward the shaft and can enter needle lumens in the shaft. Furthermore, the foot may have one or more channels or lumens that can guide the needles from the guide member and toward the needle openings (leading up to the needle lumens) in the shaft.

Figure 14:
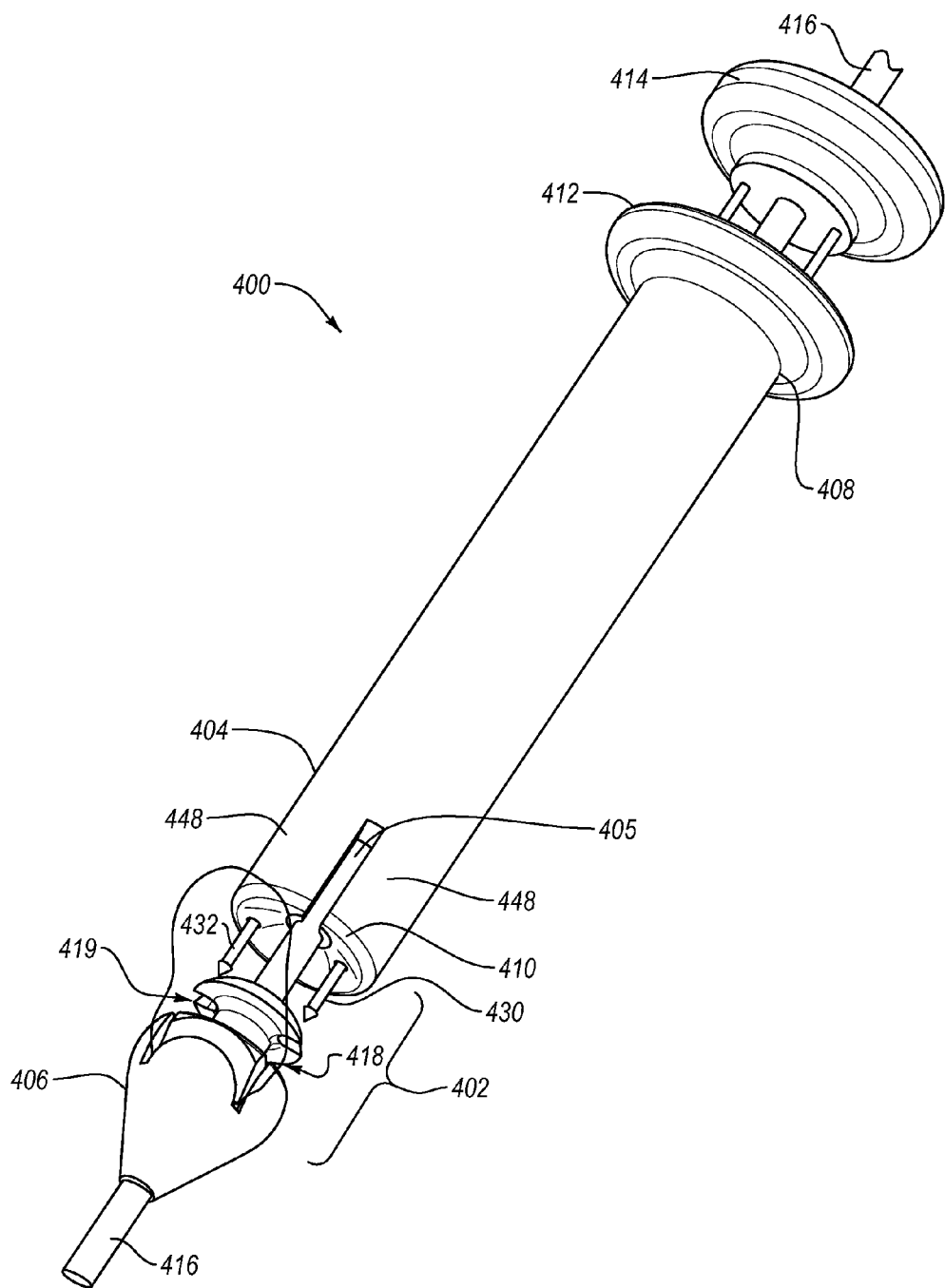
FIG. 14 illustrates a perspective view of a suturing device with a replaceable foot in accordance with one implementation of the present invention.

Referring now to FIG. 14 which illustrates one embodiment of a suturing device 400 that incorporates an interchangeable foot. The suturing device 400 may be substantially the same as any one of the suturing devices 100, 100a, 300 (FIGS. 1-13I), and combinations thereof, except as described below. The suturing device 400 may have a body 402 that includes a shaft 404 and an interchangeable foot 406. As noted above, the foot 406 can be removable and replaceable. The foot 406 also can be chosen by the user based on the size of the opening in the body lumen that is intended to be closed.

The shaft 404 may have a proximal end 408 and a distal end 410, the proximal end 408 being closer to the user of the suturing device 400. Additionally, the suturing device 400 can have a handle 412, which can help the user to grasp and hold the suturing device 400 during the operation thereof. The suturing device 400 also may have an actuation handle 414 that may actuate the suturing device 400 (e.g., by engaging the needles with the needle capture devices, as further described below).

In some embodiments, as noted above, the foot 406 is coupled to a guide member 416. The guide member 416, in turn, may be slidably located within the shaft 404. Accordingly, the foot 406 may move together with the guide member 416 relative to the shaft 404. For instance, the foot and the guide member can move in a distal and/or proximal direction along the center axis of the shaft 404.

Furthermore, the user may select an appropriately sized foot 406, for example, based on the size of the opening in the body lumen. Thus, suturing device 400 can have an interchangeable foot 406, such that the foot 406 of a first size may be selected, coupled to, and/or removed from the guide member 416. The foot 406 also may be substituted for another foot of a different size and/or shape. Similarly, the foot 406 and the guide member 416 (as a coupled pair or a single unit) may be selected and exchanged as the single unit. In any case, the user may choose and/or replace a previously chosen foot 406, such that the foot 406 is appropriately sized relative to the opening in the body lumen.

The foot 406 can have one or more tissue ports 418, which can accept tissue surrounding the opening in the body lumen. As described above, the size of the foot 406 can be selected based on the size of the opening that is intended to be closed. Hence, the size, locations, and shapes of the tissue ports 418 may correspond with a particular size of the opening. In other words, the tissue ports 418 can be sized such that tissue surrounding the opening fits within the tissue ports 418.

In some embodiments, the shaft 404 can house multiple needles, such as needles 430, 432. The 430, 430 can pass through the tissue ports 418, thereby passing through the tissue surrounding the opening. To allow the needles 430, 432 to pass through the tissue ports 418, the foot 406 can have clearance slots (or holes) 419.

In one or more embodiments, the shaft 404 can have multiple leafs 448, which can be located near the distal end 410 of the shaft 404. For example, the shaft 404 can have multiple slots 405, which can divide or section the distal portion of the shaft 404, thereby forming multiple leafs 448. As further described below, the leafs 448 can flex outward thereby flexing the needles 430, 432 to a predetermined angle. As such, the user can adjust the size of the shaft 404 by flexing the leafs 448, such as to facilitate closure of an opening of a particular size. The leafs 448 also can flex inward (i.e., substantially back to their original positions).

Figure 15A:
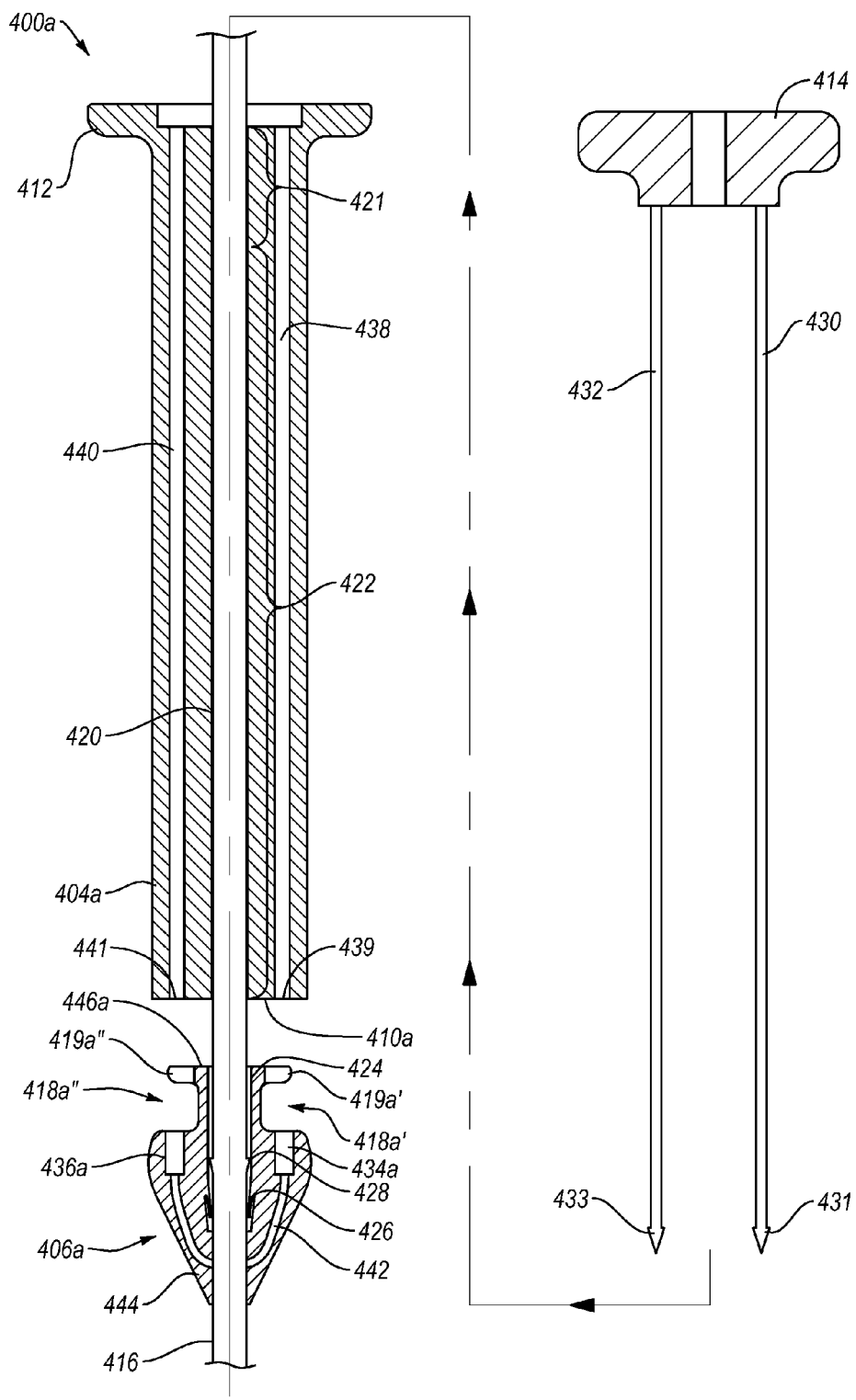
FIG. 15A illustrates a cross-sectional view of a suturing device with a replaceable foot in accordance with one implementation of the present invention.

Moreover, the shaft 404 also may have different configurations, which may depend on the particular foot 406 that is used. For instance, as illustrated in FIG. 15A, a suturing device 400a can have a shaft 404a that can be used together with a foot 406a. Similar to the suturing device 400 (FIG. 14), the suturing device 400a may be substantially the same as any one of the suturing devices 100, 100a, 300, and combinations thereof (FIGS. 1-13I), except as described below. In some embodiments, the suturing device 400a can have a guide lumen 420 that can be configured to accept the guide member 416.

Specifically, the guide lumen 420 may be sized such that guide member 416 can freely slide in the proximal and/or distal direction along a length of the guide lumen 420 (i.e., the guide member 416 can have a slip fit within the guide lumen 420). In some embodiments, at least a portion of the guide lumen 420 can have a clearance (e.g., approximately 0.005") between the outside wall of the guide member 416 and the wall of the guide lumen 420. It should be noted that the clearance can vary from one embodiment to another.

Also, in one or more embodiments, at least a portion of the guide lumen 420 can have friction or interference fit with the guide member 416. For example, an interference-fit portion 421 of the guide lumen 420 can have an interference fit, while a slip-fit portion 422 can have a slip fit with the guide member 416. Consequently, the user may force the guide member 416 along the guide lumen 420, such that the guide member 416 slides along the guide lumen 420 when the user applies a force thereto. When the user stops applying force to the guide member 416, however, the guide member 416 may remain fixed within the guide lumen 420. The lengths of the interference-fit portion 421 and/or the slip-fit portion 422 may vary from one implementation to another.

In some implementations, the length of the interference-fit portion 421 or of the slip-fit portion 422 may be the same as the length of the guide lumen 420. Furthermore, the clearance between the guide member 416 in the guide lumen 420 along the slip fit portion 422 can vary and can be greater or less than 0.005". Accordingly, the ease of movement or the amount of force necessary to move the guide member 416 along the guide lumen 420 also can vary from one embodiment to another.

Additionally or alternatively, the suturing device 400a can include a clip or clamp that can secure the guide member 416 to the shaft 404a, to prevent relative movement thereof. Also, the user can hold the guide member 416 during the procedure, in order to keep the guide member 416 and/or the foot 406a stationary relative to the shaft 404a. In any event, the guide member 416 and the foot 406a can remain fixed at a desired position relative to the shaft 404a.

Once the user selects an appropriately sized foot, such foot (e.g., the foot 406a) can be coupled to the guide member 416. For example, the foot 406a can have an attachment lumen 424 that can accept the guide member 416. In at least one embodiment, the foot 406a also may have one or more snap-in features 426. The snap-in features 426 may correspond with protrusions 428 on the guide member 416. Thus, the foot 406a can slide over the guide member 416, such that the snap-in features 426 snap over the protrusions 428, thereby securely coupling the foot 406a to the guide member 416.

It should be appreciated that other implementations may include various types of connections between the foot 406a and the guide member 416, which may permanently or removably couple the foot 406a to the guide member 416. For example, the foot 406a and the guide member 416 can have corresponding locking tapers, such as the foot 406a can be coupled and locked to the guide member 416. Additionally or alternatively, the foot 406a and the guide member 416 may form an interference fit therebetween, such that the foot 406a is securely coupled to the guide member 416. Moreover, in some instances, the foot 406a may be permanently bonded to the guide member 416, such as by gluing or welding the foot 406a to the guide member 416.

The guide member 416 and, consequently, the attachment lumen 424 can have a non-circular cross-sectional shape, which can radially orient the foot 406a relative to the shaft 404a. In other words, the corresponding cross-sectional shapes of the guide member 416 and the attachment lumen 424 may prevent the foot 406a from rotating about the guide member 416. For instance, the guide member 416 can have a non-cylindrical shape (e.g., partially elliptical and partially circular shape, square, etc.), such that the foot 406a can fit over the guide member 416 only in a single, predetermined axial orientation. Similarly, the cross-sectional shape of the guide lumen 420 and of the attachment lumen 424 can correspond with the cross-sectional shape of the guide member 416. Thus, radial orientation of the shaft 404a, foot 406a, and guide member 416 can be fixed relative to each other.

Fixing the radial orientation of the foot 406a (e.g., about the center axis of the suturing device) relative to the shaft 404a can ensure that the needles can engage the needle capture devices located in the foot 406a. In other embodiments, the foot 406a can be radially fixed with respect to the shaft 404a using various other connections. For example, as described above, the foot 406a may be permanently coupled to the guide member 416. Accordingly, the foot 406a may have a permanent radial orientation with respect to the guide member 416.

In one or more embodiments, the guide member 416 can extend past a distal end of the foot 406a. Accordingly, the user can feed at least a portion the guide member 416 through the opening in the body lumen. As the guide member 416 is fed through the opening an into the body lumen, the foot 406a can remain attached to and can move together with the guide member 416. In some instances, the foot 406a may remain outside of the patient's body, while the guide member 416 is initially positioned within the body lumen.

Additionally or alternatively, the suturing device 400a also can include a guidewire (e.g., similar to the guidewire 202 (FIG. 7A)), which can pass through the guide member 416. Hence, first the guidewire can be inserted through the opening and into the body lumen, and, subsequently, the guide member 416 together with the foot 406a can slide over the guidewire and moved into position within the opening. Consequently, in some embodiments, the guide member 416 need not and may not protrude past the distal end of the foot 406a.

Similar to the suturing devices described above, in connection with FIGS. 1-13I, the suturing device 400a also can include multiple needles, such as needles 430, 432 coupled to the actuation handle 414. Such needles 430, 432 (more specifically, respective piercing ends 431, 433 of the needles 430, 432) can engage and couple to corresponding needle capture devices 434a, 436a. The needle capture devices 434a, 436a can be similar to or the same as the needle capture devices 136, 138 (FIGS. 3, 4). In some embodiments, the needle capture devices 434a, 436a can be positioned substantially parallel to the center axis of the suturing device 400a. Alternatively, as described in more detail below, the needle capture devices 434a, 436a can be oriented on an angle relative to the center axis. The needles 430, 432 can slide in the proximal and/or in the distal direction within corresponding needle lumens 438, 440, located in the shaft 404a. Moreover, the needles 430, 432 can exit the shaft 404a at respective needle exit openings 439, 441, which may be located at the distal end 410a. In other words, the needle lumens 438, 440 can terminate at the needle exit openings 439, 441, at the distal end 410a for the shaft 404a.

The needle capture devices 434a, 436a can be connected to each other by a length of suture 442. The length of suture 442 can be located in and/or secured to the foot 406a (e.g., as described above in connection with FIGS. 1-13I). Thus, as the needles 430, 432 move in the proximal direction, the length of suture 442 can be removed and/or detached from the foot 406a. Moreover, after the length of suture 442 is removed and/or detached from the foot 406a, the suturing device 400a can be removed from the opening in the body lumen, without interfering with the length of suture 442.

The foot 406a can have a distal end 444 and a proximal end 446a. In some embodiments, the distal end 444 can have a substantially conical shape, which can facilitate entry of the foot 406a into to the opening in the body lumen. In other embodiments, however, the distal end 444 of the foot 406a can have other suitable shapes, such as semi-spherical, spherical tapered, etc. Hence, as noted above, the shape and size of the distal end 444 of the foot 406a can vary from one embodiment to the next, which may depend on the shape and size of the opening in the body lumen.

Similarly, the proximal end 446a and the distal end 410a also can have various shapes, which may correspond with each other. For instance, the proximal end 446a can be substantially flat and can correspond with a substantially flat distal end 410a. In other embodiments, the proximal end 446a and/or the distal end 410a can have other suitable shapes.

Additionally, as described above, the foot 406a can be fixed to the guide member 416. Accordingly, the user can move the foot 406a with respect to the shaft 404a by moving the guide member 416. Similarly, as the guide member 416 moves within the guide lumen 420, when the foot 406a is coupled to the guide member 416, the foot 406a also can move relative to the shaft 404a, either in the proximal direction (i.e., toward the user) or in the distal direction.

As also noted above, the guide member 416 can be secured at a desired position within the guide lumen 420. Thus, the foot 406a can be secured at a desired position with respect to the shaft 404a. For example, in a pre-deployed configuration the proximal end 446a of the foot 406a can be separated by a distance from the distal end 410a of the shaft 404a. By contrast, in the deployed configuration, the proximal end 446a can abut the distal end 410a. The foot 406a can move toward the shaft 404a, such that the proximal end 446a abuts the distal end 410a, and the foot 406a can remain in such the (deployed) position. Thus, in the embodiment illustrated in FIG. 15A, in the deployed configuration, the flat proximal end 446a can abut the flat distal end 410a and the suturing device 400a can remain in such configuration. As the guide member 416 moves in the distal direction, the proximal end 446a can move away from the distal end 410a.

As the foot 406a enters the opening in the body lumen, the tissue surrounding the opening can be captured in the tissue ports of the foot 406a. In one embodiment, the foot 406a can have multiple tissue ports, such as tissue ports 418a', 418a". In other embodiments, the foot 406a can have a single tissue port, which can receive and capture substantially all of the tissue surrounding the opening. For example, the tissue port can surround the entire perimeter of the foot 406a. Additionally, (as described above) the foot 406a can have clearance slots 419a', 419a" that can allow the needles 430, 432 to pass through the tissue ports 418a', 418a".

Figure 15B:
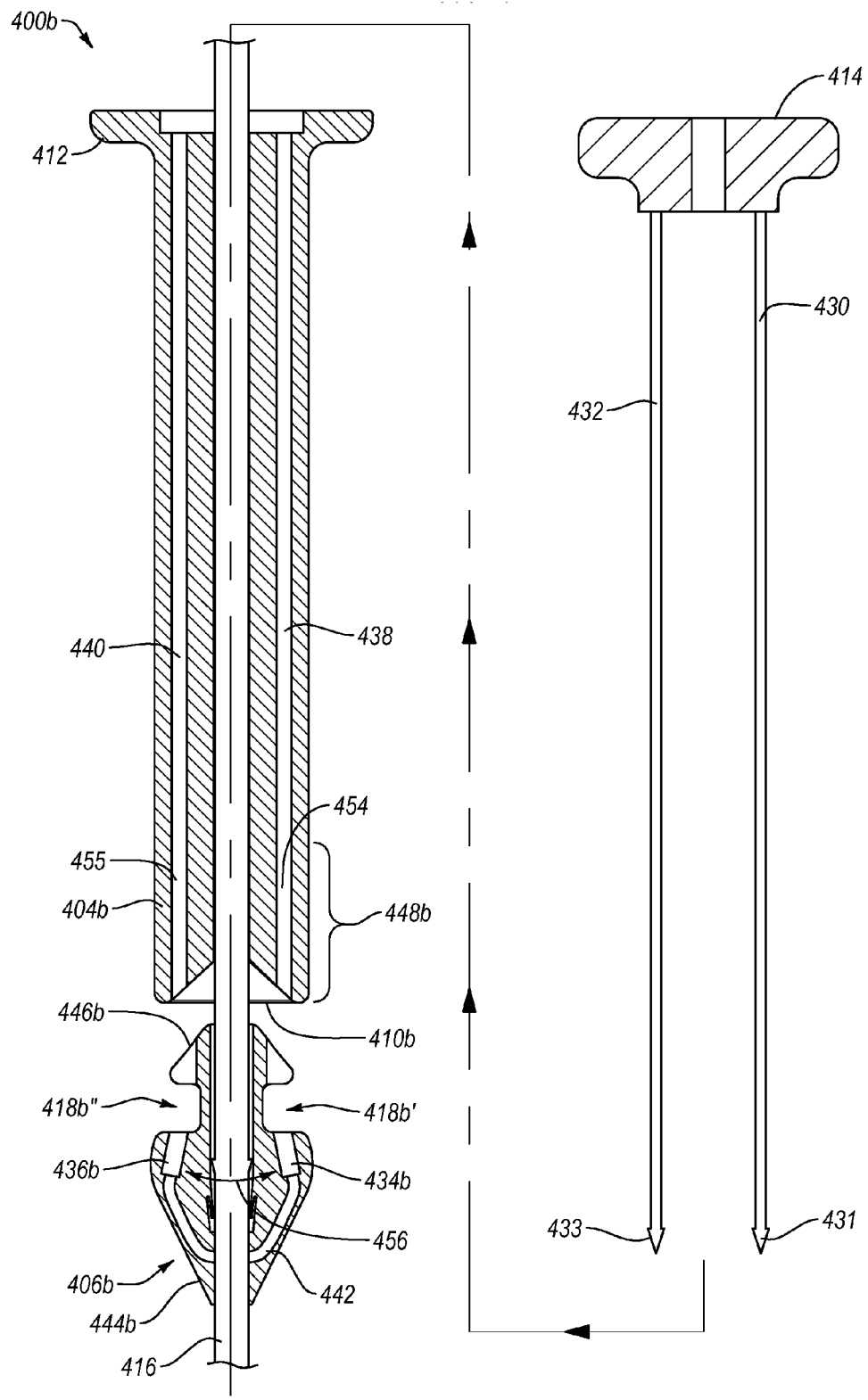
FIG. 15B illustrates a cross-sectional view of a suturing device with a replaceable foot in accordance with another implementation of the present invention.

The distal end of the shaft and the proximal end of the foot of the suturing device also can have non-flat configurations. For instance, as illustrated in FIG. 15B, a suturing device 400b can have shaft 404b that has a non-flat distal end 410b. The suturing device 400b may be substantially the same as the suturing device 400a (FIG. 15A), except as otherwise described herein. The suturing device 400b can have a foot 406b that can have a proximal end 446b. As described above, the shape of the proximal end 446b can correspond with the shape of the distal end 410b.

More specifically, the foot 406b can have the proximal end 446b that has a tapered (conical) shape. The distal end 410b also can have a tapered shape (e.g., a cone-shaped or a tapered cavity in the distal end 410b). The tapered shape of the proximal end 446b can correspond with the tapered shape of the distal end 410b. For example, the tapered shapes of the corresponding proximal end 446b and distal end 410b can have an approximately 45° angle. An at least one other embodiment, however, the distal end 410b and of the proximal end 446b can have locking angle (e.g., 3° included angle) tapers, which can operate in a similar manner as a luer fitting. Accordingly, when the proximal end 446b is pressed into the distal end 410b, the proximal end 446b can be locked inside of the distal end 410b, thereby securing the foot 406b to the shaft 404b.

Alternatively, the angle of the tapered shapes of the distal end 410b and/or of the proximal end 446b can be non-locking (e.g., self-releasing angle). Consequently, in some embodiments the proximal end 446b may not be locked inside of the distal end 410b. However, the user can secure the proximal end 446b within or abutting the distal end 410b by securing the guide member 416 with respect to the shaft 404b, as described above.

The shaft 404b can have multiple leafs, such as the leaf leafs 448b, which can move outward in response to the pressure applied by the taper of the proximal end 446b on the taper of the distal end 410b. In other words, as the proximal end 446b moves deeper into the distal end 410b, the leafs 448b can flex outward to accommodate the proximal end 446b within the distal end 410a.

In at least one embodiment, the foot 406b can have a stop surface, which can define the most proximal portion of the proximal end 446b. The stop surface can determine the maximum depth of entry of the proximal end 446b into the distal end 410b. More specifically, the stop surface can bottom out on a corresponding limiting surface in the distal end 410b (not shown). Thus, as the stop surface presses against the limiting surface in the distal end 410b, the proximal end 446b reaches a predetermined depth within the distal end 410b.

Consequently, at a predetermined depth, the foot 406b can flex the leafs 448b outward by a predetermined amount. More particularly, the leafs 448b can be flexed to form a predetermined angle therebetween and relative to the center axis of the suturing device 400b.

The suturing device 400b also can include needle lumens 438, 440. Particularly, the needle lumens 438, 440 can guide the needles 430, 432 toward the foot 406b, as the user pushes the actuation handle 414 in the distal direction. Furthermore, in some embodiments, needle lumen portions 454, 455 can be located within the leafs 448b. Thus, when the leafs 448b flex outward to a predetermined angle, the needle lumen portions 454, 455 also can flex outward to a predetermined angle.

As the needles 430, 432 move within the corresponding needle lumens 438, 440 and enter the needle lumen portions 454, 455 located in the leafs 448b, the needles 430, 432 also can be at least partially flexed to a predetermined angle. Hence, the piercing ends 431, 433 can move toward and approach the foot 406b at a predetermined angle (i.e., not parallel to each other). Accordingly, in one or more embodiments, the foot 406b can house needle capture devices 434b, 436b that are positioned at an angle 456 relative to each other and relative to the center axis of the suturing device 400b. More specifically, the angle 456 can be greater than zero (i.e., orientations of the needle capture devices 434b, 436b may be non-parallel to each other).

Furthermore, the angle 456 can be the same as the angle formed between the needles 430, 432, when the leafs 448b flex outward to a predetermined angle. Thus, as the needles 430, 432 move through the portions 450, 454, the needles 430, 432 can align with the needle capture devices 434b, 436b. Consequently, movement of the actuator handle 414 can move the needles 430, 432 in the distal direction, such as to engage the needle capture devices 434b, 436b. Particularly, the needles 430, 432 can pass through the clearance slots 419a', clearance slots 419a", pass through the tissue ports 418b', 418b", pass through the tissue surrounding the opening (as described below), and enter the needle capture devices 434b, 436b.

As noted above, the foot 406b can be chosen at least in part based on the size and/or shape of the opening in the body lumen. In at least one embodiment, the suturing device 400b can have the same shaft 404b for closing openings of different sizes, by choosing an appropriately sized corresponding foot 406b. For example, a first size of the foot 406b can have a distal end 444b sized and configured to enter the opening of a first size. Likewise, the tissue ports 418b', 418b" can be sized and configured to receive the tissue surrounding the first size opening. Furthermore, the needle capture devices 434b, 436b also can be located such that before entering the needle capture devices 434b, 436b, the piercing ends 431, 433 pass through the tissue surrounding the opening in the body lumen. Similarly, the foot 406b of a second size can have the distal end 444b, tissue ports 418b', 418b", and the needle capture devices 434b, 436b sized, configured, and located (as applicable to each) in a manner that allows the piercing ends 431, 433 to pass through the tissue surrounding the opening of a second size, and enter the needle capture devices 434b, 436b.

Thus, on the first size foot 406b, the stop surface 452 can be located at a first position, which can allow the proximal end 446b to enter into the distal end 410b and flex the leafs 448b and, consequently, the needle lumen portions 454, 455 to a first predetermined position (i.e., to a predetermined angle). The leafs 448b and the needle lumen portions 454, 455 at the first predetermined angle can correspond with the angle 456 of the first size foot 406b. Accordingly, when the suturing device 400b that has the first size foot 406b is in the deployed configuration, and the proximal end 446b is at its most proximal position with respect to the distal end 410b, the piercing ends 431, 433 can enter and engage the needle capture devices 434b, 436b.

Likewise, when the suturing device 400b that has the second size foot 406b is in the deployed configuration, and the proximal end 446b is at its most proximal position with respect to the distal end 410b, the piercing ends 431, 433 can enter and engage the needle capture devices 434b, 436b. As noted above, the needle capture devices 434b, 436b can be spaced farther apart from each other as compared with the first size foot 406b. The locations of the needle capture devices 434b, 436b and the angle 456 therebetween can correlate with the location of the stop surface 452, as the stop surface 452 can determine the predetermined angle at which the needles 430, 432 can exit the needle lumens 440, 438. Furthermore, positions and angles of the needle capture devices 434b, 436b and location of the stop surface 452 also can correlate with a particular size of the foot 406b, and, more specifically, with a particular size and shape of the distal end 444b. In any event, the suturing device 400b can accept the foot 406b of any size, in a manner that allows the piercing ends 431, 433 to engage the needle capture devices 434b, 436b located in the foot 406b of that particular size.

Figure 16A:
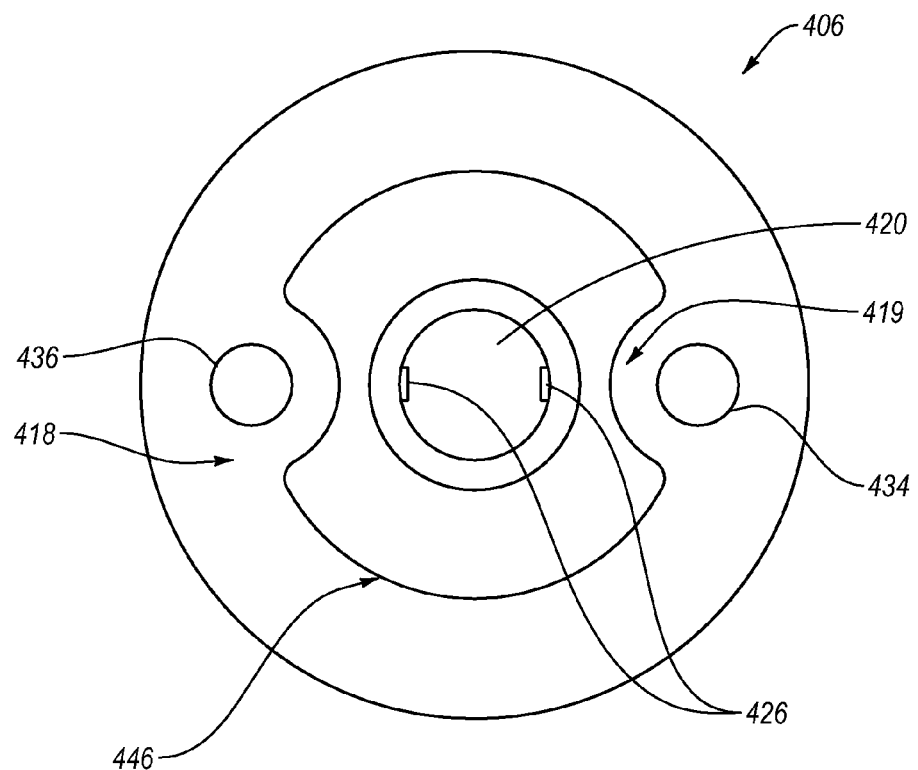
FIG. 16A illustrates a top view of a foot of a suturing device in accordance with one implementation of the present invention.

In some instances, the opening in the body lumen may have a substantially circular shape. Hence, the suturing device can incorporate a foot that has circular or cylindrically shaped tissue ports. Furthermore, the foot of the suturing device also can have but is not limited to a circular cross-section. For example, as illustrated in FIG. 16A, the foot 406 can have a substantially circular shape (as noted above the distal end of the foot 406 can be tapered or generally angled, to facilitate entry of the foot 406 and the tissue ports 418 into the opening).

Additionally, the foot 406 can have needle capture devices 434, 436 located around the tissue ports 418, in a manner that the piercing ends of the needles can pass through the tissue surrounding the opening in the body lumen, before entering the needle capture devices 434, 436. In other words, locations of the needle capture devices 434, 436 as well as positions thereof may depend on the particular size and shape of the foot 406 and of the tissue ports 418, which can correspond with the particular size and shape of the opening in the body lumen. In the embodiment illustrated in FIG. 16A, the foot 406 has two needle capture devices 434, 436. One will appreciate, however, that this disclosure is not so limited. More specifically, the foot 406 can have any number of needles capture devices positioned at different locations on the foot 406, which may vary from one embodiment to another. Similarly, the shaft can accommodate any number of needles that may correspond with the needles capture devices on or in the foot 406. Furthermore, the foot 406 can have a greater number of needles capture devices than the needles located in the shaft of the suturing device. In some embodiments, the guide lumen 420 also can have a substantially circular cross-sectional shape, which can accept correspondingly sized and shaped guide member.

Figure 16B:
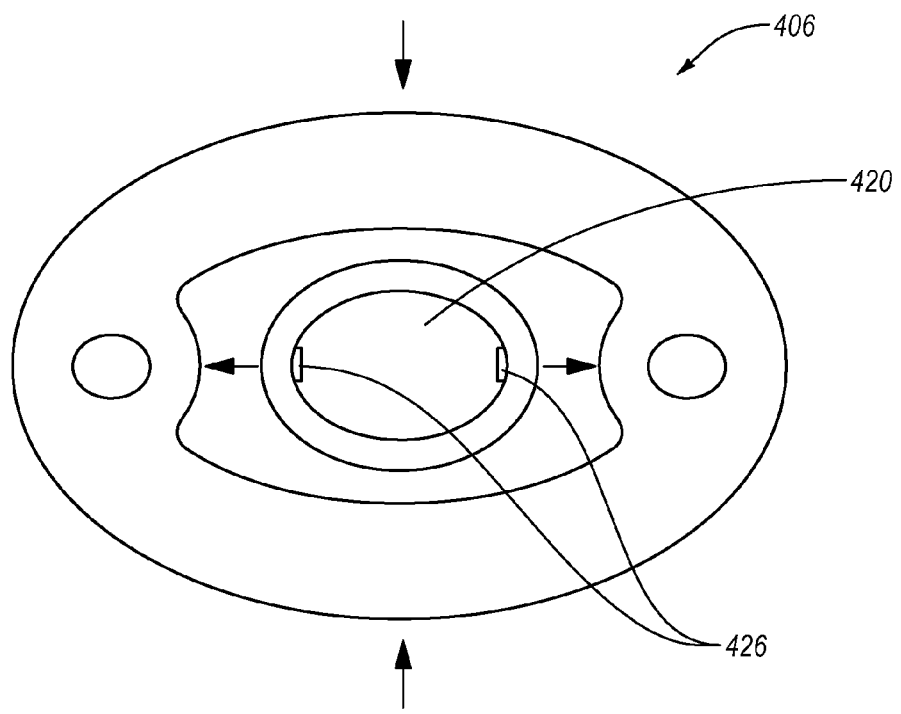
FIG. 16B illustrates a top view of the foot illustrated in FIG. 16B shown in a deformed state.

As noted above, the foot 406 also can have snap-in features 426 that can secure the foot 406 to the guide member. In some instances it may be desirable to remove the foot 406 from the guide number and/or to replace the foot 406 with the foot 406 of a different size. In at least one embodiment, the user can remove the foot 406 from the guide member by pressing on opposing sides of the foot 406, as illustrated with the arrows in FIG. 16B, such as to deform the foot 406. Particularly, the deformation caused by the pressure applied along an axis approximately perpendicular to the axis on which the snap-in features 426 lie can force the snap-in features 426 to move outward as indicated with the arrows. Consequently, as the snap-in features 426 move outward, the snap-in features 426 also move away from the corresponding protrusions on the guide member, thereby releasing the foot 406 from the guide member. Subsequently, the foot 406 can be removed from the guide number and or replaced with another foot 406 (e.g., foot 406 of a different size and/or shape).

Figure 17A:
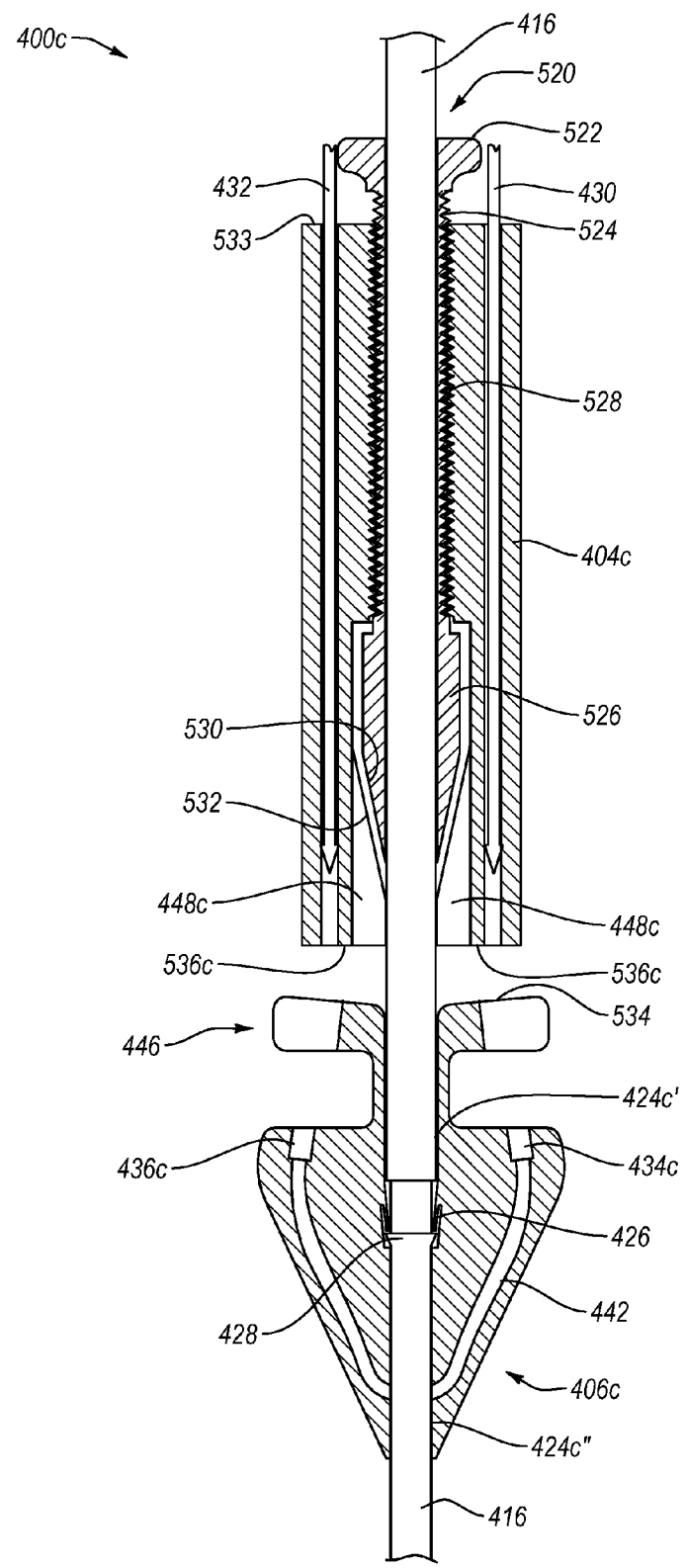
FIG. 17A illustrates a cross-sectional view of a suturing device with a replaceable foot in a pre-deployed configuration in accordance with yet another implementation of the present invention.
Figure 17B:
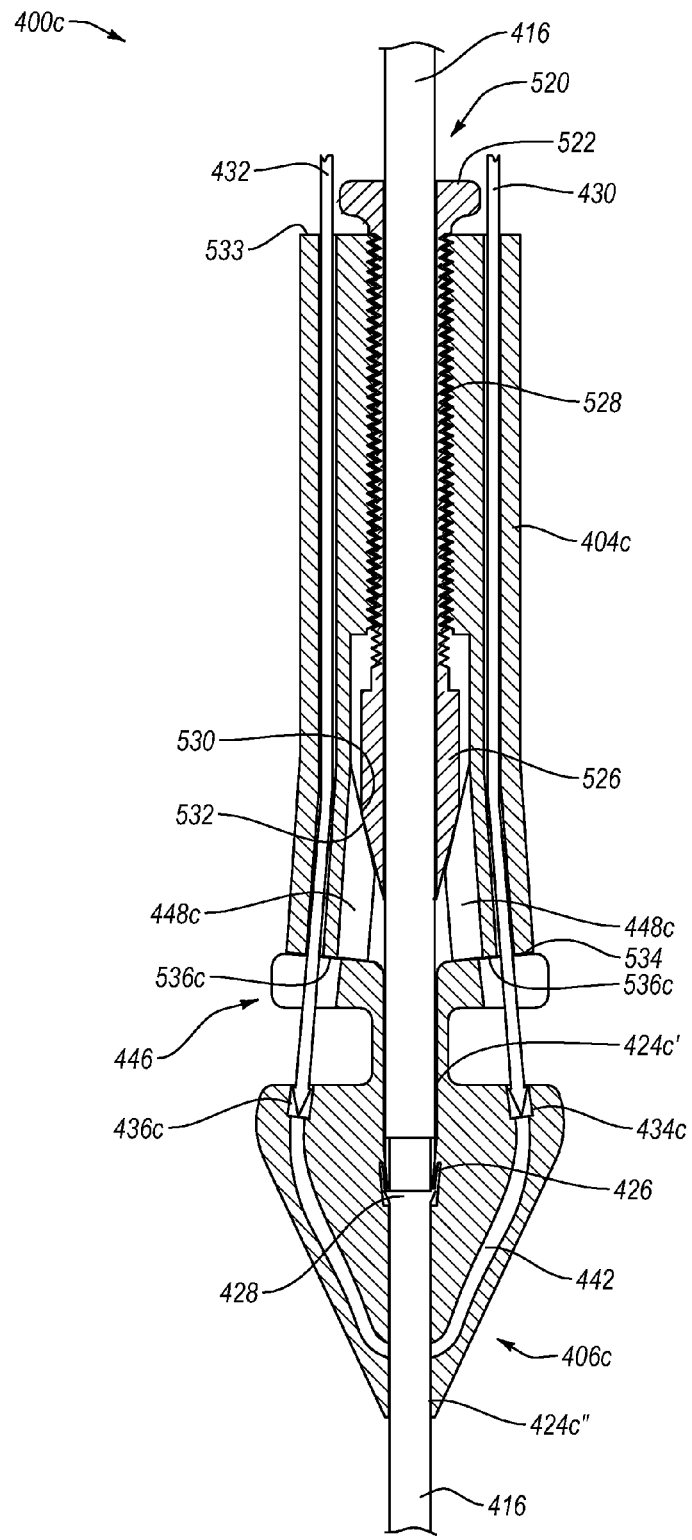
FIG. 17B illustrates a cross-sectional view of a suturing device of FIG. 17A in a deployed configuration.

In some embodiments, the body of the suturing device can be adjusted independent of the foot thereof. In other words, positions or angles of the leafs can be adjusted without having the proximal end of the foot enter the distal end of the body. For example, FIGS. 17A-17B illustrate one embodiment of a suturing device 400c that incorporates a shaft 404c, which can adjust angles of the leafs without having any portion of a foot 406c enter the any portion of the shaft 404c. It should be noted that, except as otherwise described herein, the suturing device 400c may be substantially the same as the suturing device 400a (FIG. 15A) and/or the same as the suturing device 400b (FIG. 15B).

In some embodiments, the suturing device 400c can include a dial adjustment 520 which can flex leafs 448c outward. More specifically, the dial adjustment 520 can include a knob 522 connected to or integrated with a threaded rod 524. Additionally, the dial adjustment 520 can incorporate a wedge 526 that can be secured to or integrated with a distal end of the threaded rod 524. The shaft 404c can have a threaded channel 528 that can accept the threaded rod 524. Consequently, rotation of the threaded rod 524 can advance and retract the threaded rod 524 along the threaded channel 528 (as the threads of the threaded rod 524 and the threaded channel 528 mesh and interact with each other).

For example, the threaded rod 524 and the threaded channel 528 can have respective right-handed external and internal threads. Thus, as the threaded rod 524 rotates in a clockwise direction, the threaded rod 524 can advance along the threaded channel 528 in the distal direction. Similarly, as the threaded rod 524 rotates in a counterclockwise direction, the threaded rod 524 can advance along the threaded channel 528 in the proximal direction. In other embodiments, the threaded rod 524 and the threaded channel 528 can have respective left-handed external and internal threads. As such, rotation of the threaded rod 524 in the clockwise direction can advance the threaded rod 524 in the proximal direction, while rotating the threaded rod 524 in the counterclockwise direction can advance the threaded rod 524 in the distal direction.

The wedge 526 can have a distal end 530 that may have a substantially wedge-like shape or conical shape (i.e., a taper). Each of the leafs 448c also can have proximal ends 532 that have tapers, which can correspond with the taper of the distal end 530. As the dial adjustment 520 moves in the distal direction, the distal end 530 can engage and press against the tapes of the proximal ends 532. Consequently, when the distal end 530 presses against the proximal ends 532, the leafs 448c can flex outward (FIG. 17B).

In one or more embodiments, a top surface 533 of the shaft 404c can have markings that can correspond with one or more markings on the knob 522 of the dial adjustment 520. Such markings can allow rotation of the dial adjustment 520 by a predetermined amount and/or to a predetermined angular position. When the dial adjustment 520 rotates to a predetermined position, the wedge 526 can advance by a predetermined amount toward the distal end of the shaft 404c. Consequently, the wedge 526 can push on the distal end 530 by a predetermined amount, thereby flexing the leafs 448c to a predetermined angle. In other words, the leafs 448c of the suturing device 400c can be dialed to a predetermined angular position, thereby reconfiguring the suturing device 400c into a deployed configuration.

As noted above, the predetermined angle of the leafs 448c can correspond with the predetermined angle of needle capture devices 434c, 436c located in the foot 406c. Furthermore, locations and angle of the needle capture devices 434c, 436c can be such as to allow the piercing ends 431, 433 of the needles 430, 432 to enter and engage the needle capture devices 434c, 436c. Also, locations and angle of the needle capture devices 434c, 436c can be at least in part based on the size of the opening which is intended to be closed by the suturing device 400c.

In some embodiments, a proximal end 446c can have an inward-facing tapered surface 534. Furthermore, the angle of the inward-facing tapered surface 534 can correspond with the angle formed by the leafs 448c and the deployed configuration. For instance, surfaces 536c, which define the lowermost portion of the leafs 448c, can be substantially perpendicular to the center axis of the shaft 404c. Accordingly, as the leafs 448c flex outward into the deployed configuration, the surfaces 536c can form an angle with respect to the center axis of the shaft 404c. Such angle may be a complementary angle of the predetermined angle formed by the leafs 448c. Consequently, if the foot 406c moves in the proximal direction, such that the inward-facing tapered surface 534 comes into contact with the surfaces 536c, the inward-facing tapered surface 534 and the surfaces 536c can seamlessly abut one another (FIG. 17B).

Additionally, matching the inward-facing tapered surface 534 with the surfaces 536 can help to further locate the foot 406c relative to the shaft 404c. Such locating can facilitate proper engagement of the needles 430, 432 with the needle capture devices 434c, 436c. As described above, the foot 406c can be moved in the proximal direction by moving the guide member 416 in the proximal direction. Furthermore, the foot 406c also can have the snap-in features 426, which can snap about the protrusions 428 of the guide member 416, thereby securing the foot 406c to the guide member 416.

In at least one embodiment, the guide member 416 can have an upper attachment lumen 424c' and a lower attachment lumen 424c". The upper attachment lumen 424c' can have a larger cross-section than the lower attachment lumen 424c". Thus, the foot 406c can be inserted over the guide member 416, such that the upper attachment lumen 424c' can pass over the guide member 416, followed by the snap-in features 426 passing over and engaging the protrusions 428, and followed by the lower attachment lumen 424c". In any event, the foot 406c can be located about the upper attachment lumen 424c' and/or about the lower attachment lumen 424c".

Figure 18:
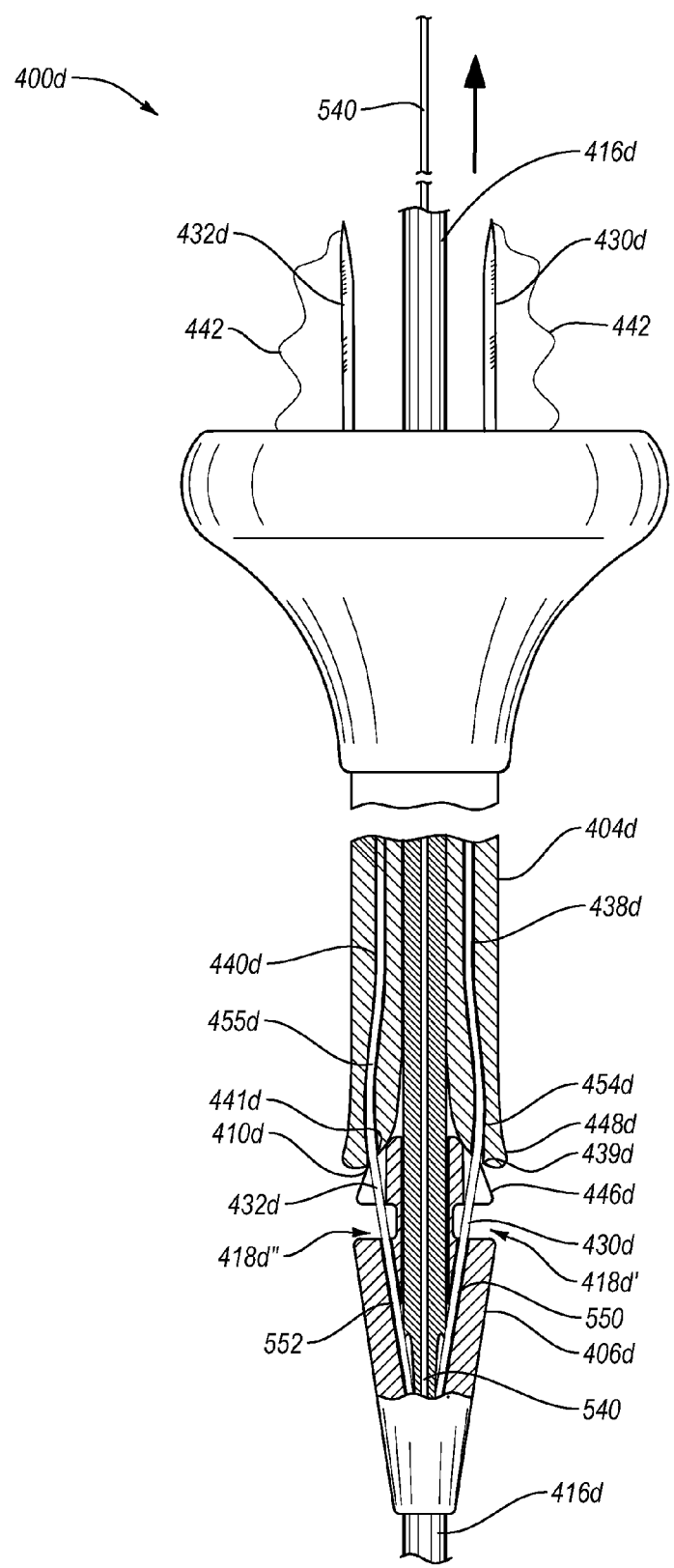
FIG. 18 illustrates a partial cross-sectional view of a suturing device in accordance with still another implementation of the present invention shown in a deployed configuration.

Although the suturing devices described above provide the needles from a proximal portion of the device (i.e. from the body), and can move the needles in the distal direction, it should be noted that this disclosure is not so limited. For instance, as illustrated in FIG. 18, a suturing device 400d can have needles 430b, 432d that can move from the distal portion of the suturing device 400d to the proximal portion thereof. Particularly, the suturing device 400d can include a guide member 416d that can house the needles 430d, 432d.

Additionally, the guide member 416d can house a cable 540. The cable 540 can be connected to the needles 430d, 432d. Thus, when the cable 540 moves in the proximal direction, the needles 430d, 432d also can move and the proximal direction. The guide member 416d is more fully described in the U.S. Pat. No. 7,445,626, entitled "Device and Method for Suturing Tissue," the entire content of which is incorporated herein by reference.

Similar to the suturing device 400b (FIG. 15B), the suturing device 400d can include a shaft 404d and a foot 406d. The foot 406d can couple to the guide member 416d (in any number of ways, as described above). At least a portion of the guide member 416d can be located in and/or pass through the shaft 404d (i.e., through a guide lumen 420d within the shaft 404d). The shaft 404d also can have needle lumens 438d, 440d that terminate at first and second needle entrance openings 439d, 441d.

In some embodiments, a proximal end 446d of the foot 406d can have a tapered shape (similar to the proximal end 446b of the foot 406b (FIG. 15B)). Moreover, a distal end 410d of the shaft 404d can have an internal taper that can correspond with the taper of the proximal end 446d (similar to the suturing device 400b (FIG. 15B)). Thus, the proximal end 446d can enter the distal end 410d, thereby spreading leafs 448d outward. Also, the leafs 448d can be spread to a predetermined angle (as described above).

Needle lumen portions 454d, 455d can be located in the leafs 448d. Hence, when the leafs 448d flex to the predetermined angle, the needle lumen portions 454d, 455d also can flex to a predetermined angle, which can be the same as the predetermined angle of the leafs 448d. The foot 406d can include needle connector lumens 550, 552 which can channel the needles 430d, 432d from the guide member 416d and toward the needle entrance openings 439d, 441d of the needle lumen portions 454d, 455d, and, subsequently, through the needle lumens 438d, 440d. The needle connector lumens 550, 552 can be located at the same predetermined angle as the needle lumen portions 454d, 455d, which can facilitate seamless entry of the needles 430d, 432d into the needle lumen portions 454d, 455d.

Consequently, as the cable 540 moves in the proximal direction, the needles 430d, 432d also can move in the proximal direction and can exit the guide member 416d at corresponding needle exit openings. Subsequently, the needles 430d, 432d can enter the needle connector lumens 550, 552 and can be guided toward the needle entrance openings 439d, 441d of the needle lumens 438d, 440d. As the needles 430d, 432d move further in the proximal direction, the needles 430d, 432d can enter the needle lumen portions 454d, 455d, the needle lumens 438d, 440d, and can exit the shaft 404d at a proximal end thereof. After the needles 430d, 432d exit the shaft 404d, the user can grasp the needles 430d, 432d and can entirely remove the needles from the shaft 404d.

In addition to the needles 430d, 432d, the guide member 416d also can house the length of suture 442, opposing ends of which can be connected to the needles 430d, 432d. As the needles 430d, 432d exit the guide member 416, the needles 430d, 432d can pass through one or more tissue ports (e.g., through tissue ports 418d', 418d"). As noted above, the tissue surrounding the opening in the body lumen can enter tissue ports 418d', 418d", after the foot 406d of the suturing device 400d enters the opening.

As the needles 430d, 432d move out of the needle connector lumens, the needles 430d, 432d can move together with the length of suture 442 and can pass through the tissue ports 418*d'*, 418*d"* and through the tissue surrounding the opening, which can be positioned within the tissue ports 418*d'*, 418*d"*. Thus, at least a portion of the length of suture 442 can pass through the tissue surrounding the opening in the body lumen. In addition to removing the needles 430*d*, 432*d* from the shaft 404*d*, the user also can remove the suturing device 400*d* from the opening. Subsequently, the length of suture 442 can be used to close the opening.

Figure 19B:
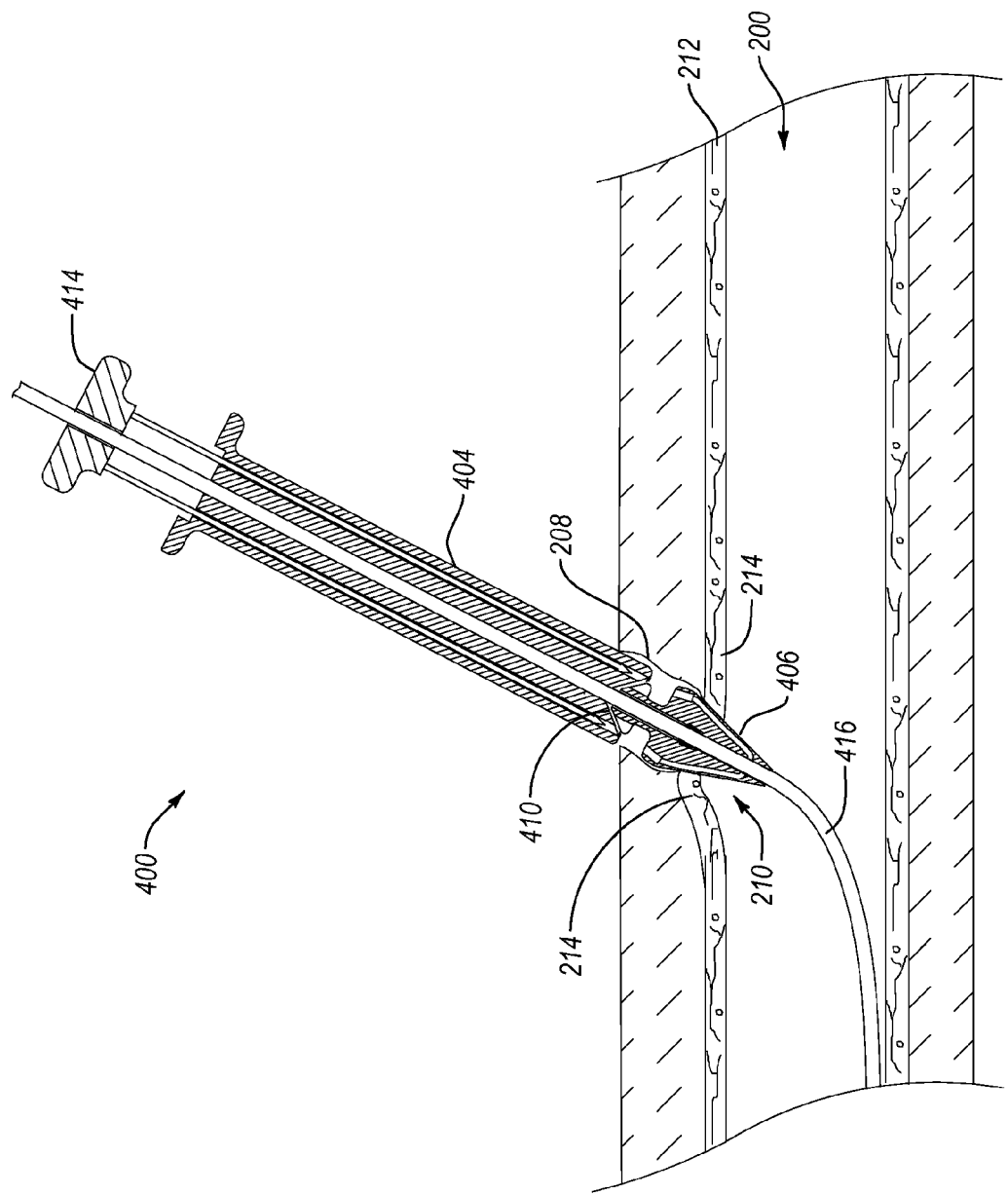

Referring now to FIGS. 19A-19F; FIGS. 19A-19F illustrate an embodiment of a method of using the suturing device 400. It should be noted that the acts illustrated in FIGS. 19A-19F are equally applicable to all of the various embodiments of the suturing device, including but not limited to the embodiments of suturing devices 400*a*, 400*b*, 400*c*, 400*d* (FIGS. 15A-18). As illustrated in FIG. 19A, the guide member 416 can enter the body lumen 200 through the tissue tract 208 and then through the opening 210. More specifically, the tissue tract 208 can pass through the patient's skin 204 and through the tissue 206. The tissue tract 208 can connect with the opening 210 that passes through the lumen wall 212 and into the body lumen 200. As noted above, the suturing device 400 can move along or together with the guide member 416 into the opening 210. Alternatively, a guidewire can pass through the guide member 416 and into the body lumen 200, and the suturing device 400, together with the guide member 416, can move along the guidewire into the opening 210.

As the guide member 416 enters the body lumen 200, the suturing device 400 can be in the pre-deployed configuration. In other words, the leafs 448 can be un-flexed or in a original position. Alternatively, as the guide member 416 enters the opening 210 in the body lumen 200, the suturing device 400 can be in the deployed configuration, with the leafs 448 flexed to the predetermined angle (the needles 430, 432 may be in a retracted position). Furthermore, in some embodiments, the proximal end of the foot 406 may be in contact with or separated from the distal end 410 of the shaft 404.

As illustrated in FIG. 19B, after the guide member 416 enters the body lumen 200, the foot 406 and the shaft 404 can move along or together with the guide member 416 through the tissue tract 208. As the suturing device 400 moves through the tissue tract 208, the foot 406 can pass through the lumen wall 212 and enter the opening 210. To the extent that foot 406 has a taper on the distal end thereof, such taper can facilitate the entry of the suturing device 400 into the tissue tract 208 and into the opening 210. Particularly, such taper can facilitate entry of the foot 406 into the opening 210.

As described above, the size and shape of the foot 406 can be chosen at least in part based on the size and shape of the opening 210. In some embodiments, the size of the foot 406 can be such as to dilate the opening 210 to a desired size and/or shape, as the foot 406 enters the opening 210. For example, the foot 406 can dilate the opening 210 to a desired size for closing the opening 210. The tissue 214 surrounding the opening 210 can at least in part tear in response to the dilation caused by the foot 406. In other words, the dilation of the opening 210 can be achieved in part by elastic stretching and in part by tearing.

By choosing an appropriately sized and/or shaped foot 406, the final size of the opening 210 (i.e., the size of the opening after stretching and/or tearing as the foot 406 passes into the body lumen 200) can be controlled. Furthermore, the final size of the dilated opening 210 can be such that would allow the needles 430, 432 to be deployed into the tissue surrounding the opening 210. Among other things, such dilation may eliminate or reduce the risk of tearing the suture out of the tissue 214 surrounding the opening 210 during the closure of the opening 210. It should be noted that tearing, including partial tearing, of the suture out of the tissue 214 can result in an incomplete closure of the opening 210.

Figure 19C:
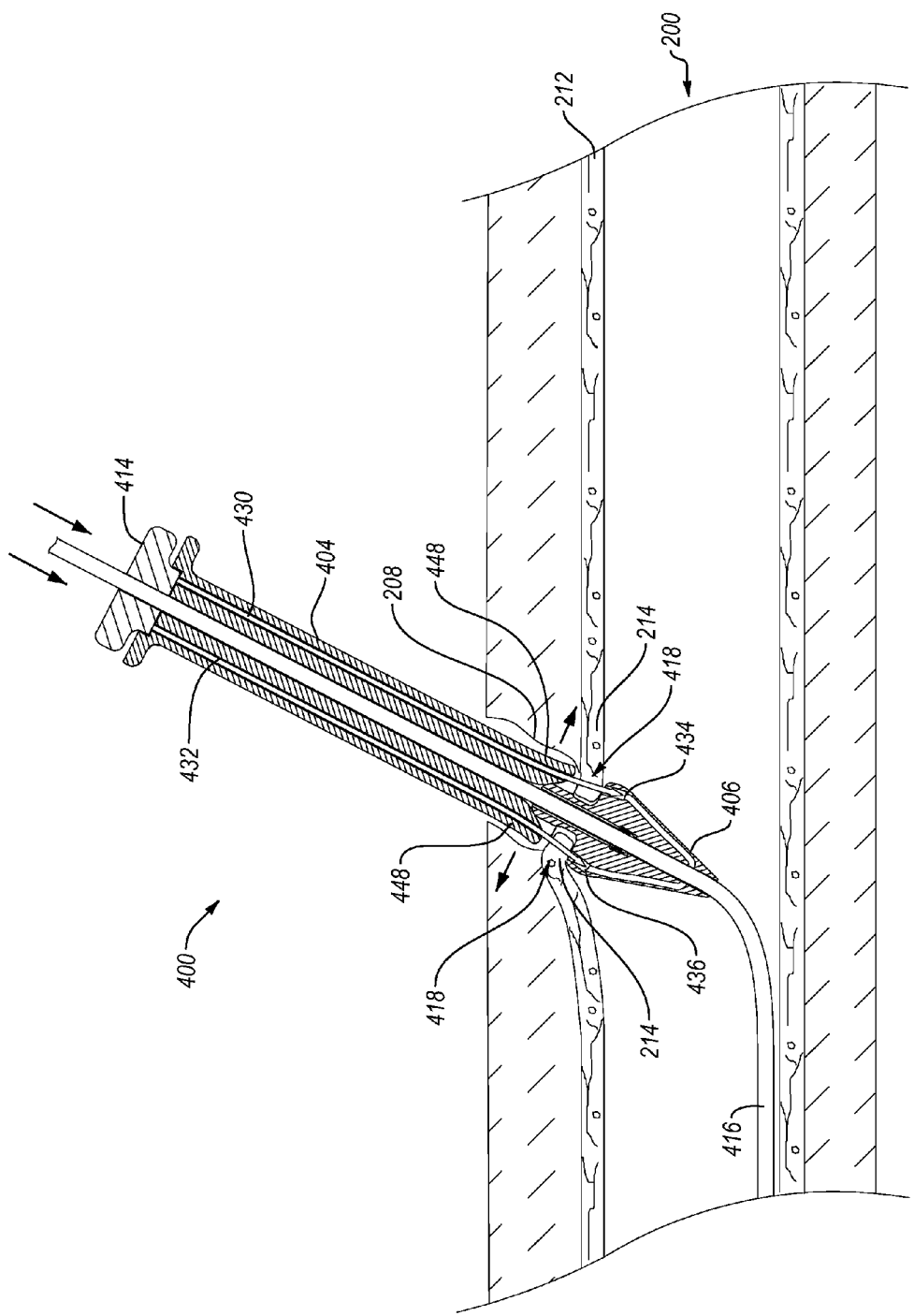

Additionally, as illustrated in FIG. 19C, the tissue 214 can contract when the foot 406 passes into the body lumen 200 such that the tissue ports 418 can accept the tissue 214. Particularly, as the tissue 214 enters the tissue ports 418, the tissue 214 can contract within the tissue ports 418 such as to overlap needle capture devices 434, 436. In other words, the tissue 214 can close in around a center portion of the foot 406 located within the tissue ports 418. As the foot 406 captures the tissue 214 within the tissue ports 418, the user may be able to feel the resistance created by such capture to recognize that the suturing device 400 has reached a desired position for closing the opening 210.

In some embodiments, as the suturing device 400 passes through the tissue tract 208, the proximal end of the foot 406 can be pushed into the distal end of the shaft 404 thereby spreading the leafs 448 outward (as indicated by the arrows). As the leafs 448 spread to a predetermined position, the suturing device 400 is reconfigured into the deployed configuration, as described above. The guide member 416 can be pulled in the proximal direction. As the guide member 416 moves in the proximal direction, the foot 406 also can move and the proximal direction thereby entering the distal end of the shaft 404 and spreading the leafs 448. Additionally, as noted above, the leafs 448 can remain spread outward to a predetermined angle for a desired period of time or for desired steps or acts in the method of closing the opening in the body lumen 200.

Once the suturing device 400 is in the deployed position, the actuation handle 414 can actuate the needles 430, 432 (as indicated by the arrows). More specifically, the handle 414 can move the needles 430, 432 in the distal direction, toward the needle capture devices 434, 436. As the needles 430, 432 to pass through the needle lumen portions located in the leafs 448, the needles 430, 432 can flex out word to a predetermined angle which can match the angle of the needle capture devices 434, 436. Consequently, the needles 430, 432 can engage and couple to the needle capture devices 434, 436. Furthermore, when the needles 430, 432 pass through the tissue ports 418, the needles 430, 432 can enter and pass through the tissue 214. Hence, when the needles 430, 432 engage the needle capture devices 434, 436, the needles 430, 432 also can engage in pass through the tissue 214.

As illustrated in FIG. 19D, after the needles 430, 432 engage the needle capture devices 434, 436, the needles 430, 432 can be withdrawn (i.e., moved in the proximal direction), as indicated by the arrows. Thus, as the needles 430, 432 are withdrawn and move in the proximal direction, the needle capture devices 434, 436 as well as the length of suture 442 attached thereto can be pulled together with the needles 430, 432 through the tissue 214. The length of suture 442 can detach from the foot 406 and a portion of the length of suture 442 that is connected to the needle capture devices 434, 436 can enter and pass through the tissue 214. Furthermore, needle capture devices 434, 436 and the length of suture 442 can enter and pass through the respective needle lumens 438, 440 and or the proximal end of the shaft 404, exiting the needle lumens 438, 440 and the shaft 404.

Figure 19E:
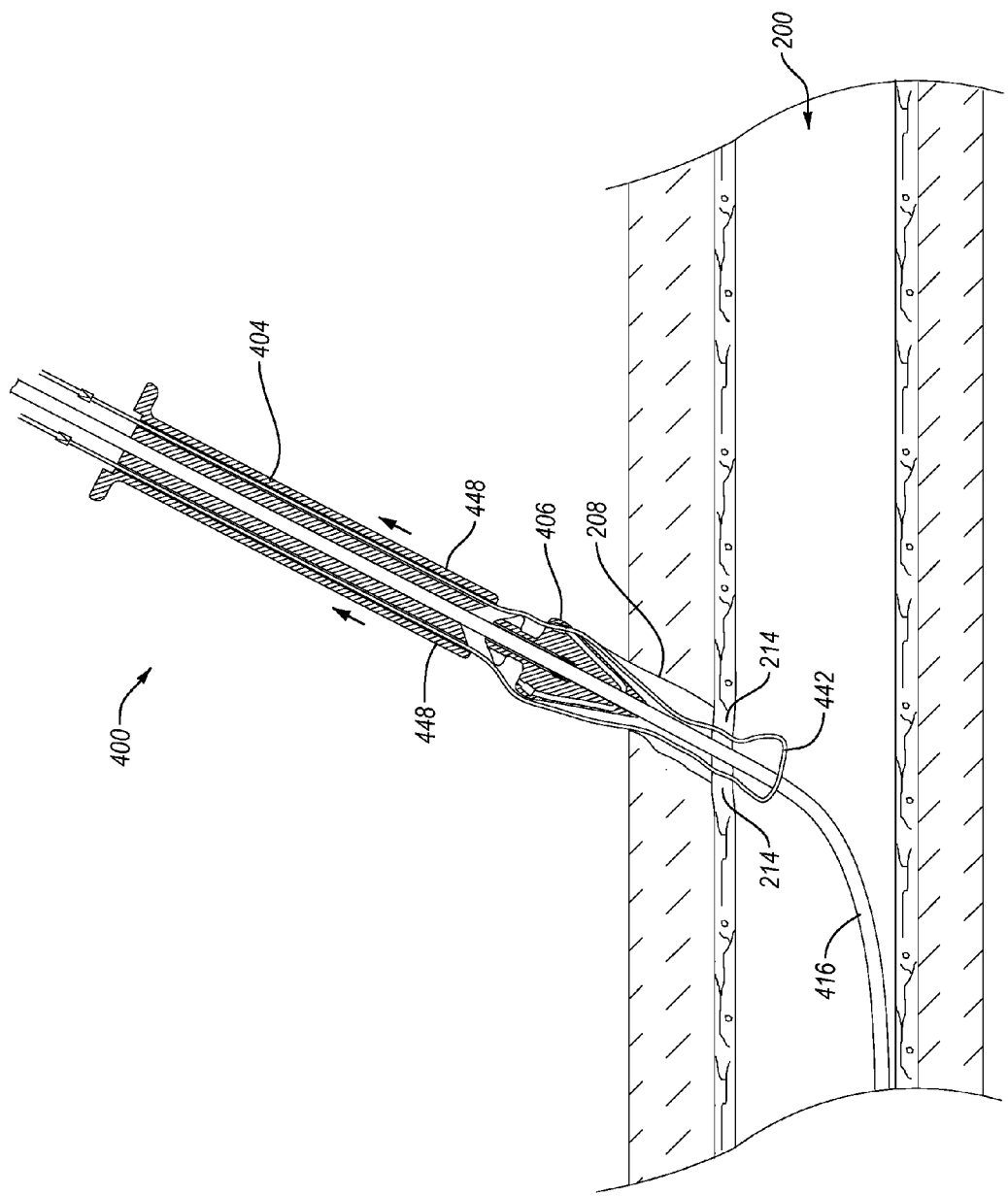

Subsequently, as illustrated in FIG. 19E, the suturing device 400 can be withdrawn from the opening in the body lumen 200 and from the tissue tract 208. More specifically, the shaft 404 and/or the guide member 416 can move in the proximal direction, as indicated by the arrows. The user also can pull the guide member 416 in the proximal direction, thereby pulling on the foot 406 and on the shaft 404 and removing the suturing device 400 from the opening 210 and from the tissue tract 208.

Figure 19F:
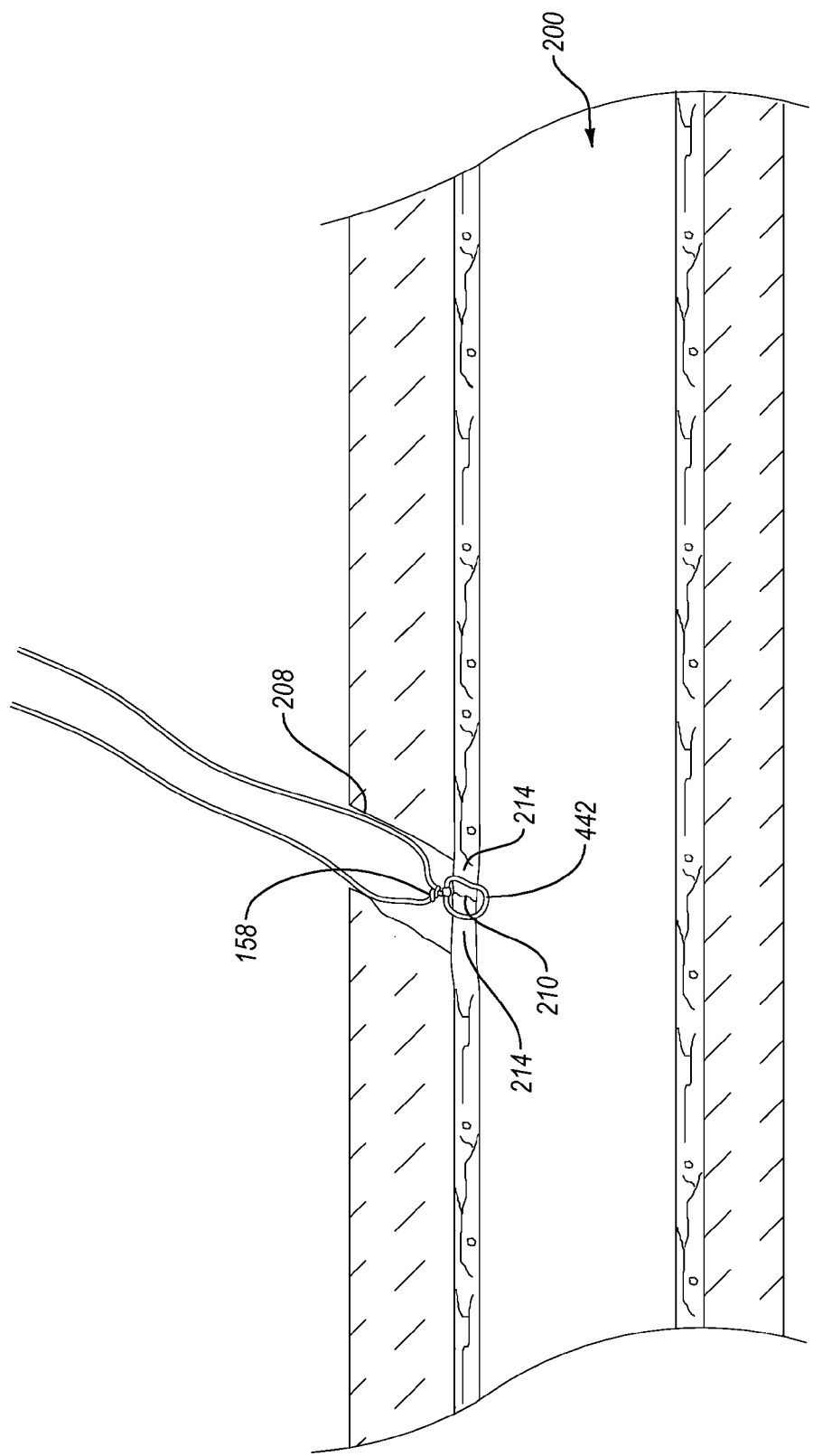

In some embodiments, as the shaft 404 moves in the proximal direction, the distal end of the shaft 404 can separate from the proximal end of the foot 406, allowing the leafs 448 to contract or flex back to their original position, thereby reconfiguring the suturing device 400 into a post-deployed configuration. Also, as the suturing device 400 is removed from the opening 210, the length of suture 442 can remain within the tissue 214. Accordingly, the length of suture 442 can close the opening 210, after the suturing device 400 is removed from the opening 210. Particularly, as illustrated in FIG. 19F, after the suturing device is removed from the opening 210 and from the tissue tract 208, the needle capture devices can be removed from the length of suture 442. Alternatively, the needle capture devices can be removed from the needles and can remain attached to the length of suture 442.

Thereafter, the opening 210 can be closed to promote hemostasis. More specifically, the surgical knot 158 can be formed by tying the ends of the length of suture 442 about the opening 210. Thus, the length of suture 442 together with the surgical knot 158 can pull together the tissue 214 surrounding the opening 210, thereby closing the opening 210.

The embodiments of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. For example, the sutures described herein can further be prearranged to define a pre-tied knot, such as the pre-tied knots disclosed in U.S. Pat. No. 7,235,087 previously incorporated herein. Additionally, the suturing devices of the present invention can further include barbed sutures, or be used to deploy cleats or other devices to aid in closing a body lumen opening. Furthermore, where structures, elements, acts, steps, or stages have been described with reference to a specified implementation or device; each of the individual structures, elements, acts, steps, or stages, or a combination thereof, are contemplated to be combinable with each other and with other implementations and devices described herein. All changes which come within the meaning and range of equivalency of the claims are to be embraced within their scope.

What is claimed is:

1. A suturing device configured to close an opening in a body lumen, the suturing device comprising:
    a shaft having a distal end and a proximal end, the shaft comprises a plurality of leafs that define the distal end of the shaft, the leafs being configured to flex outward relative to a center axis of the shaft in response to a force applied to the leafs;
    a first needle lumen disposed within the shaft, the first needle lumen terminating at a first needle exit opening at the distal end of the shaft;
    a second needle lumen disposed within the shaft, the second needle lumen terminating at a second needle exit opening at the distal end of the shaft;
    a guide member slidably located within the shaft and extending past the distal end of the shaft;
    a foot selectively coupled to the guide member, a proximal end of the foot being positioned proximally to the distal end of the shaft;
    a first needle capture device removably secured to the foot;
    a second needle capture device removably secured to the foot; and
    at least one length of suture secured to the foot, the at least one length of suture having a first end secured to the first needle capture device and a second end secured to the second needle capture device.

2. The suturing device of claim 1, wherein:
    the distal end of the shaft has an tapered cavity formed therein; and
    a proximal end of the foot has a tapered shape configured to fit into the tapered cavity in the distal end of the shaft in a manner that the foot applies force to the leafs to flex the leafs outward.

3. The suturing device of claim 2, wherein the proximal end of the foot has a stop surface configured to contact a corresponding portion of the tapered cavity in the distal end of the shaft.

4. The suturing device of claim 3, wherein the stop surface and the taper of the tapered cavity and the tapered shape of the foot determine a predetermined position of the flexed leafs.

5. The suturing device of claim 1, wherein:
    at least a portion of the first needle lumen is associated with a first leaf of the plurality of leafs; and
    at least a portion of the second needle lumen is associated with a second leaf of the plurality of leafs.

6. The suturing device of claim 1, further comprising a dial adjustment located in the shaft, the dial adjustment being configured to apply force onto the leafs to flex the leafs outward.

7. The suturing device of claim 6, wherein the dial adjustment further comprises:
    a threaded rod that is threaded into a threaded channel of the shaft; and
    a wedge coupled to the threaded rod, the wedge being configured to apply force onto proximal ends of the leafs to flex the leafs outward.

8. The suturing device of claim 1, wherein the shaft further comprises a plurality of slots that form the leafs.

9. The suturing device of claim 1, further comprising a first needle and a second needle configured to engage respective first and second needle capture devices.

10. The suturing device of claim 1, wherein the foot is removably coupled to the guide member.

11. The suturing device of claim 1, wherein the foot further comprises one or more tissue ports configured to accept tissue surrounding the opening in the body lumen.

12. The device of claim 1, wherein a distal end of the foot has a substantially conical shape.

13. A suturing device configured to close an opening in a body lumen, the suturing device comprising:
    a shaft having a distal end and a proximal end, the shaft comprises a plurality of leafs that define the distal end of the shaft, the leafs being configured to flex outward relative to a center axis of the shaft in response to a force applied to the leafs;
    a first needle lumen disposed within the shaft, the first needle lumen terminating at a first needle entrance opening at the distal end of the shaft;
    a second needle lumen disposed within the shaft, the second needle lumen terminating at a second needle entrance opening at the distal end of the shaft;
    a guide member slidably positioned within the shaft and extending past the distal end of the shaft, the guide member having a first needle and a second needle, the first and second needles having piercing ends;
    a length of suture having a first and second ends thereof secured to the first and second needles; and
    a foot coupled to the guide member, the foot having a first needle connector lumen and a second needle connector lumen, the first and second needle connector lumens being configured to guide the first and second needles out of the guide member and into the first and second entrance openings in the shaft.

14. The suturing device of claim 13, wherein:
the distal end of the shaft has a tapered cavity formed therein; and
a proximal end of the foot has a tapered shape configured to fit into the tapered cavity in the distal end of the shaft in a manner that the foot applies force to the leafs to flex the leafs outward.

15. The suturing device of claim 13, wherein the foot further comprises one or more tissue ports configured to accept tissue surrounding the opening in the body lumen.

16. A method of closing an opening in a body lumen, the method comprising:
inserting a guide member of a suturing device through the opening and into the body lumen;
inserting a foot of the suturing device into the opening and capturing tissue surrounding the opening in one or more tissue ports of the foot;
adjusting a shaft of the suturing device in a manner that needle exit openings located in the shaft correspond with needle capture devices located in the foot, the shaft comprises a plurality of leafs that define a distal end of the shaft, the leafs being configured to flex outward relative to a center axis of the shaft in response to a force applied to the leafs;
passing a plurality of needles through the shaft, out of the needle exit openings, through the tissue surrounding the opening, and into corresponding needle capture devices; and
retrieving the plurality of needles together with the corresponding needle capture devices, thereby passing a length of suture attached to the needle capture devices through the tissue surrounding the opening.

17. The method of claim 16, wherein adjusting a shaft of the suturing device in a manner that needle exit openings located in the shaft correspond with needle capture devices located in the foot comprises flexing outward a plurality of leafs comprising a distal end of the shaft.

18. The method of claim 17, wherein flexing outward the plurality of leafs comprises pressing a tapered proximal end of the foot into a tapered cavity in the distal end of the shaft.

* * * * *